(12) United States Patent
Rahilly et al.

(10) Patent No.: US 11,100,741 B2
(45) Date of Patent: Aug. 24, 2021

(54) SECURE INVENTORY ACCESS AND CONTROL MECHANISM

(71) Applicant: CareFusion 303, Inc., San Diego, CA (US)

(72) Inventors: Michael Rahilly, Encinitas, CA (US); Brendan John Burgess, Poway, CA (US); Ramkumar Subramanian, San Diego, CA (US); Mustafa Yusufi, Escondido, CA (US); Monica Wyly, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 16/914,204

(22) Filed: Jun. 26, 2020

(65) Prior Publication Data

US 2020/0410801 A1 Dec. 31, 2020

Related U.S. Application Data

(60) Provisional application No. 62/867,841, filed on Jun. 27, 2019, provisional application No. 62/937,181, (Continued)

(51) Int. Cl.
*G07C 9/29* (2020.01)
*G06Q 10/08* (2012.01)
*G16H 40/20* (2018.01)
*G07C 9/25* (2020.01)
*G06K 7/10* (2006.01)
*E05B 47/00* (2006.01)
(Continued)

(52) U.S. Cl.
CPC ............ *G07C 9/29* (2020.01); *E05B 47/0001* (2013.01); *E05B 65/0042* (2013.01); *G06K 7/10297* (2013.01); *G06Q 10/087* (2013.01); *G07C 9/25* (2020.01); *G16H 40/20* (2018.01); *A61J 1/00* (2013.01); *E05Y 2900/20* (2013.01);
(Continued)

(58) Field of Classification Search
CPC ......... G07C 9/29; G07C 9/25; E05B 65/0042; E05B 47/0001; G06K 7/10297; G16H 40/20; G16H 40/67; G16H 20/10; G06Q 10/087; F25D 29/005; F25D 29/008;
(Continued)

(56) References Cited

U.S. PATENT DOCUMENTS 6,204,763 B1 * 3/2001 Sone .................... A47G 29/141
221/2
8,600,548 B2 * 12/2013 Bossi .................... G16H 40/67
700/240
(Continued)

OTHER PUBLICATIONS

International Search Report and Written Opinion for Application No. PCT/US2020/040000, dated Sep. 3, 2020, 13 pages.

*Primary Examiner* — Adnan Aziz
(74) *Attorney, Agent, or Firm* — Morgan, Lewis & Bockius LLP

(57) ABSTRACT

Secure medication storage is described herein. A smart latch includes an actuator, a communication interface, a display, and a processor. The actuator is configured to open and close a latch to secure a door of the enclosure. The processor can be configured to receive a user credential for accessing the enclosure, validate the user credential for accessing the enclosure, trigger the actuator to open the latch, thereby allowing the door to be opened, and trigger the actuator to close the latch after detecting that the door is closed, thereby securing the door.

9 Claims, 42 Drawing Sheets

Related U.S. Application Data filed on Nov. 18, 2019, provisional application No. 63/038,060, filed on Jun. 11, 2020.

(51) Int. Cl.
*E05B 65/00* (2006.01)
*A61J 1/00* (2006.01)
*F25D 23/02* (2006.01)
*F25D 29/00* (2006.01)

(52) U.S. Cl.
CPC ......... *E05Y 2900/31* (2013.01); *F25D 23/028* (2013.01); *F25D 29/005* (2013.01); *F25D 29/008* (2013.01); *F25D 2323/02* (2013.01)

(58) Field of Classification Search
CPC .............. F25D 2323/02; F25D 23/028; E05Y 2900/31; E05Y 2900/20; A61J 1/00; G06F 19/3456
See application file for complete search history.

(56) References Cited

U.S. PATENT DOCUMENTS

| | | | | |
|---|---|---|---|---|
| 9,911,290 | B1* | 3/2018 | Zalewski | G06Q 20/327 |
| 10,614,413 | B2* | 4/2020 | Curry | G06K 7/1413 |
| 10,653,583 | B1* | 5/2020 | Walker | A61J 7/0069 |
| 2003/0236683 | A1* | 12/2003 | Henderson | G16H 20/10 |
| | | | | 705/2 |
| 2007/0125100 | A1 | 6/2007 | Shoenfeld | |
| 2009/0132090 | A1 | 5/2009 | Kaczmarz et al. | |
| 2009/0231132 | A1* | 9/2009 | Shoenfeld | E05B 63/24 |
| | | | | 340/542 |
| 2011/0074543 | A1* | 3/2011 | Kaczmarz | G07C 9/00896 |
| | | | | 340/5.73 |
| 2013/0282392 | A1* | 10/2013 | Wurm | G16H 20/13 |
| | | | | 705/2 |
| 2014/0089243 | A1* | 3/2014 | Oppenheimer | G06F 21/88 |
| | | | | 706/46 |
| 2015/0193731 | A1* | 7/2015 | Stevens | G06Q 10/083 |
| | | | | 705/26.7 |
| 2015/0223891 | A1* | 8/2015 | Miller | G06F 21/44 |
| | | | | 726/19 |
| 2016/0089303 | A1 | 3/2016 | Latorraca et al. | |
| 2016/0300187 | A1* | 10/2016 | Kashi | G06Q 10/0832 |
| 2018/0129998 | A1* | 5/2018 | Frazier | G06Q 10/0832 |
| 2018/0150613 | A1* | 5/2018 | Bossi | G06F 16/2358 |
| 2019/0019573 | A1* | 1/2019 | Lake | G16H 15/00 |
| 2019/0057566 | A1* | 2/2019 | Mlynarczyk | G06K 17/0029 |
| 2019/0236527 | A1* | 8/2019 | Bhaumik | G06Q 10/087 |
| 2019/0378602 | A1* | 12/2019 | LaTorraca | A61G 12/001 |
| 2020/0210942 | A1* | 7/2020 | Li | G06Q 30/02 |
| 2020/0323471 | A1* | 10/2020 | Mears | G16H 20/17 |

* cited by examiner

DISPLAY 1365A

Medication A, 38F
Medication B, 40F
Battery: 90%
Network: OK
Door: Locked

DISPLAY 1365B

Medication A, 38F
Medication B, 40F
Battery: 90%
Network: OK
Door: Unlocked

DISPLAY 1365C

Medication A, 50F
Medication B, 50F
*TEMP WARNING*
Battery: 88%
Network: OK
Door: Unlocked

FIG. 11

FIG. 16
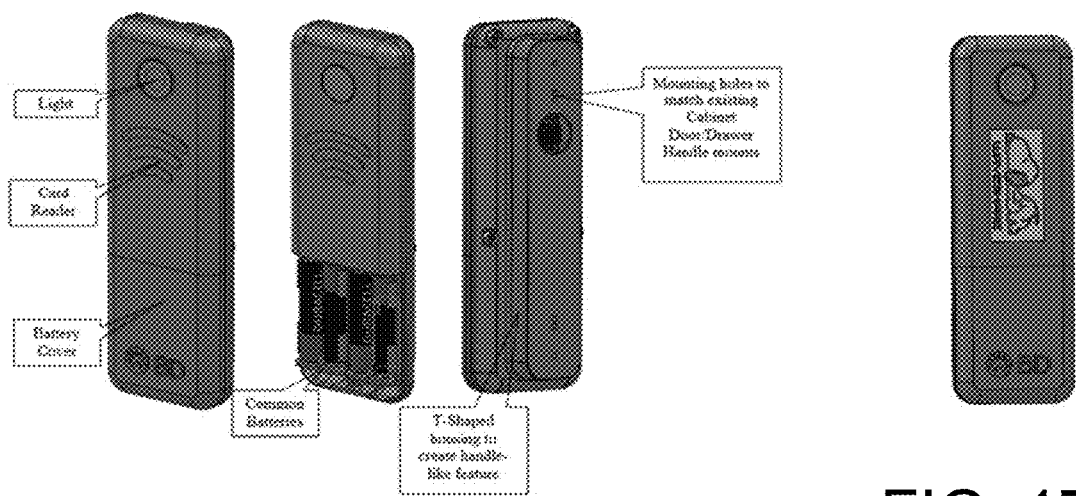
FIG. 17A
FIG. 17B

SECURE INVENTORY ACCESS AND CONTROL MECHANISM

REFERENCE TO RELATED APPLICATIONS

This application claims priority to U.S. Provisional App. No. 62/867,841, filed on Jun. 27, 2019, U.S. Provisional App. No. 62/937,181, filed on Nov. 18, 2019, and U.S. Provisional App. No. 63/038,060, filed on Jun. 11, 2020, all of which are hereby incorporated by reference in its entirety.

FIELD OF THE INVENTION

The present disclosure generally relates to medication storage, and, in particular, to secure medication storage.

BACKGROUND

Medications and other regulated products are often required to be stored in secured storage and dispensing mechanisms. Often, an automated dispensing cabinet (ADC) is used to control access to regulated products. ADCs are often expensive and occupy significant space.

In some settings, existing enclosed space such as drawers, cabinets, and carts are used to store and dispense medications. However, some of these enclosed spaces may lack of security and traceability, and those spaces that do have these features may be resource intensive to manage.

Further, to dispense environmentally (e.g., temperature, humidity, light) sensitive items in both acute and non-acute medical settings, refrigerators may be provided. These sensitive items may include delicate, high value medications, and thus it is preferable to monitor and control the refrigerator environment and restrict access to authorized users. While smart refrigerator designs with temperature monitoring and access control may be available, physical access to specialized dispensing terminals or other bespoke hardware is often required, which limits deployment flexibility and increases implementation cost. This can pose a challenge for various care facilities such as doctor's offices, pharmacy clinics, outpatient clinics, institutional infirmaries (e.g., school nurse offices), hospitals, retail clinics, ambulatory clinics, or the like.

Accordingly, there is a need for improved systems and methods of providing refrigerator access control and temperature monitoring, particularly for clinical settings.

SUMMARY

The disclosed subject matter relates to secure medication storage. In certain embodiments, an access control module is disclosed that comprises a latching module comprising: a latching member; and a latch actuator configured to extend and retract the latching member; and an interface module coupled to the latching module, the interface module comprising: a module body defining a handle portion and an extension portion extending from the handle portion, wherein the extension portion is narrower than the handle portion and the module body is spaced apart from the latching module; an input device configured to receive a user input; and a controller operatively coupled to the latch actuator and configured to authenticate the user input and control the latching member in response to the authenticated user input.

In certain embodiments a storage system is disclosed that comprises a cabinet body defining a cabinet volume; a cabinet door coupled to the cabinet body, wherein the cabinet door is movable to enclose the cabinet volume; and an access control assembly coupled to the cabinet door, the access control assembly comprising: a latching module coupled to an inner surface of the cabinet door, the latching module comprising: a latching member; and a latch actuator configured to extend and retract the latching member relative to the cabinet door; and an interface module coupled to an outer surface of the cabinet door, the interface module comprising: a module body defining a handle portion and an extension portion extending from the handle portion, wherein the extension portion is narrower than the handle portion and the extension portion is adjacent to the outer surface of the cabinet door; an input device configured to receive a user input; and a controller operatively coupled to the latch actuator and configured to authenticate the user input and control the latching member in response to the authenticated user input.

In certain embodiments, a method is disclosed that comprises providing a cabinet body with a cabinet door movable relative to the cabinet body; latching the cabinet door to the cabinet body to retain the cabinet door in a closed position via a latching module; unlatching the cabinet door from the cabinet body via the latching module; moving the cabinet door to an open position; and accessing a cabinet volume defined within the cabinet body.

According to various implementations, a method for providing secure access control and temperature monitoring for a refrigerator is provided. The method may include providing a smart latch for attaching to the refrigerator. The method may also include retrieving, via a communication interface, inventory and temperature status for one or more smart containers within the refrigerator. The method may also include outputting, via a display, the inventory and temperature status. The method may also include receiving user credentials for accessing the refrigerator. The method may also include validating the user credentials for accessing the refrigerator. The method may also include triggering an actuator to open a latch, thereby allowing a door of the refrigerator to be opened. The method may also include triggering the actuator to close the latch after detecting that the door is closed, thereby securing the door.

Other aspects include corresponding systems, apparatuses, and computer program products for implementation of the computer-implemented method.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 11 depicts various example user interfaces of a smart latch, according to various aspects of the subject technology.

FIG. 16 depicts a remote activated keyless lock that may be added to existing cabinet doors and/or existing cabinet drawers for controlled security, according to various aspects of the subject technology.

FIGS. 17A and 17B depict a smart lock including a smart lock reader module, according to various aspects of the subject technology.

DETAILED DESCRIPTION

Access Control Assemblies

Figure 1:
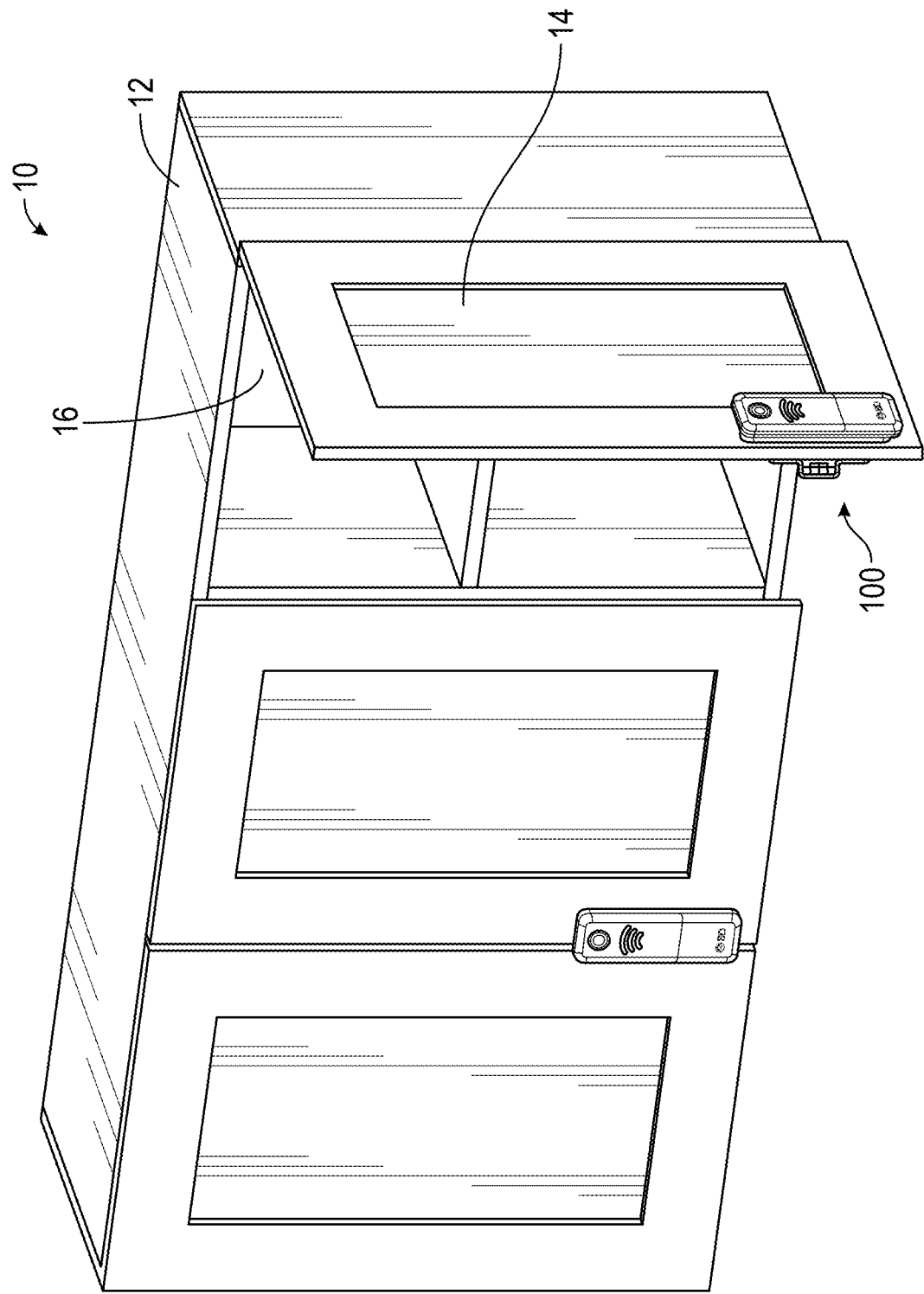
FIG. 1 is a perspective view of a cabinet, in accordance with various aspects of the present disclosure.

The disclosed access control assembly incorporates a latching module and an interface module to control access to inventory. The latching mechanism can engage and disengage a latching member to control access to a storage volume. The interface module can authenticate users and control the actuation of the latching member. By controlling access to the storage volume, inventory, such as medication, can be stored securely.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc., in multiple parts.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the storage of medication using the disclosed access control assemblies, it is to be understood that this description is only an example of usage and does not limit the scope of the claims. Various aspects of the access control assemblies may be used in any application where it is desirable to securely store inventory.

The disclosed access control assembly overcomes several challenges discovered with respect to certain conventional secure medication storage devices. One challenge with certain conventional medication storage devices is that certain conventional medication storage devices may not trace users that accessed stored medication. Further, certain conventional medication storage devices may default to an unlocked state upon depletion of the batteries. Additionally, certain conventional medication devices may be cumbersome and occupy large amounts of space.

In accordance with the present disclosure, it is advantageous to provide access control assemblies as described herein that allow for traceable, space efficient, and secure storage of regulated products, such as medication. The disclosed access control assemblies provide space efficient and secure storage of medication.

Examples of access control assemblies that allow for secure storage are now described.

FIG. 1 is a perspective view of a cabinet 10, in accordance with various aspects of the present disclosure. With reference to FIG. 1, the cabinet 10 in conjunction with the access control assembly 100 can provide secure item storage and retrieval.

As illustrated, the cabinet 10 can allow for the storage of inventory within a cabinet volume 16 defined by the cabinet body 12. As can be appreciated, the cabinet volume 16 can securely store items such as medication or other regulated products. In the depicted example, the cabinet volume 16 can be accessed by opening a cabinet door 14. Access to the cabinet volume 16 and items stored therein can be prevented by closing the cabinet door 14. The cabinet door 14 can be movably coupled to the cabinet body 12 by one or more hinges.

As described herein, the cabinet 10 can include an access control assembly 100 to control access into the cabinet volume 16. The access control assembly 100 can lock the cabinet door 14 to the cabinet body 12 to prevent access into the cabinet volume 16 and items stored therein. During operation, the cabinet door 14 can be unlocked or otherwise released upon authentication of a user. The access control assembly 100 can be mounted opposite to the hinges of the cabinet door 14.

In some applications, the access control assembly 100 can be added or retrofitted to existing cabinet doors 14 to add access control to existing cabinets 10. In some applications, cabinets 10 can include the access control assembly 100 upon original manufacture or assembly.

According to various implementations, the access control assembly 100 can include or be embodied as an access control assembly 100 that is utilized or associated with a refrigerator to control access into the refrigerator, as described herein with respect to FIGS. 9A-13, 21, and 22.

Figure 2:
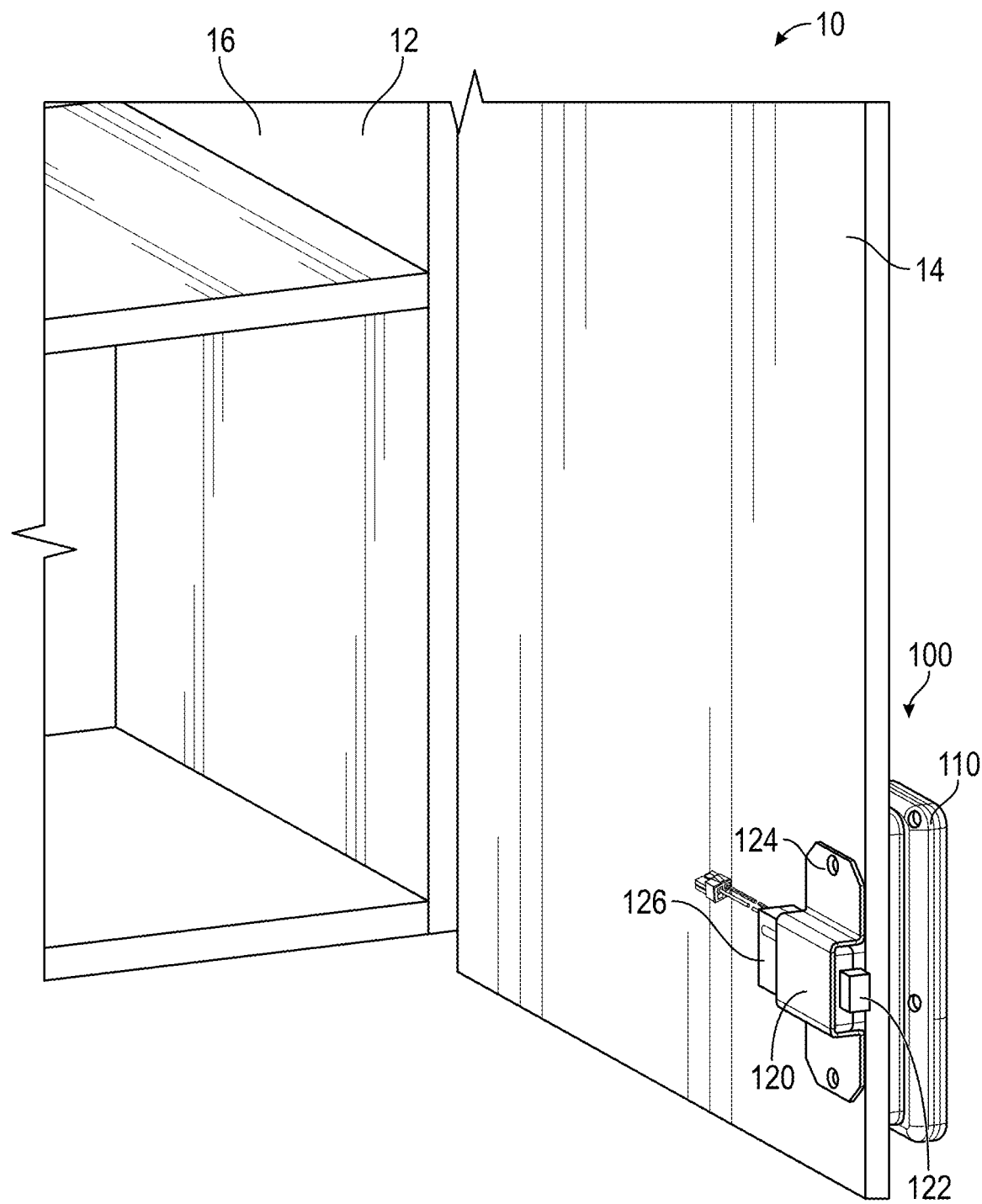
FIG. 2 is a perspective view of the cabinet of FIG. 1 with a cabinet door in an open position.
Figure 3:
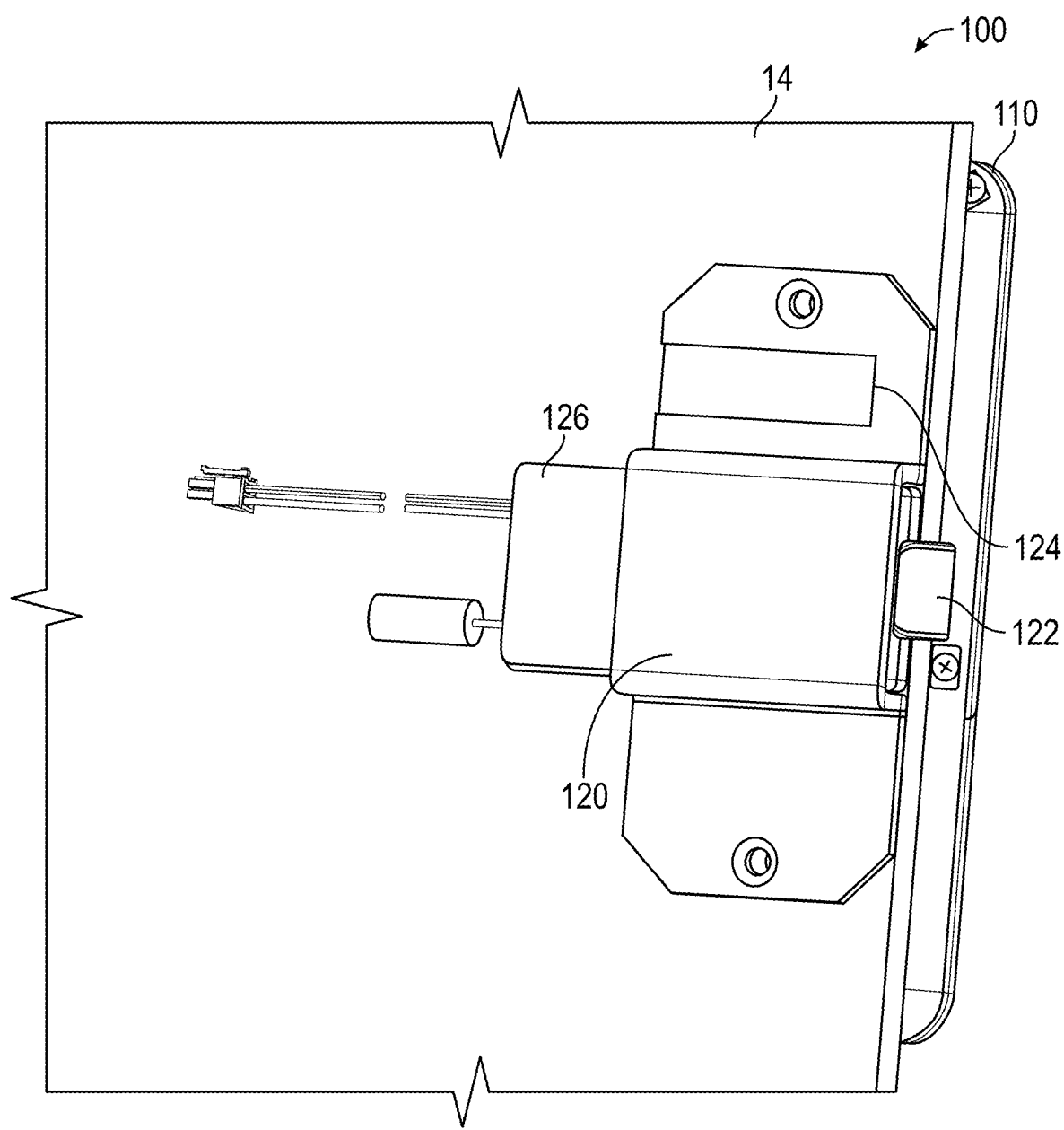
FIG. 3 is a reverse perspective view of the cabinet door of FIG. 2.

FIG. 2 is a perspective view of the cabinet 10 of FIG. 1 with a cabinet door 14 in an open position. FIG. 3 is a reverse perspective view of the cabinet door 14 of FIG. 2. With reference to FIGS. 2 and 3, the access control assembly 100 includes an interface module 110 and a latching module 120 coupled to the cabinet door 14.

In the depicted example, the interface module 110 can control the operation of the latching module 120, allowing a user to gain access to the cabinet volume 16. The interface module 110 can authenticate user inputs and send or display a message, or provide feedback or information, to the user. The interface module 110 can be mounted to an outer surface of the cabinet door 14. In some embodiments, the interface module 110 can be mounted to the cabinet door 14 using existing mounting points for conventional handles.

In the depicted example, the latching module 120 locks and unlocks the cabinet door 14 with the cabinet body 12. As illustrated, the latching module 120 is coupled to an inner surface of the cabinet door 14. In some embodiments, the latching module 120 is mounted opposite to the interface module 110. A mounting bracket 124 can secure the latching module 120 to the cabinet door 14. Optionally, the latching module 120 can be mounted to the cabinet door 14 using the existing mounting points for conventional handles. In some embodiments, the latching module 120 can be secured to the cabinet door 14 by the same fasteners securing the interface module 110.

In an unlocked state, the latching module 120 can allow the cabinet door 14 to be freely opened and closed. The latching module 120 can retract a latching member 122 to prevent the latching member 122 from engaging with the cabinet body 12. The latching member 122 can be moved or actuated by an actuator 126.

In a locked state, the latching module 120 can retain the cabinet door 14 in a closed position. The latching module 120 can extend the latching member 122 to engage against a portion of the cabinet body 12. The latching member 122 can engage against a frame or catch portion of the cabinet body 12. The latching member 122 can be moved or actuated by the actuator 126. As can be appreciated, the actuator 126 can be controlled by the interface module 110.

Figure 4:
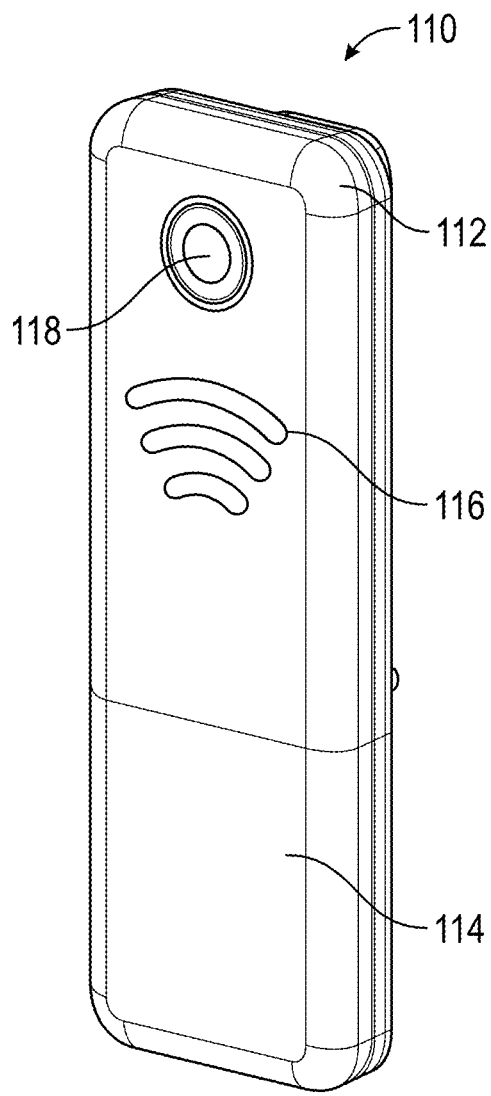
FIG. 4 is a perspective view of an interface module for use with the cabinet of FIG. 1, in accordance with various aspects of the present disclosure.
Figure 5:
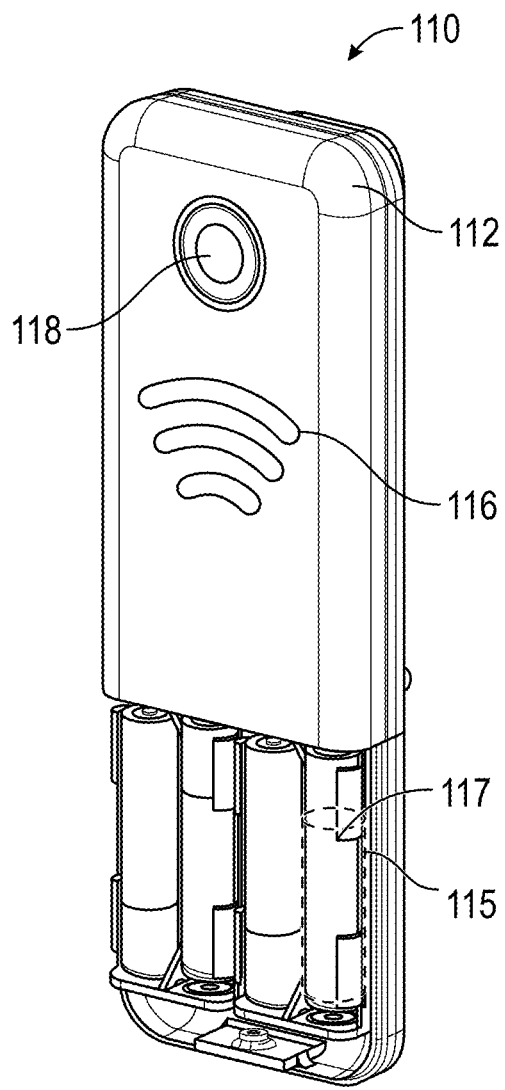
FIG. 5 is a perspective view of the interface module of FIG. 4 with a lower cover removed.
Figure 6:
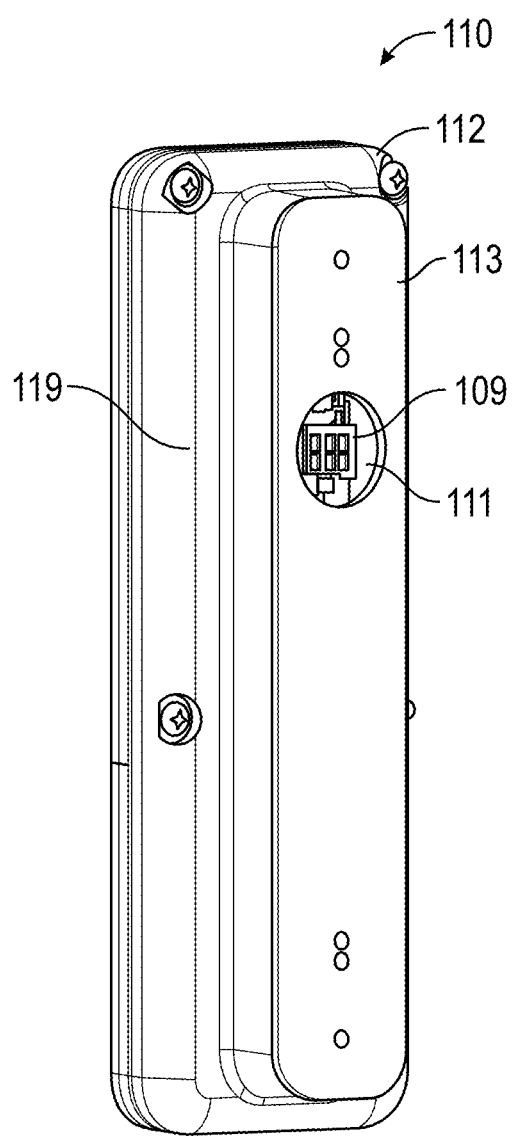
FIG. 6 is a reverse perspective view of the interface module of FIG. 4.

FIG. 4 is a perspective view of an interface module 110 for use with the cabinet 10 of FIG. 1, in accordance with various aspects of the present disclosure. FIG. 5 is a perspective view of the interface module 110 of FIG. 4 with a lower cover 114 removed. FIG. 6 is a reverse perspective view of the interface module 110 of FIG. 4. With reference to FIGS. 4-6, the interface module 110 can control the operation of the latching module 120 by preventing access by unauthorized users and permitting access for authorized users.

In the depicted example, the interface module 110 is operatively coupled to the latching module 120. In some embodiments, a connector 109 can provide an interface between the interface module 110 and the latching module 120. A cable can pass through a port 111 formed in the body 112 to engage with the connector 109. In some embodiments, the cable can pass through a hole in the cabinet door 14 to allow direct communication between the interface module 110 and the latching module 120 disposed on opposite sides of the cabinet door 14.

In some embodiments, the interface module 110 can function as an authentication device, can be used to direct and control access to the cabinet 10. In some embodiments, cabinets 10 can be accessed using a personal computer, a tablet computer, a smartphone, a barcode reader, and/or a biometric reader via the interface module 110. During operation, the interface module 110 can provide a plurality of user authentication methods (biometric, smartcard, password, barcode, ECG based wearable device, mobile phone, etc.), allowing the user to select one or more of the authentication methods. The selection may be a user specific configuration, site-specific configuration (e.g., all users at a given site will be authenticated according to the selected method(s)), or system-wide configuration (e.g., all users of the system will be authenticated according to the selected method(s)). The interface module 110 can include a sensing portion 116 to detect user inputs, such as biometrics, near field communication, smartcard, password, barcode, ECG based wearable device, mobile phone, etc. The interface module 110 can utilize any suitable personal area network (PAN) protocols, such as 802.15.4 or Bluetooth Low Energy, or other short-range compatible wireless communication protocol, to communicate with remote devices. In some embodiments, the use of PAN protocols can avoid integration with existing networks, simplifying installation.

Some embodiments provide that remote authentication methods can be implemented to allow a super user to grant remote authorization (e.g., if a user loses their badge or smart phone).

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computing or networked device, and the internet or including email transmissions and information recorded on websites and the like.

The user's authenticated identity can be transmitted to a server to request authorization to access a particular medication or item stored in a respective cabinet 10. Upon receiving authentication, the cabinet 10 can be identified and/or unlocked by retracting the latching member 122 of the latching module 120. In some embodiments, authentication can proceed in an offline mode, allowing the user to proceed without network connectivity. In some embodiments, the authentication device can provide an audible signal (for example from a piezo beeper) to indicate registration of user actions. Optionally, the interface module 110 can trace user access attempts, time of access, date of access, type of medication accessed, etc.

In some embodiments, the interface module 110 can include a position or acceleration sensor to determine if the cabinet door 14 is in an open or closed position. In some embodiments, the interface module 110 can either sense or record the position of the latching member 122 to determine if the latching member 122 is in a locked or unlocked position.

Sensors included in the interface module 110 may include one or more sensors to record, for example, environmental conditions and evidence related to attempts to divert or tamper with the contents of the cabinet. For example, a load sensor may comprise a load cell that can measure the mass of items contained in the cabinet, which can be used to estimate changes in item quantities. A temperature and humidity sensor may record inside and/or outside ambient temperature and humidity. A shock and vibration sensor may help to identify unauthorized access attempts to the cabinet using force. A tamper sensor may determine whether intrusion has occurred or if the cabinet has been removed from a fixture, for example if retaining screws, containers, covers, or other components of cabinet have been opened, unsealed, drilled, deformed, or otherwise tampered. For example, mechanical switches, anti-tamper films, photodiodes with reflective materials, infrared proximity sensors, and other devices may be used. A location sensor may include, for example, a global positioning system (GPS) radio to enable location history tracking. Alternatively or additionally, in some implementations, triangulation may be used to determine location, for example by using Wi-Fi or Bluetooth triangulation using known networks and/or hubs.

In some embodiments, the interface module 110 can include a status indicator 118. The status indicator 118 can display a plurality of colors at various intensities and flash patterns to provide a status of the interface module 110. As can be appreciated, the status indicator 118 can provide different visual indicators based on an identified user and workflow. For example, (i) during a medication loading workflow, the status indicator 118 can provide guidance to the user, (ii) if medication within a cabinet 10 is expired, the status indicator 118 can flash red, (iii) during a medication audit, the status indicator 118 can provide identifying information, and (iv) if the battery level of the interface module 110 is low, the status indicator 118 can provide a low battery signal. In some embodiments, the status indicator 118 includes one or more LED's driven by a FET based drive circuitry. Optionally, the status indicator 118 can be scanned by a handheld device to identify a status (including operating conditions or failure modes) of the storage system. The handheld device can utilize an optical scanner. In some embodiments, the interface module 110 can utilize an audio indicator to provide alerts regarding an open door or drawer.

In some embodiments, the interface module 110 can be powered by disposable or rechargeable batteries 117. As illustrated, the batteries 117 can be inserted into a battery compartment 115 defined at the front of the body 112. A lower cover 114 can cover the battery compartment 115. As can be appreciated, the battery compartment 115 can be accessed from the exterior of the cabinet 10, allowing the batteries 117 to be replaced without unlocking the cabinet 10 or requiring access to the interior of the cabinet 10. In contrast, conventional access control systems may have batteries that are accessed from the interior of a storage area, requiring conventional access control systems to unlock at a low state of charge to facilitate replacement of the batteries. Advantageously, by locating the battery compartment 115 at an exterior accessible location, the cabinet 10 can remain locked when the batteries are at a low state of charge or depleted, permitting the cabinet 10 to remain secured until the batteries 117 are changed.

In some embodiments, the interface module 110 can function as a physical contact point or handle for a user. As illustrated, the body 112 can be formed or shaped to allow a user to grasp the interface module 110 to open or close the cabinet door 14. The body 112 can similarly be shaped to allow a user to open or close a drawer.

In some embodiments, the body 112 can be mounted to an exterior surface of a cabinet door 14 or any other suitable surface. A handle portion 119 of the body 112 can provide a portion of the body 112 for a user to grasp. An extension portion 113 can extend from the handle portion 119 to space the handle portion 119 apart from a mounting surface. As can be appreciated, the extension portion 113 can be narrower to define a recessed area behind the handle portion 119 to allow a user's fingers to grasp the handle portion 119. The extension portion 113 of the body 112 can be coupled or otherwise disposed adjacent to the mounting surface.

In some embodiments, the interface module 110 can communicate with other interface modules 110. For example, the interface module 110 can communicate with each other to share inventory information, etc. In the depicted example, the interface module 110 can wirelessly communicate with other inventory control systems. Optionally, the interface module 110 can include a beacon for asset tracking, environmental sensing, tamper detection monitoring, real time and offline mode support, content identification and/or inventory tracking. The interface module 110 can include tamper resistance features.

In some embodiments, the interface module 110 can utilize one or more power conservation methods. Methods can include placing devices in various low power states to wake up periodically (wake up period), enabling radio communications, checking in with a gateway/hub for updates or to perform transactions. Power saving states can adjust device responsiveness in balance with power savings or low power states. The wake up period can be configured by the gateway/hub for devices based on system usage factors and user preferences. Power states can be adjusted based on user presence, such as if users are present, then devices are placed in more responsive states in anticipation of the system being used. If users are not present the devices are put in less responsive states to maximize power savings.

User presence can be detected in different ways, including users logging into the system or by occupancy sensors such as motion, radar, and proximity sensors. Occupancy sensors can be powered devices located in the storage area and interface to the gateway/hub. In some embodiments, users can input their office schedule into the system and power states can be adjusted based on this schedule. The system can utilize microphones with key word activation. In some embodiments, user actions such as button presses or system usage can wake up the device from deep sleep mode. Power states can be adjusted with machine learning algorithms running locally, on a hub, or on in the cloud.

In some embodiments, the system can harvest energy to increase the operational life of the system. For example, the system can include piezo transducers interfaced to buttons, and/or electromagnetic inductors to harvest energy from the opening or closing of the cabinet doors. Wireless energy can be harvested from RF sources.

Figure 7:
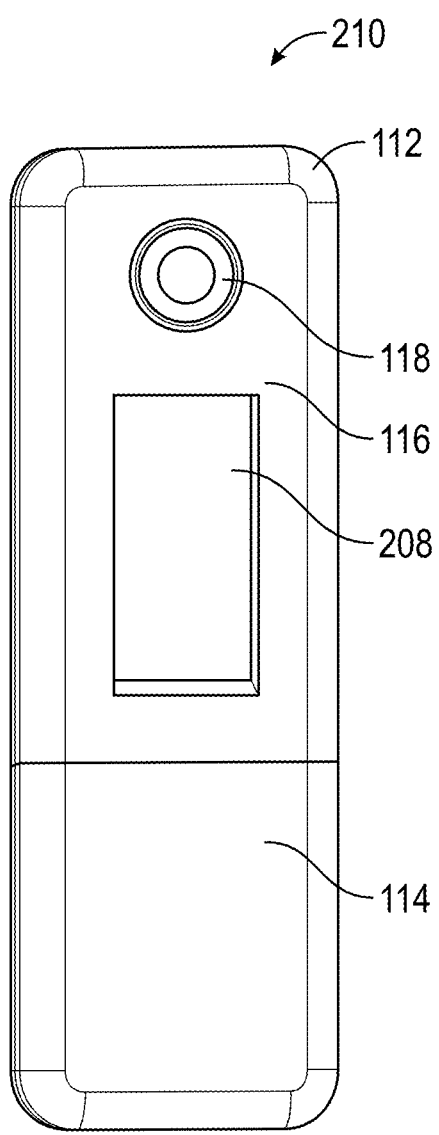
FIG. 7 is a front view of an interface module for use with the cabinet of FIG. 1, in accordance with various aspects of the present disclosure.

FIG. 7 is a front view of an interface module 210 for use with the cabinet 10 of FIG. 1, in accordance with various aspects of the present disclosure. Optionally, the interface module 210 can include a display 208, such as an e-ink display. The display 208 can display information about the contents of a respective cabinet. In some embodiments, the display 208 can display a barcode to provide information to a clinician or other personnel. Information can include the medication name, dosage, and/or expiration date. In some embodiments, the display can illustrate the tracking status of an associated medication, displaying information such as "loading dock" or "in transit." In some embodiments, the display 208 can display information collected from an environmental sensor, such as temperature of medication, monitor tamper evidence sensor signal, humidity, shock and/or vibration over time. The display for the interface module 210 can be controlled by a microcontroller included in housing. The display may be controlled by an interface module specific microcontroller. In some implementations, the control may be achieved using a control message from a remote server such as an inventory management server.

Figure 8:
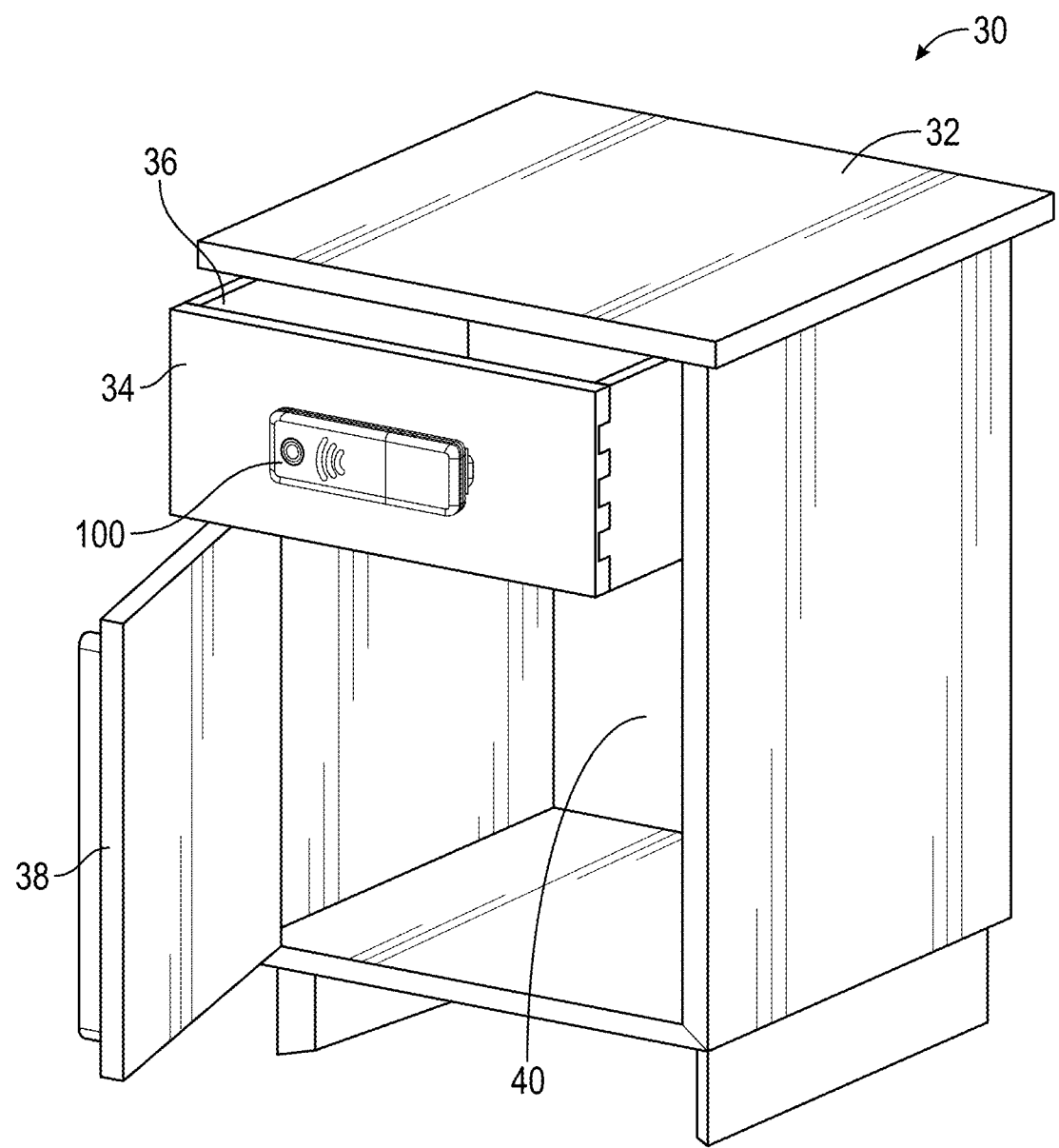
FIG. 8 is a perspective view of a drawer, in accordance with various aspects of the present disclosure.

FIG. 8 is a perspective view of a drawer 30, in accordance with various aspects of the present disclosure. With reference to FIG. 8, the drawer 30 in conjunction with the access control assembly 100 can provide secure item storage and retrieval.

As illustrated, the drawer 30 can allow for the storage of inventory within a drawer volume 36 defined by the drawer body 34. As can be appreciated, the drawer volume 36 can securely store items such as medication or other regulated products. In the depicted example, the drawer volume 36 can be accessed by sliding the drawer body 34 away from the drawer frame 32. Access to the drawer volume 36 and items stored therein can be prevented by closing the drawer body 34 within the drawer frame 32. The drawer body 34 can be movably coupled to the drawer frame 32 by one or more slides or rails.

As described herein, the drawer 30 can include an access control assembly 100 to control access into the drawer volume 36. The access control assembly 100 can lock the drawer body 34 to the drawer frame 32 to prevent access into the drawer volume 36 and items stored therein. During operation, the drawer body 34 can be unlocked or otherwise released upon authentication of a user. The access control assembly 100 can be mounted on a front face of the drawer body 34.

In some applications, the access control assembly 100 can be added or retrofitted to existing drawer bodies 34 to add access control to existing drawers 30. In some applications, drawers 30 can include the access control assembly 100.

The subject technology of secure medication storage is described herein. An access control module includes a latching module and an interface module. The latching module includes a latching member and a latch actuator configured to extend and retract the latching member. The interface module is coupled to the latching module. The interface module includes a module body defining a handle portion and an extension portion extending from the handle portion, an input device, and a controller. The controller is operatively coupled to the latch actuator and configured to authenticate the user input and control the latching member in response to the authenticated user input.

Access Control for a Refrigerator

Storage of refrigerated medicines and other healthcare items demand robust access controls and environment monitoring to prevent medicine spoilage, reduce overhead, and minimize costly diversion, theft, and other losses. Various systems may exist to address individual aspects of these demands. However, combining various disparate systems to address the multiple requirements of cold medicine storage may be costly, unwieldy, and difficult or impossible to implement in practice.

The subject technology provides secure access control and environmental monitoring via a smart latch to address the numerous requirements of refrigerated medicine and healthcare item dispensing in care facilities. The smart latch can be attached to existing refrigerators with hinged doors, thereby transforming the refrigerator into a network connected refrigerator with "smart" functionality including environment monitoring and access control. Smart functionality generally refers to processing capabilities and, for the smart latch, environment monitoring and access control processing capabilities. A smart device can have on-board memory or other storage capacity that can be written to and read from. The memory can contain one or more applications for implementing a particular function. The particular smart device may also contain an operating system and/or user interface. Some smart functionality may include wireless communications. For example, a smart device may include a transceiver for communicating through an electric field and/or magnetic field between the device and another entity such as a wireless terminal or information reader.

The smart latch may include various interfaces and devices to support other smart features such as environmental sensing, tamper detection, infrastructure and mesh networking, near-field communications, positional tracking, and user interfaces with audiovisual elements for inventory management, alerts, and user guidance. In this manner, the smart latch can interface and synchronize with a centralized back-end server to support inventory tracking, item condition tracking, and data collection for machine learning, as described in further detail in conjunction with FIGS. 10A and 10B below.

Figure 9A:
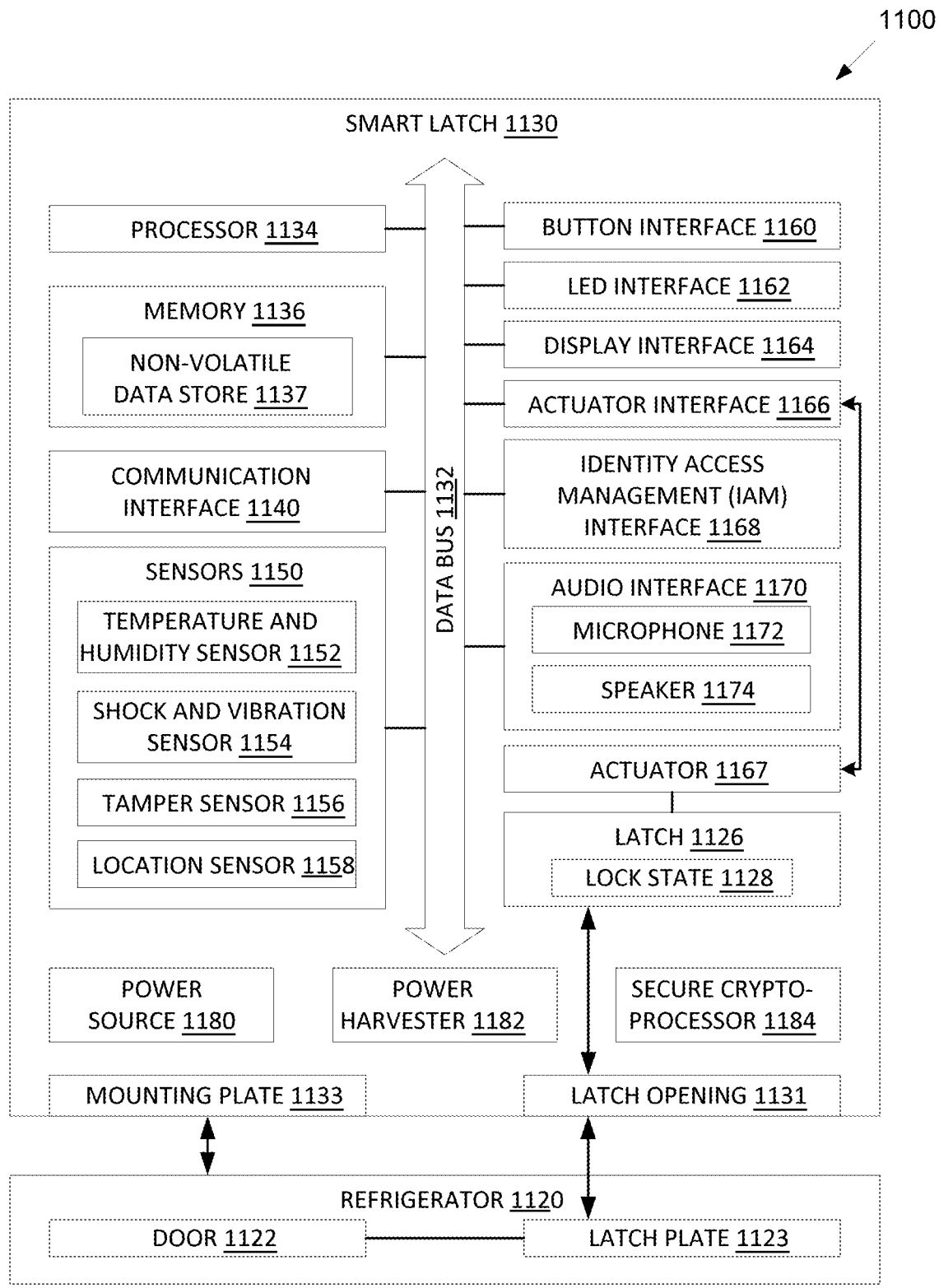
FIG. 9A depicts an example system including a smart latch to provide secure access control and temperature monitoring, according to various aspects of the subject technology.

FIG. 9A depicts an example system 1100 including smart latch 1130 to provide secure access control and temperature monitoring, according to various aspects of the subject technology. Refrigerator 1120 includes door 1122 and latch plate 1123. Smart latch 1130 includes latch 1126, latch opening 1131, data bus 1132, mounting plate 1133, processor 1134, memory 1136, communication interface 1140, sensors 1150, button interface 1160, LED interface 1162, display interface 1164, actuator interface 1166, actuator 1167, identity access management (IAM) interface 1168, audio interface 1170, power source 1180, power harvester 1182, and secure crypto-processor 1184. Latch 1126 includes lock state 1128. Memory 1136 includes non-volatile data store 1137. Sensors 1150 include temperature and humidity sensor 1152, shock and vibration sensor 1154, tamper sensor 1156, and location sensor 1158. Audio interface 1170 includes microphone 1172 and speaker 1174. The components included in smart latch 1130 are exemplary and other implementations may include a different configuration of components according to use case requirements, power consumption targets, clinical setting, and price point constraints.

Smart latch 1130 may include latch opening 1131, which allows latch 1126 to pass through a housing of smart latch 1130 to attach to latch plate 1123, as illustrated in greater detail in conjunction with FIG. 9B, FIG. 9C, and FIG. 9D below. Smart latch 1130 may include mounting plate 1133, which allows smart latch 1130 to mechanically attach to refrigerator 1120, for example via mounting bolts.

Smart latch 1130 may include processor 1134, which may correspond to any type of general or specialized processor, controller, integrated circuit, application specific integrated circuit (ASIC), field programmable gate array (FPGA), system-on-chip, or similar device, and may include hard-coded circuit elements, firmware, software, or any combination thereof to implement one or more of the specific smart latching features describe herein. Processor 1134 may communicate with other components of smart latch 1130 via data bus 1132, which may comprise one or more communication buses, such as parallel or serial buses.

Smart latch 1130 may include memory 1136, which may include volatile work memory as well as non-volatile data store 1137 for long term data storage. For example, non-volatile data storage 1137 may comprise flash memory or other memory that retains data after power source 1180 is unavailable. Non-volatile data store 1137 may include several data logs that record, for example, user authentication events, periodic sensor data, and local inventory of refrigerator 1120.

Communication interface 1140 may include one or more wireless radios to communicate with other devices and/or other smart latches. For example, communication interface 1140 may include one or more radios, scanners, or other devices that are compliant with Bluetooth, Bluetooth Low Energy, Near Field Communication (NFC), Wi-Fi, contactless Smartcards, Radio-Frequency identification, 1-D and 2-D barcodes, and other protocols.

Sensors 1150 may include one or more sensors to record, for example, environmental conditions and evidence related to attempts to divert or tamper with the contents of refrigerator 1120. For example, temperature and humidity sensor 1152 may record outside ambient temperature and humidity. In some implementations, temperature and humidity sensor 1152 may be augmented with inside temperature data received via communication interface 1140, for example from smart containers stored within refrigerator 1120. Shock and vibration sensor 1154 may help to determine whether an attempt to divert has occurred, or whether the contents of refrigerator 1120 were damaged during transport and handling. Tamper sensor 1156 may determine whether case intrusion has occurred, for example if retaining screws, latches, covers, or other components of smart latch 1130 have been opened, unsealed, drilled, deformed, or otherwise tampered. For example, mechanical switches, anti-tamper films, photodiodes with reflective materials, infrared proximity sensors, and other devices may be used. Location sensor 1158 may include, for example, a global positioning system (GPS) radio to enable location history tracking. Alternatively or additionally, in some implementations, triangulation may be used to determine location, for example by using Wi-Fi or Bluetooth triangulation using known networks and/or beacons. In combination with secure crypto-processor 1184, sensors 1150 may securely record real-time sensor data to comply with National Institutes of Standards and Technology (NIST) requirements. Sensors 1150 may include light sensor (not shown). Some items stored within the refrigerator 1120 may be light sensitive. The smart latch 1130 may assess a status of a light sensitive item based on levels recorded by sensors 1150.

Button interface 1160 may enable user input and selections on a user interface. For example, display interface 1164 may show a user interface directing the user to push specific buttons to update inventory, for example. Alternatively or additionally, display interface 1164 may provide a touchscreen panel to accept user input. In some implementations, user input may be received from a remote device, such as a tablet or smartphone, via communication interface 1140.

Light emitting diode (LED) interface 1162 may drive one or more multi-color LEDs or organic LEDs (OLEDs) for providing a quickly identifiable status indication. For example, LEDs may be driven at varied brightness, blinking patterns, and colors to indicate various states of smart latch 1130. In one configuration, solid red LEDs may indicate that sensors 1150 have recorded potentially unsafe environmental conditions for the contents of refrigerator 1120, such as temperature outside of a safety range for medicines, whereas solid green LEDs may indicate that sensors 1150 have recorded environmental conditions within safe parameters. Blinking green LEDs may indicate that an authorized user has submitted valid credentials for unlocking latch 1126 to access the contents of refrigerator 1120. Blinking red LEDs may indicate that tamper sensor 1156 and/or shock and vibration sensor 1154 have recorded an intrusion attempt, for example if a detected deformation, vibration or shock value exceeds a predetermined threshold. Blinking yellow LEDs may indicate that power source 1180 has crossed a low battery threshold and needs replacement. Blinking white LEDs may visually identify refrigerator 1120 to the user, allowing the user to readily identify refrigerator 1120 associated with a requested item in a pharmacy, stock room, or other facility. Further, in some implementations, the LED blinking patterns may be detected by a handheld scanner or another device to assist in inventory tracking and management.

Display interface 1164 may drive a display to show various user interfaces enabling a user to query the inventory of refrigerator 1120, to update the local inventory of refrigerator 1120 by adding or removing items, to query the condition of the items, to display remaining battery life, and to perform other management and status query operations. The user interfaces may utilize text and graphics such as icons, animations, and other elements. In some implementations, these user interfaces may additionally or alternatively be presented on a remote device, such as a tablet or smartphone. Display interface 1164 may drive an electronic ink (e-ink) display, a touchscreen liquid crystal display (LCD), an OLED, or another display type. The information may be presented on the display interface 1164 in human readable form (e.g., letters, numbers, or images) or machine-readable form (e.g., barcode, quick read code, standardized scan code form, or custom scan code form).

Actuator interface 1166 may trigger actuator 1167 to actuate latch 1126, thereby changing lock state 1128 from open to closed and vice versa. For example, latch 1126 may correspond to an electromechanical lock or an electromechanical latch. Actuator interface 1166 may also query latch 1126 to determine lock state 1128. In some implementations, a manual lock may be provided to manually lock and unlock latch 1126 without using actuator interface 1166. In this case, any manual locking or unlocking action may be recorded within an access log in non-volatile data store 1137. A manual lock may be useful to provide access to the contents of refrigerator 1120 when smart latch 1130 malfunctions or when power source 1180 is exhausted and no replacement is readily available.

Identity access management (IAM) interface 1168 may include one or more devices to enable a user to provide credentials for user authentication. For example, IAM interface 1168 may include one or more biometric scanners, such as a fingerprint sensor, an iris scanner, an electrocardiogram (ECG) reader such as a smartwatch, and a depth camera for facial recognition. IAM interface 1168 may also include smartcard readers or other devices to read a contactless smartcard or other unique identifier or token. In some implementations, IAM interface 1168 may use communication interface 1140 to utilize biometric scanners or readers present on a remote device, such as a tablet or smartphone. Accordingly, IAM interface 1168 may receive user credentials which can be validated in conjunction with secure crypto-processor 1184.

When multiple authentication methods are available in IAM interface 1168, then a particular authentication method may be automatically selected for authentication. For example, the authentication methods may be sorted according to security strength, and the methods with the highest security strength may be preferred for use. In some implementations, the user may select the preferred method of authentication. Further, a super user or a user with elevated privileges may manually authenticate a user, for example if the user misplaces his credentials.

Audio interface 1170 may include one or more audio devices, such as microphone 1172 and speaker 1174. Microphone 1172 may enable voice commands to be used instead of button interface 1160 or display interface 1164. Speaker 1174 may enable audio prompts, feedback, and alerts to be emitted. Speaker 1174 may comprise a piezoelectric speaker, a dynamic speaker, or another type of speaker. For example, different tones may be emitted from the piezoelectric speaker to indicate different states or user prompts.

Power source 1180 provides electrical power for the components of smart latch 1130. Power source 1180 may comprise a non-rechargeable battery, a rechargeable battery, a capacitor or super-capacitor, or another energy storage device. Power source 1180 may be user accessible and replaceable. To supplement or recharge power source 1180, power harvester 1182 may be used to receive power from external sources. For example, power harvester 1182 may receive wireless power through inductive coils or RF sources. Power harvester 1182 may also receive power through mechanical action, such as via piezo transducers interfaced to buttons connected to button interface 1160, or via electromagnetic induction induced by actuation movement of latch 1126. Power harvester 1182 may also receive power through direct wired connection, such as via universal serial bus (USB) charging cables, AC-DC chargers, or DC-DC chargers, which may be plugged into an external battery pack or wall mains voltage supply. In the event that power source 1180 is depleted, lock state 1128 may be maintained in its current state, whether closed or open, until power source 1180 is replaced or a manual lock is engaged, when made available.

To extend the operating time of power source 1180, various power management strategies may be utilized. For example, smart latch 1130 may be placed in a low power or sleep state when no activity is anticipated. When activity such as user interactions, periodic network updates, or sensor logging is necessary, smart latch 1130 may wake up to a normal operating mode, and return to the low power or sleep state once the activity is completed. The estimation of low activity may be based on network activity, user preferences, working schedules, or other factors. Smart latch 1130 may also wake up in response to an activation word or phrase via microphone 1172, a button press on button interface 1160, or a touch input from display interface 1164. In some implementations, sensors 1150 may include occupancy sensors which may be used to determine estimated activity levels. In some implementations, microphone 1172 may be used as an occupancy sensor. In some implementations, power management may be based on machine learning algorithms, as described in further detail below in FIG. 10A.

Secure crypto-processor 1184 may correspond to a trusted platform module (TPM) chip that stores public and private encryption keys for encrypting and decrypting data. For example, the public keys may include public keys of key pairs generated by authorized users, allowing each user to submit credentials encrypted by a respective private key for decrypting by secure crypto-processor 1184. Similarly, private keys specific to smart latch 1130 can be used to encrypt data before transmitting, storing, and exposing the data (e.g., to the outside world). In this manner, data travelling through data bus 1132 and stored in memory 1136, including non-volatile data store 1137, can be securely encrypted to protect against third party eavesdropping and modification. Encrypted data can also be more safely transmitted to the outside world, including over potentially insecure and untrusted networks.

With a block diagram overview of system 1100 now in place, it may be helpful to observe various perspective views of the components of system 1100. FIG. 9B depicts a side cutout perspective view of smart latch 1130, according to various aspects of the subject technology. Smart latch 1130 includes latch 1126, manual lock 1127, latch opening 1131, mounting plate 1133, communication interface 1140, display 1165, and actuator 1167.

Referring to FIG. 9A, various interfaces may drive or control the components of smart latch 1130. For example, display interface 1164 may drive display 1165, which may display status messages and various user interfaces for managing smart latch 1130 and the contents of refrigerator 1120. Actuator interface 1166 may instruct actuator 1167 to actuate latch 1126 through latch opening 1131. When actuator interface 1166 is unavailable, manual lock 1127 may be used to open or close latch 1126. Communication interface 1140 may be used to provide a repeater network for components inside an attached refrigerator, and may also be used as a node for nearby smart devices. The specific elements shown in smart latch 1130 are exemplary and any configuration of elements may be utilized according to use case requirements.

Figure 9B:
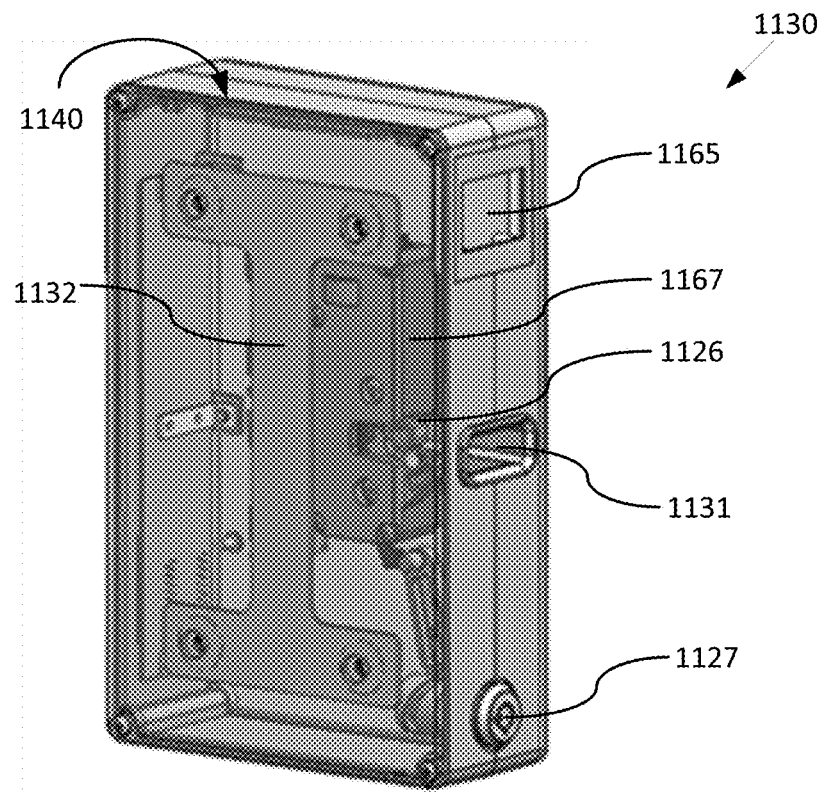
FIG. 9B and FIG. 9C depict side cutout perspective views of an example smart latch, according to various aspects of the subject technology.
Figure 9C:
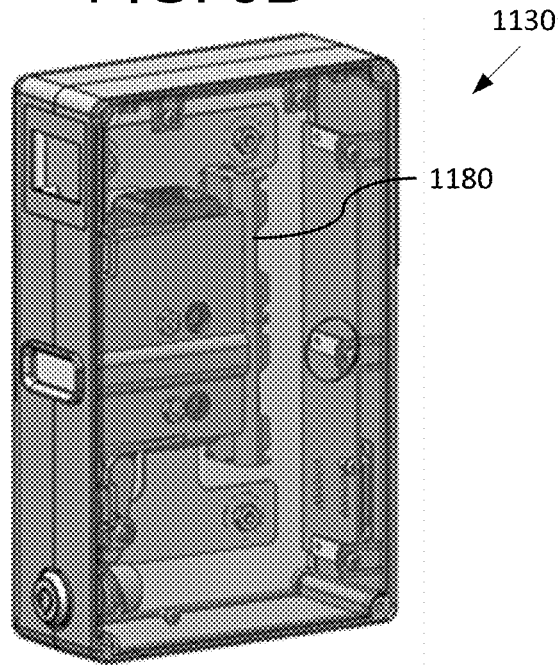

FIG. 9C depicts a side cutout perspective view of smart latch 1130, according to various aspects of the subject technology. Smart latch 1130 includes power source 1180. In some implementations, power source 1180 may be accessible from outside, such as via a battery door compartment, to allow easy replacement of power source 1180. In some implementations, a supplemental power source may be provided, such as a coin cell battery or super capacitor, for example to continuously power a real-time clock or other elements of smart latch 1130 while power source 1180 is exhausted or being replaced.

Figure 9D:
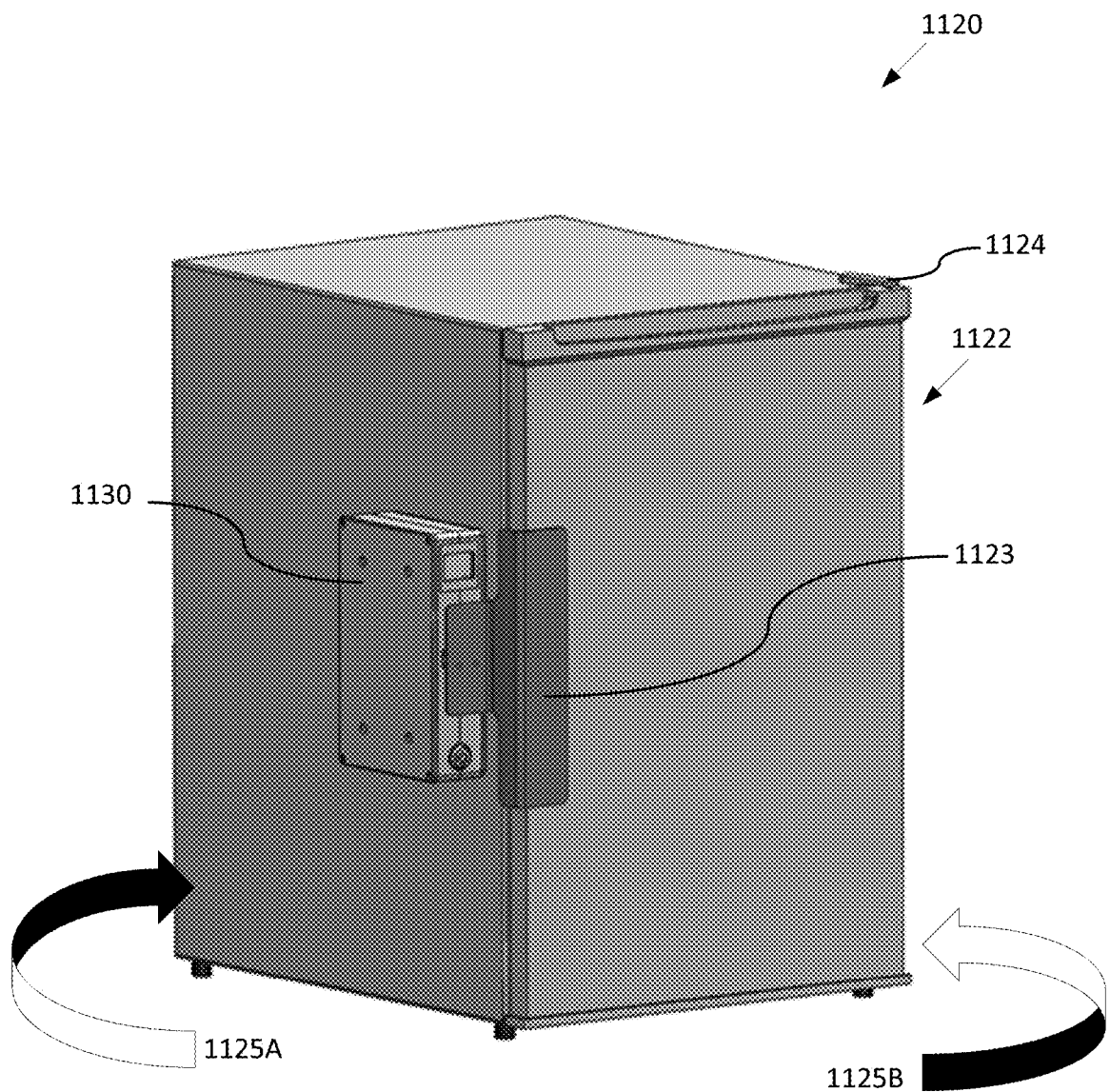
FIG. 9D depicts a perspective view of the example smart latch from FIG. 9B and FIG. 9C attached to an example refrigerator, according to various aspects of the subject technology.

FIG. 9D depicts a perspective view of smart latch 1130 attached to refrigerator 1120, according to various aspects of the subject technology. Refrigerator 1120 may correspond to an off-the-shelf refrigerator including door 1122 that opens and closes using hinge 1124. Referring to FIG. 9B, mounting plate 1133 of smart latch 1130 may be bolted to left side 1125A to attach smart latch 1130 to refrigerator 1120. In some implementations, the mounting plate 1133 may be placed on the left side or be repositionable by the end user to enable bolting to right side 1125B.

In the example shown in FIG. 9D, refrigerator 1120 is configured for left side opening. In other words, hinge 1124 is proximate to right side 1125B, whereas smart latch 1130 is attached to the opposite side, or left side 1125A. Smart latch 1130 is configured to latch into latch plate 1123, which may, for example, be mechanically attached to door 1122. However, other implementations may use right side opening, in which case the positions of hinge 1124, smart latch 1130 and latch plate 1123 may be switched from left side 1125A to right side 1125B and vice versa.

In some implementations, a remote device such as a tablet, smartphone, laptop, or other device may be used to interface with smart latch 1130. For example, the remote device may include an optical scanner that can read 1D or 2D barcodes and/or LED flashing patterns to receive data from smart latch 1130. The scanner may be used, for example, to identify smart latch 1130 for loading medications into refrigerator 1120. For example, smart latch 1130 may include an embedded unique identifier or serial number that can be transmitted using barcodes or LEDs. The remote device may contact a remote server, e.g. a pharmacy server, to determine, for example, a type and quantity of medications to be added refrigerator 1120. Pharmacy and local refrigerator inventories may also be automatically updated according to the expected change in contents of refrigerator 1120. In some implementations, the refrigerator may already be loaded with medications, and the user only needs to identify the correct refrigerator. For example, as discussed above, LED lights may blink on a specific smart latch to identify the refrigerator to the user. A similar process may be used for dispensing medications from refrigerator 1120.

The remote device may execute a local application downloaded from an application store, a corporate network, a website, or another distribution method. Alternatively, the remote device may execute a remote cloud-based application or a Software as a Service (SaaS) application. The application may allow communication with smart latches such as smart latch 1130. For example, the application may utilize radios that support various protocols such as Bluetooth, Bluetooth Low Energy, Near Field Communication (NFC), Wi-Fi, contactless smartcards, Radio-Frequency identification, and others.

When the remote device is connected to a network, such as via a Wi-Fi or cellular connection, smart latch 1130 may utilize the network to communicate and synchronize with a remote server, as described in further detail below in conjunction with FIG. 10A and FIG. 10B. Alternatively, when such a connection is not present, smart latch 1130 may utilize mobile mesh networking to use other smart latches as nodes to connect to the remote server. Further, smart latch 1130 may function as a wireless repeater to provide a network connection to smart containers within refrigerator 1120 and smart devices outside of refrigerator 1120. In some implementations, a cellular modem may be included within smart latch 1130 to provide a direct cellular connection to the remote server. However, to reduce implementation complexity and data network costs, it may be preferable to omit a cellular modem.

With an overview of the smart latch now in place, it may be helpful to observe the operation of multiple smart latches in an example networked environment. FIG. 10A depicts system 1200 including smart latches 1230A and 1230B in networks 1218 and 1219 to provide secure access control and environment monitoring of corresponding refrigerators 1220A and 1220B with inventory tracking 1215, item condition tracking 1216, and machine learning 1217, according to various aspects of the subject technology. FIG. 10A includes care facility 1210, server 1214, network 1218, and mobile mesh network 1219. Care facility 1210 includes patient room 1211, patient room 1212, smart device 1290C, and smart device 1290D. Patient room 1211 includes refrigerator 1220A and smart latch 1230A. Patient room 1212 includes refrigerator 1220B and smart latch 1230B. Server 1214 includes inventory tracking 1215, item condition tracking 1216, and machine learning 1217. Refrigerator 1220A includes smart device 1290A and smart device 1290B. Refrigerator 1220B includes smart device 1290E, smart device 1290F, and smart device 1290G. With respect to FIGS. 10A and 2B, smart latch 1230A and 1230B may correspond to smart latch 1130 from FIG. 9A-1D.

For example, starting at patient room 1212, a user may utilize a remote device, such as a tablet or smartphone, to request identification of a refrigerator having a requested item. The requested item may be stored in a container, for example smart devices 1290A-1290G that may comprise smart bins or other smart containers. The requested item may also be stored loose within refrigerator 1220A or 1220B.

Server 1214 may use inventory tracking 1215 to track an inventory of each uniquely identifiable smart latch and associated refrigerator. Server 1214 may connect to smart latches 1230A and 1230B via network 1218. Smart latches 1230A and 1230B may connect directly to an infrastructure network of care facility 1210 having access to a public network, such as network 1218, which may comprise the Internet. In some implementations, latches 1230A and 1230B may connect to a private local area network or other network before connecting to network 1218. In some implementations, a cellular router, hub, gateway, modem, or another network device may be provided in each smart latch 1230A and 1230B to provide a connection to network 1218. In this manner, the smart latches can be immediately deployed without requiring potentially costly and time consuming integration into existing information technology (IT) infrastructure at care facility 1210.

As shown in system 1200, each smart latch 1230A and 1230B may communicate with various smart containers and bins stored within each respective refrigerator 1220A and 1220B, for example by providing a wireless repeater network for connecting smart devices 1290A-1290G. Since the smart devices 1290A-1290G may be movable, e.g. moved inside and outside of refrigerators, from one refrigerator to another, and from one room to another, the smart devices 1290A-1290G may potentially lose connection to their initially paired smart latches 1230A and 1230B. In this case, the smart latches and the smart devices may provide mobile mesh network 1219, wherein each smart latch and smart device may function as a mesh node hop to facilitate a connection to network 1218. When a route to server 1214 is not immediately available, then a smart device may operate in an offline mode wherein inventory management is handled locally until a synchronization can occur with server 1214 when a connection route is available.

In some implementations, each smart latch may provide a user interface that accepts requests to identify the location of a particular item, such as medication or medical supplies. Additionally or alternatively, a user may use a remote device, such as a tablet or smartphone, to request identification of a refrigerator storing a particular item. The smart latch containing the item may identify itself to the user by outputting to an audiovisual element, such as by a blinking LED, emitting a sound, or a combination.

For example, the user may use a remote device to request location identification of a refrigerated drug. In some implementations, the remote device may contact a centralized service, such as server 1214, which in turn may query inventory tracking 1215 to find a refrigerator containing the drug that is closest to the user. To determine the smart latch/refrigerator that is closest the user, the position of the remote device and refrigerator may be detected using GPS and/or triangulated based on the availability of known network connections to the remote device and the smart latch/refrigerator.

In some implementations, the remote device may utilize mobile mesh network 1219 to find the closest smart latch/refrigerator containing the requested refrigerated drug. For example, each smart latch may query the inventory of the smart devices in the associated refrigerator to determine a local inventory. Further, each node in mobile mesh network 1219 may broadcast and propagate their own position and inventory to all other nodes, allowing a local cache of node locations and inventory to be stored by each node. In this manner, each node can quickly determine, from the local cache, the closest node where the requested refrigerated drug is possibly present. Since the local cache may be potentially out of date, a node may verify whether the refrigerated drug is actually still present by using mobile mesh network 1219 to send a query to the closest node. Once the closest node is determined, then a location of the closest node may be displayed on a map, e.g. on display 1165 or on a display of a remote device. If the refrigerated drug is not present, then the node may respond by providing the last authorized user and access time.

In this manner, devices connected to mobile mesh network 1219 may cooperatively determine that the requested drug is contained within smart device 1290B within refrigerator 1220A. Alternatively, server 1214 may utilize inventory tracking 1215 to make the same determination. As a result, server 1214 may instruct smart latch 1230A to enter into an alert or identification mode, wherein a LED flashes white to guide the user to refrigerator 1220A. The remote device may also display a map to guide the user to refrigerator 1220A. Further, any smart devices between the user and the destination, or refrigerator 1220A, may be directed to illuminate a path. For example, if the request is initiated at or near smart latch 1230B, then smart devices 1290C and 1290D may be illuminated to show a path to smart latch 1230A and refrigerator 1220A.

In some implementations, the alert emitted by smart latch 1230A may change depending on the user's proximity to refrigerator 1220A. For example, a LED on smart latch 1230A may flash when the user is within a proximity threshold, whereas a piezoelectric speaker on smart latch 1230A may beep when the user is outside of the proximity threshold. Once the door to refrigerator 1220A is opened, the specific container with the requested drug may also alert the user. For example, smart device 1290B may be directed to emit similar LED flashing alerts.

As shown in server 1214, inventory tracking 1215, item condition tracking 1216, and machine learning 1217 may be updated according to status information provided by each smart latch. For example, inventory tracking 1215, item condition tracking 1216, and machine learning 1217 may track the location, quantity, and condition of various medicines and healthcare items inside refrigerators 1220A and 1220B. Inventory tracking 1215 may be updated to reflect items added or removed from smart devices 1290A-1290G, for example by using the repeater networks provided by smart latches 1230A-1230B to query the inventory of the smart devices 1290A-1290G. Item condition tracking 1216 may be updated according to changing environmental conditions experienced by each smart device and smart latch. Machine learning 1217 may record device interactions and usage data for each smart latch 1230A-1230B. Referring to FIG. 9A, the information stored in server 1214 may be synchronized from data logs retrieved from non-volatile data store 1137.

At least a portion of the smart latch usage data may be processed by one or more machine learning algorithms to determine a power management profile that can be pushed back to smart latches 1230A-1230B for optimized power consumption. For example, the power management profile may define daily time periods when user interactions are infrequent. Smart latches 1230A-1230B may use this profile to transition the processor and other components to a low power idle or sleep mode during these daily time periods.

Each smart latch may also support real-time status reporting when a network connection route is available. For example, a client may query server 1214 for the status of a specific smart latch. Assuming that server 1214 can establish a network route to communicate with the requested smart latch, the smart latch may be queried for the requested status, such as environmental condition, tamper attempt history, or refrigerator inventory status, and the smart latch may respond by sending an encrypted message containing the requested status. Global searches may also be supported to query the status of multiple smart latches within a network. For example, one global search may request a list of refrigerators reporting internal temperatures above a threshold range, or a list of refrigerators sorted by internal temperatures.

Since the smart latches 1230A and 1230B have a built in display 1165 as shown in FIG. 9B, the display may continuously show item descriptions and temperature readings for associated refrigerator contents. Referring to FIG. 9A, by using a low power display technology such as e-ink for display interface 1164, battery life of power source 1180 may be extended. Accordingly, a user can quickly identify the contents of each refrigerator at a glance without actually opening the refrigerator. Further, the inside temperature of each refrigerator may be readily perceived and blinking LEDs or other audiovisual alerts may further bring attention to low battery levels or item condition deterioration, allowing remedial action to be carried out early before problems arise. Accordingly, refrigerated items can be kept at safe temperature ranges for smooth operation of care facility 1210.

Figure 10A:
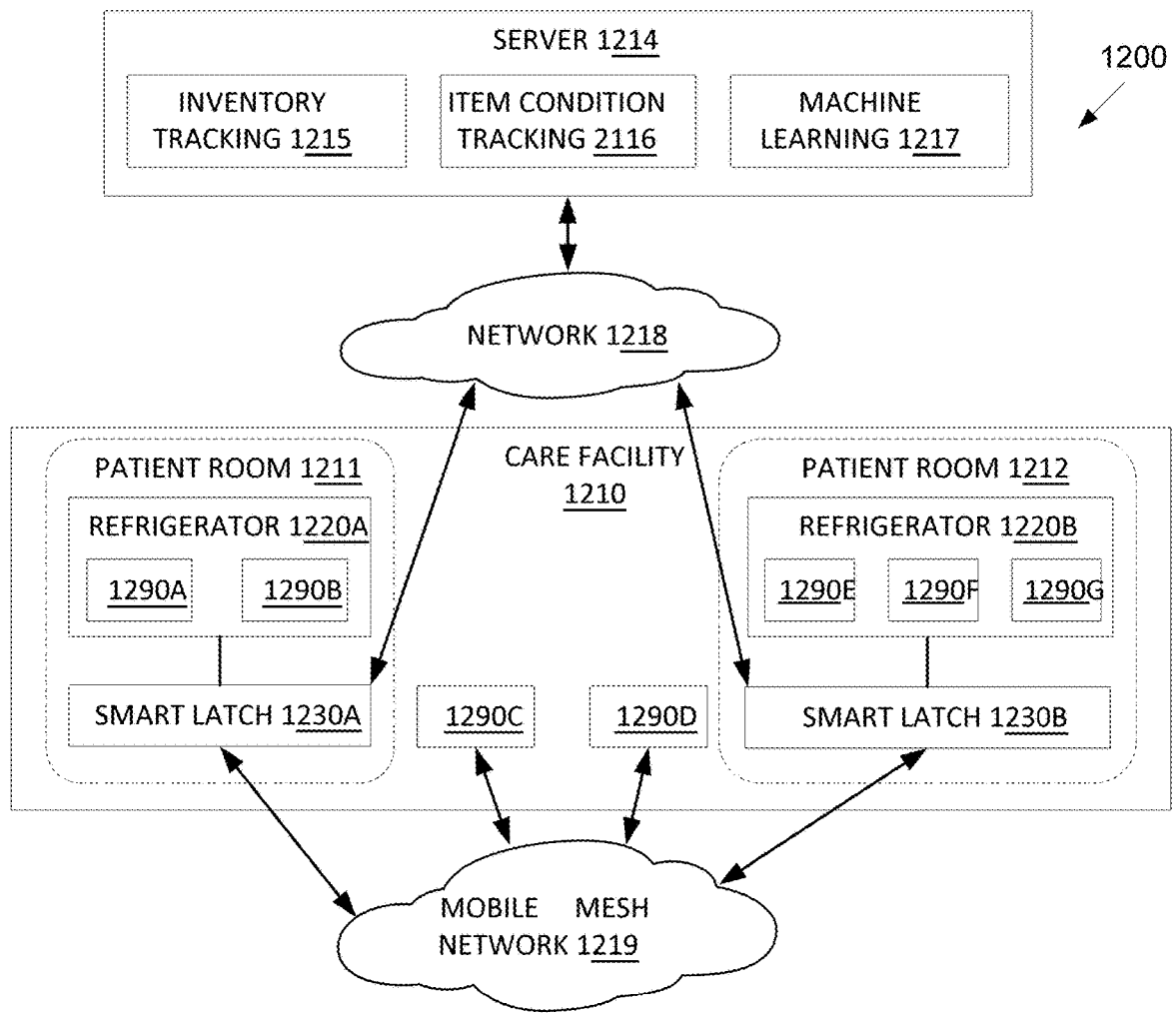
FIG. 10A depicts an example system including smart latches in an example network to provide secure access control and temperature monitoring, according to various aspects of the subject technology.
Figure 10B:
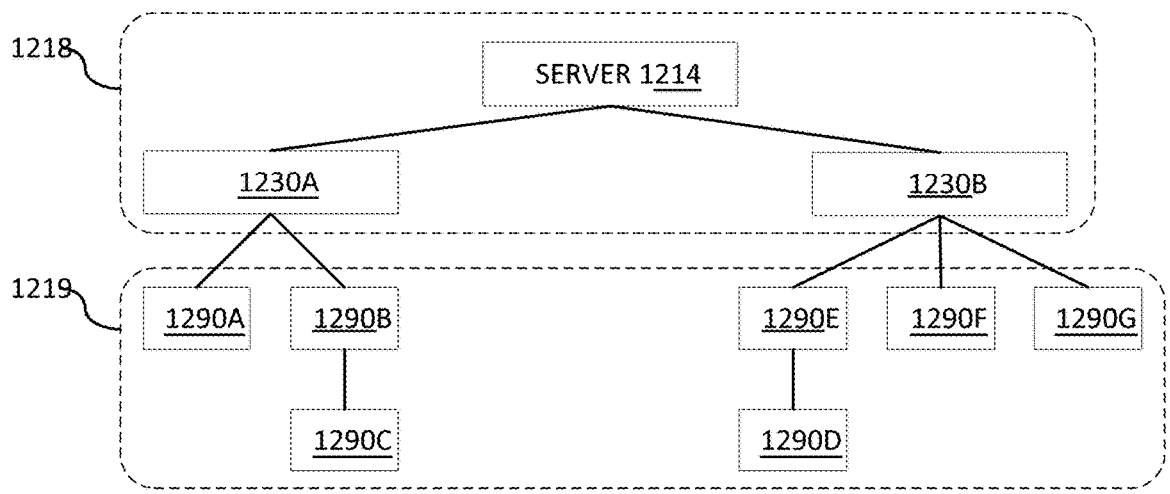
FIG. 10B depicts an example network topology diagram of the smart latches from FIG. 10A, according to various aspects of the subject technology.

FIG. 10B depicts an example network topology diagram of smart latches 1290A-1290B from FIG. 10A, according to various aspects of the subject technology. Network 1218 may correspond to a public network such as the Internet, and server 1214 may be connected to smart latches 1290A and 1190B. Mobile mesh network 1219 may correspond to an ad-hoc mobile mesh network, wherein each individual node, or smart devices 1230A-1230G may physically move and disconnect and reconnect with each other according to radio reception to form a mesh network. Smart latches 1230A-1230B may connect directly to server 1214 via network 1218, whereas smart devices 1290A-1290B may connect to a wireless repeater network provided by smart latch 1290A, and smart devices 1290E-1290G may connect to a wireless repeater network provided by smart latch 1290B. Smart devices 1290C and 1290D may connect to respective smart latches 1290A and 1290B using respective smart device 1290B and 1290E as an intermediary node. Thus, nodes can act as master nodes (e.g. server 1214), slave nodes (e.g. smart devices 1290A, 1290C, 1290D, 1290F, and 1290G), or hybrid master/slave nodes (e.g. smart latches 1230A, 1230B, and smart devices 1290B, 1290E).

FIG. 11 depicts various example user interfaces of a smart latch, according to various aspects of the subject technology. With respect to FIG. 11, display 1365A, display 1365B, and display 1365C may correspond to display 1165 from FIG. 9B. In some implementations, display 1365A-1365C may be shown on a remote device, such as a tablet, smartphone, laptop, or desktop computer.

Display 1365A shows a general purpose status screen, which may be shown by default when no user interaction is taking place. As shown in display 1365A, the status screen may include several informational fields, such as a description of contents and temperature, a battery level, a network status, and door open status. Referring to FIG. 9A, the description and temperature may be updated according to a local inventory stored in non-volatile data store 1137, which may be read from smart devices stored in the refrigerator. For example, referring to FIG. 9A and FIG. 10A, smart latch 1230A may read item description and temperature readings from smart devices 1290A and 1290B via a wireless repeater network provided by communication interface 1140. The battery level may be updated according to estimated charge detected for power source 1180. Network status may be updated according to the availability of connectable networks via communication interface 1140. The door open status may change depending on lock state 1128. While display 1365A-1365C illustrate text representations, it should be understood that graphical representations such as icons, bars, charts, animations, and other elements may be shown.

Once a user submits user credentials that are verified and authorized, the smart latch may open and the user may open the door, as indicated in display 1365B. In some implementations, a mechanical opener, spring, or other device may be used to automatically open and close the door.

The internal temperature of the refrigerator may begin to exceed safe temperature ranges, for example when a compressor failure occurs or the door is not securely shut. In this case, a warning message may be shown, as shown in display 1365C. The warnings may also be logged into a non-volatile data store, along with authentication and access logs that can identify the user who authorized refrigerator access at the time. Other alerts such as audible alarms or flashing LEDs may also be used to bring attention to the temperature warning.

Figure 12:
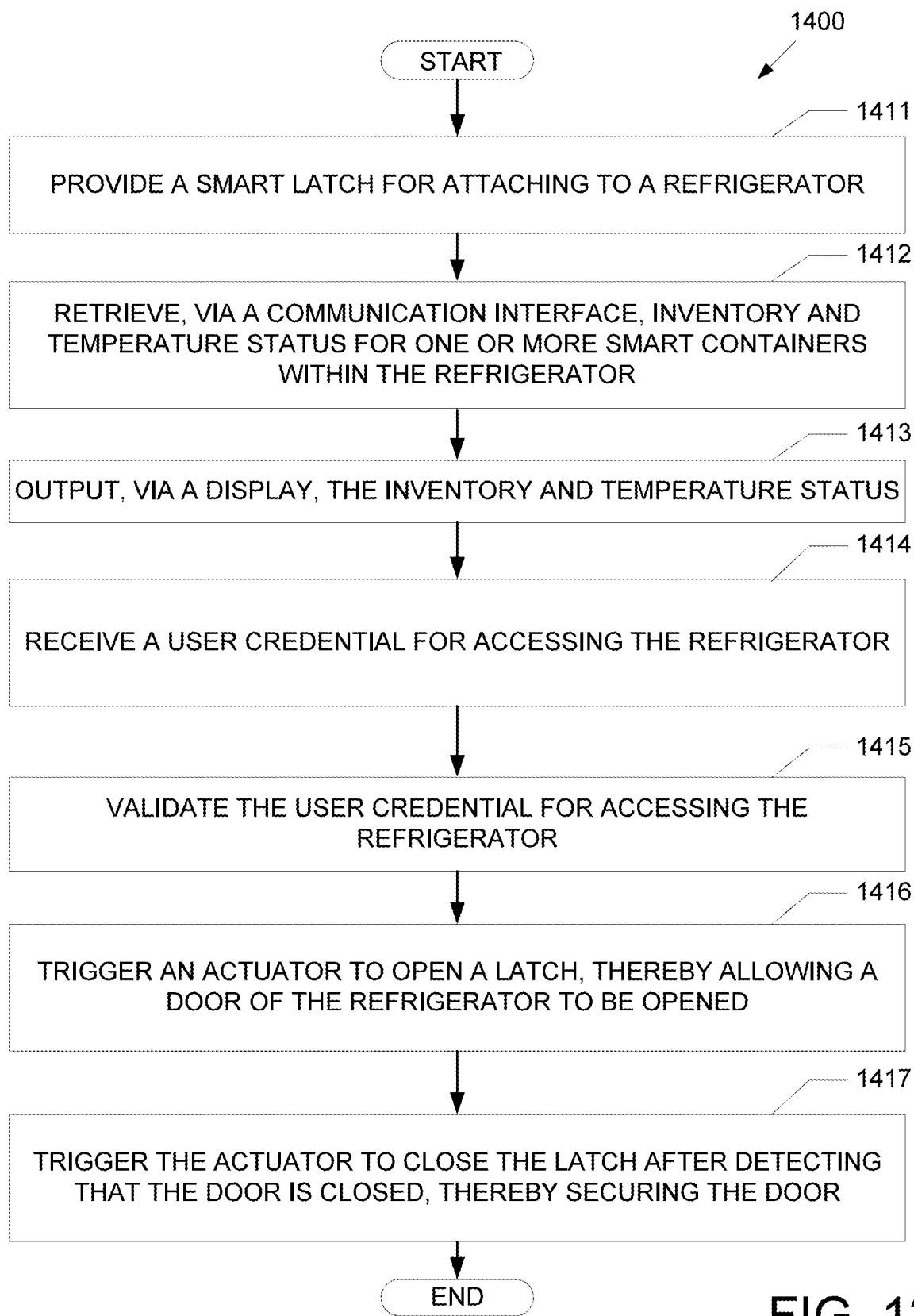
FIG. 12 depicts an example process for using a smart latch to provide secure access control and temperature monitoring, according to various aspects of the subject technology.

FIG. 12 depicts an example process 1400 for using a smart latch to provide secure access control and temperature monitoring, according to various aspects of the subject technology. For explanatory purposes, the various blocks of example process 1400 are described herein with reference to FIGS. 9A-11, and the components and/or processes described herein. The one or more of the blocks of process 1400 may be implemented, for example, by a computing device, including a processor and other components utilized by the device. In some implementations, one or more of the blocks may be implemented apart from other blocks, and by one or more different processors or devices. Further for explanatory purposes, the blocks of example process 1400 are described as occurring in serial, or linearly. However, multiple blocks of example process 1400 may occur in parallel. In addition, the blocks of example process 1400 need not be performed in the order shown and/or one or more of the blocks of example process 1400 need not be performed.

In the depicted example flow diagram, a smart latch is provided for attaching to a refrigerator (1411). Referring to FIG. 9D, this may correspond to providing smart latch 1130 for attaching to refrigerator 1120. More specifically, referring to FIG. 9B, mounting plate 1133 may be bolted to left side 1125A of refrigerator 1120. As discussed previously, when hinge 1124 is configured to open door 1122 from the right side, mounting plate 1133 may instead be bolted to right side 1125B. Further, latch plate 1123 may also be attached to refrigerator 1120, for example on door 1122.

Process 1400 may continue with retrieving, via a communication interface, inventory and temperature status for one or more smart containers within the refrigerator (1412). Referring to FIG. 9A and FIG. 10A, this may correspond to processor 1134 retrieving, via communication interface 1140, inventory and temperature status for smart devices 1290A and 1290B within refrigerator 1220A. For example, communication interface 1140 may function as a wireless repeater network, wherein smart devices 1290A and 1290B may connect and transmit the inventory and temperature status to smart latch 1230A.

Processor 1134 may continue to output, via a display, the inventory and temperature status (1413). For example, referring to FIG. 9A, FIG. 9B, and FIG. 11 processor 1134 may use display interface 1164 to output, via display 1165, the inventory and temperature status, which may appear similar to the user interface shown in display 1365A.

Processor 1134 may continue receiving a user credential for accessing the refrigerator (1414). For example, referring to FIG. 9A, processor 1134 may receive a user credential via IAM interface 1168. As discussed above, this may correspond to a unique identifier read from a smartcard or other token, or a biometric identifier.

Processor 1134 may continue to validate the user credential for accessing the refrigerator (1415). For example, referring to FIG. 9A, processor 1134 may utilize secure crypto-processor 1184 to verify that the user credential is valid against an encrypted authorized user database. Alternatively, referring to FIG. 10A, processor 1134 may utilize communication interface 1140 to verify the user credential against server 1214. In some implementations, the validation may further depend on the retrieved temperature status (1412). For example, if the temperature status exceeds a safe threshold range, then user access may be restricted to users with higher privilege levels. In this manner, potentially unsafe or spoiled medications may be kept safely locked until appropriate personnel can review the contents of the refrigerator.

Processor 1134 may continue to trigger an actuator to open a lock, thereby allowing a door of the refrigerator to be opened (1416). For example, referring to FIG. 9A, FIG. 9B, and FIG. 9D, processor 1134 may utilize actuator interface 1166 to trigger actuator 1167 to open latch 1126. Once lock state 1128 is set to open, then latch 1126 may no longer connect to latch plate 1123 and door 1122 may be manually opened by the user. Alternatively or additionally, a spring, a mechanical opener, or another assistive device may be used to open door 1122.

Processor 1134 may continue to trigger the actuator to close the latch after detecting that the door is closed, thereby securing the door (1417). For example, the user may manually close the door. In some implementations, the spring, mechanical opener, or other assistive device used to open the door (1416) may also be used to close the door, for example by triggering a closing of the door after a temperature change exceeds a threshold range, which may depend on the safe temperature range of items contained in the refrigerator. Referring to FIG. 9A, the door may be detected to be closed by using sensors 1150 and/or actuator interface 1166. Once the door is detected to be closed, referring to FIG. 9A, FIG. 9B and FIG. 9D, processor 1134 may utilize actuator interface 1166 to trigger actuator 1167 to close latch 1126 after door 1122 is closed.

In some implementations, processor 1134 may continue to synchronize the local inventory with a remote server via a communication interface. For example, referring to FIG. 9A and FIG. 10A, processor 1134 may synchronize the local inventory stored in non-volatile data store 1137 with inventory tracking 1215 stored on server 1214 via communication interface 1140. As discussed above, the local inventory may be received from smart devices within refrigerator 1120 that connect to a wireless repeater network provided by communication interface 1140. In some cases, this synchronization may be deferred until a stable network route to server 1214 is available. As discussed above, the smart latch may form mobile mesh network 1219 with other smart latches to improve network availability. The current location of the smart latch may also be conveyed to server 1214 based on triangulation using beacons or other location tracking methods.

In this manner, inventory tracking 1215 can be automatically updated with the current location and inventory for each refrigerator equipped with a smart latch, enabling detailed insight for medical supply restocking, loss prevention, and other management tasks. Similarly, item condition tracking 1216 may be updated to track environmental conditions (e.g. whether safe temperature ranges are maintained) and item quality, and machine learning 1217 may be updated with smart latch usage statistics to provide training data for power management profile generation.

Many aspects of the above-described example process 1400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 13:
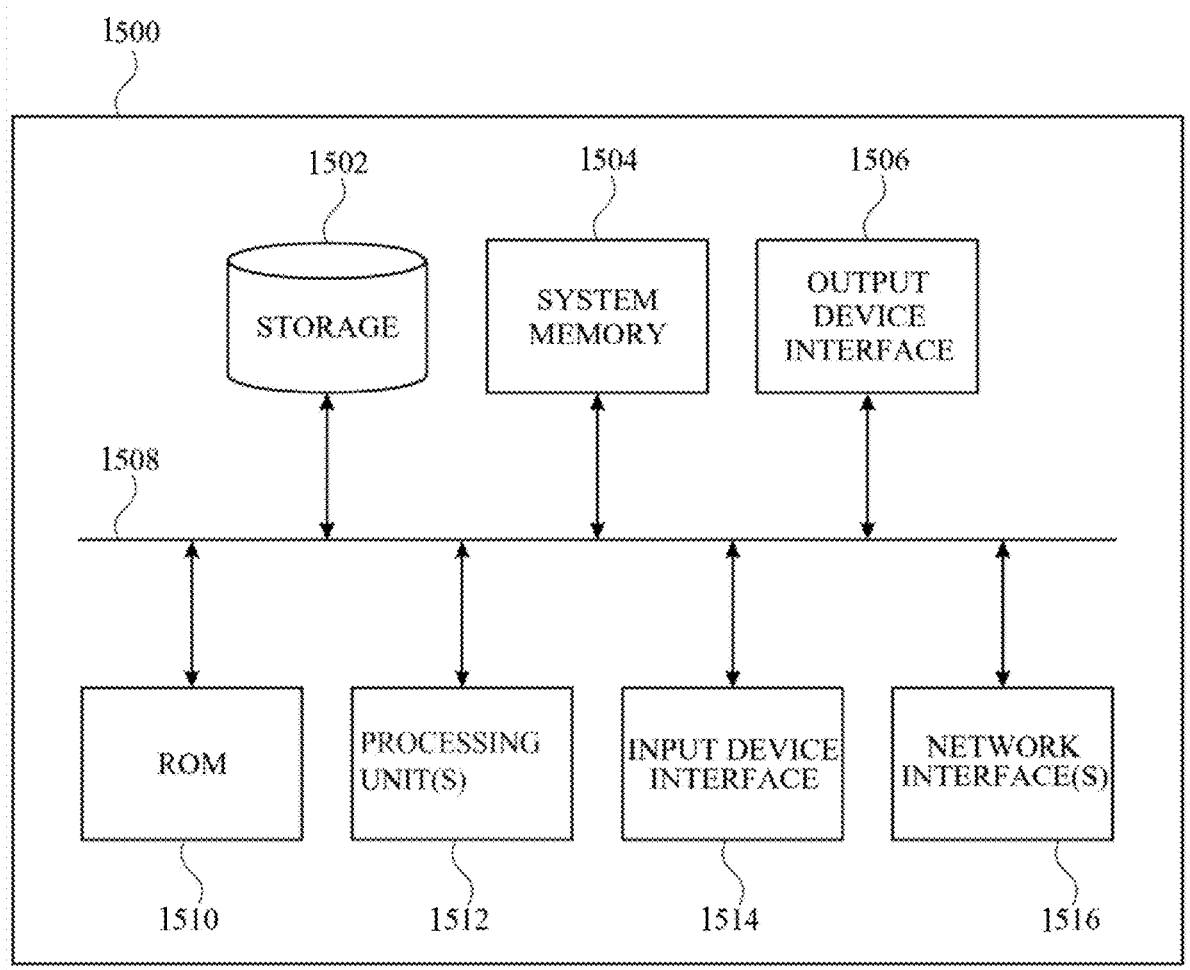
FIG. 13 is a conceptual diagram illustrating an example electronic system for providing a smart latch for automated inventory management, according to various aspects of the subject technology.

FIG. 13 is a conceptual diagram illustrating an example electronic system 1500 for providing a smart latch for automated inventory management, according to various aspects of the subject technology. Electronic system 1500 may be a computing device for execution of software associated with one or more portions or steps of process 1400, or components and processes provided by FIGS. 9A-12. Electronic system 1500 may be representative, in combination with the disclosure regarding FIGS. 9A-12, of the smart latch 1130 described above. In this regard, electronic system 1500 may be a microcomputer, personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 1500 may include various types of computer readable media and interfaces for various other types of computer readable media. In the depicted example, electronic system 1500 includes a bus 1508, processing unit(s) 1512, a system memory 1504, a read-only memory (ROM) 1510, a permanent storage device 1502, an input device interface 1514, an output device interface 1506, and one or more network interfaces 1516. In some implementations, electronic system 1500 may include or be integrated with other computing devices or circuitry for operation of the various components and processes previously described.

Bus 1508 collectively represents all system, peripheral, and chipset buses that communicatively connect the numerous internal devices of electronic system 1500. For instance, bus 1508 communicatively connects processing unit(s) 1512 with ROM 1510, system memory 1504, and permanent storage device 1502.

From these various memory units, processing unit(s) 1512 retrieves instructions to execute and data to process in order to execute the processes of the subject disclosure. The processing unit(s) can be a single processor or a multi-core processor in different implementations.

ROM 1510 stores static data and instructions that are needed by processing unit(s) 1512 and other modules of the electronic system. Permanent storage device 1502, on the other hand, is a read-and-write memory device. This device is a non-volatile memory unit that stores instructions and data even when electronic system 1500 is off. Some implementations of the subject disclosure use a mass-storage device (such as a magnetic or optical disk and its corresponding disk drive) as permanent storage device 1502.

Some implementations use a removable storage device (such as a floppy disk, flash drive, and its corresponding disk drive) as permanent storage device 1502. Like permanent storage device 1502, system memory 1504 is a read-and-write memory device. However, unlike storage device 1502, system memory 1504 is a volatile read-and-write memory, such a random access memory. System memory 1504 stores some of the instructions and data that the processor needs at runtime. In some implementations, the processes of the subject disclosure are stored in system memory 1504, permanent storage device 1502, and/or ROM 1510. From these various memory units, processing unit(s) 1512 retrieves instructions to execute and data to process in order to execute the processes of some implementations.

Bus 1508 also connects to input and output device interfaces 1514 and 1506. Input device interface 1514 enables the user to communicate information and select commands to the electronic system. Input devices used with input device interface 1514 include, e.g., alphanumeric keyboards and pointing devices (also called "cursor control devices"). Output device interfaces 1506 enables, e.g., the display of images generated by the electronic system 1500. Output devices used with output device interface 1506 include, e.g., printers and display devices, such as cathode ray tubes (CRT) or liquid crystal displays (LCD). Some implementations include devices such as a touchscreen that functions as both input and output devices.

Also, bus 1508 also couples electronic system 1500 to a network (not shown) through network interfaces 1516. Network interfaces 1516 may include, e.g., a wireless access point (e.g., Bluetooth or WiFi) or radio circuitry for connecting to a wireless access point. Network interfaces 1516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 1500 can be used in conjunction with the subject disclosure.

The subject technology provides secure access control and temperature monitoring of medicine and healthcare items stored within refrigerators in clinical settings. A method includes providing a smart latch for attaching to the refrigerator. The method also includes retrieving, via a communication interface, inventory and temperature status for one or more smart containers within the refrigerator. The method also includes outputting, via a display, the inventory and temperature status. The method also includes receiving a user credential for accessing the refrigerator. The method also includes validating the user credential for accessing the refrigerator. The method also includes triggering an actuator to open a latch, thereby allowing a door of the refrigerator to be opened. The method also includes triggering the actuator to close the latch after detecting that the door is closed, thereby securing the door.

Cabinet Smart Lock

One aspect of the disclosure relates to a system, device, and/or method that includes an enhanced lock for cabinet doors or drawers ("cabinet smart lock" or "smart lock"). The described smart lock system, devices, and corresponding methods facilitate securing medication inside cabinets and drawers in both acute and non-acute healthcare settings. The smart lock may be a wirelessly connected device with a locking mechanism to secure the medication, authentication capabilities to provide secure access and a user interfaces. The smart lock is configurable and users may be able to authenticate directly at the smart lock, or can use other methods such as logging onto a tablet or using a standalone authentication module to access the system or component connected thereto (e.g, a cabinet smart lock). According to various implementations, one or more user interfaces may include multi-color light emitting diodes (LEDs) and E-Ink display which are also configurable. Some implementations may include a machine learning (ML) inference and data analytics engine to dynamically adjust a power state of the smart lock to optimize power consumption on a smart lock device and/or system based on analysis of a lock's usage context. Some implementations may include a handheld device or mobile application that can scan multicolor LED and identify system status during manufacturing or field.

Existing solutions in non-acute space for securing medications involve off the shelf keyed or combination locks that are installed on the cabinets and drawers. Users use the same key or combination numbers to access medication, which is not traceable as to who accessed the cabinets. Wireless lock technologies that connect directly to a phone or mobile device are generally for personal use, but do not integrate into an enterprise level solution. The systems and method described herein includes an enterprise level solution that provides traceability and is integrated with medication workflows. The described systems and methods address these and other shortcomings of the existing lock technologies.

Figure 14:
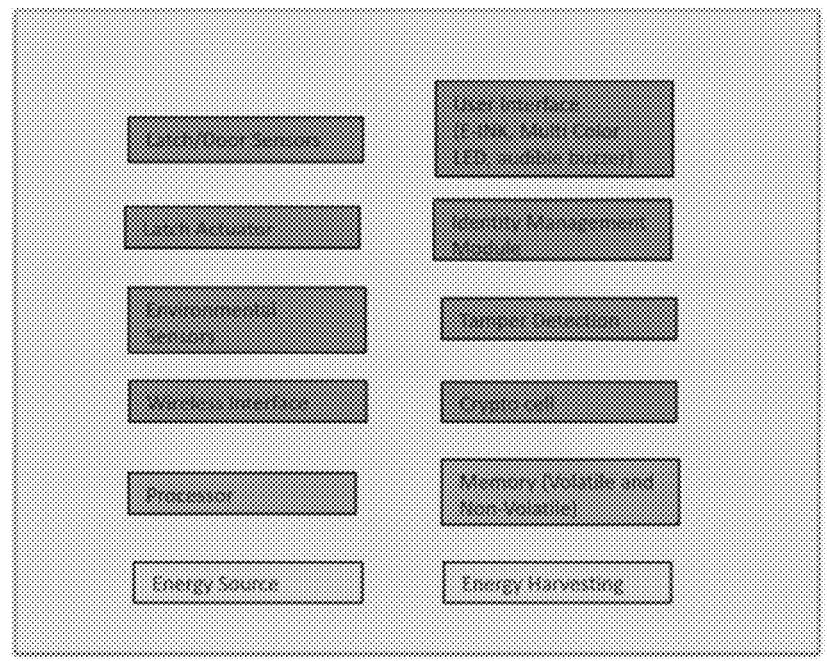
FIG. 14 depicts components of the disclosed smart lock system and/or device, according to some aspects of the subject technology.

Disclosed is a smart lock system, device, and methods used to secure cabinets and drawers in non-acute and acute healthcare settings:

FIG. 14 depicts components of the disclosed smart lock system and/or device, according to some aspects of the subject technology. In these examples, the system includes plurality of user interfaces, a server authorized actuator lock, lock and door sensors, identity authentication module, and other components that enable an enterprise solution for securing medication and guided loading of medication.

The E-ink user interface of the device may, in some implementations, display status of the smart lock system using icons such as battery level, network connectivity, status of the latch and door.

The E-ink user interface of the device may, in some implementations, in some implementations may display alerts such as expired medication, medication below par, tamper detection and etc.

The E-ink user interface of the device may, in some implementations, display information collected from the environmental sensor. Examples of such information collected include temperature of medication, monitor tamper evidence sensor signal, humidity, shock, and vibration over time.

The E-ink user interface of the device may, in some implementations, dynamically display information based on configuration associated with the user as to the contents of the display.

In some implementations, the multicolor LED user interface may act as a glanceable status indicator. The LED color, flash pattern, or intensity may be adjusted by the device (or in response to a control signal from a central control server) to indicate different status. The status may be based on user accessing the secure storage location, workflow, inventory level, or other detectable characteristic of the device or contents thereof.

Example 1: During medication loading workflow the LED lighting can guide the user to the medication at a glance.

Example 2: If the medications being secured by the smart lock has expired the LED can flash red.

Example 3: During medication audit the system may guide by lighting the LED's so the user can identify the med easily.

Example 4: If the battery level lower than threshold LED can flash in low intensity.

Example 5: LED color and flash pattern to indicate authorized user unlocked the latch.

Also provided is a computer implemented method by which a handheld device can scan the LED color, intensity and flash pattern and identify its status during manufacturing or in field. The computer-implemented method may be performed under control of one or more processing devices (e.g., CPUs or computer systems and/or devices).

The method may be implemented, in whole or in part, using an inspection equipment, a mobile application, and an optical reading device to read the multicolor visual indicator and analyze the reading to determine the failure modes and conditions on smart lock. Reading the indicator may include capturing an image of the LED. Reading the indicator may include capturing a series of images of the LED. The series may be captured for a period of time or number of frames identified using a configuration value. The series may be captured based on information encoded by the LEDs. For example, a preamble pattern or color may identify the start or end of a status sequence. When the device reads this pattern for a second time, the device may terminate reading and being the analysis of the captured image(s).

The authentication system may automatically determine a plurality of user authorization methods. The user may select one of the determined authorization methods to unlock the smart lock.

Features are also described for securely transmitting a user identity to a server and transmitting an authorization to unlock the smart lock. The authentication may, in some implementations, include reading data from a contactless smart card. In other implementations, it may use barcode, biometric identification, ECG based wearable device, a mobile phone, or a combination of the authorizations to request unlocking of a smart lock.

The authentication may include remote authentication. For example, users can enter credentials at tablet or PC or use a standalone authentication module to gain access to the smart lock or if the user loses their badge or smart phone a super user can provide remote authentication.

The sensor interface in an environment associated with a smart lock may monitor NIST traceable environmental sensor or tamper detection data in real time (e.g., within a threshold period of time from actual occurrence of the sensed environment condition or tamper event).

The systems or methods may generate an audible sound acknowledging user actions such as presenting badge to the smart lock or when an actuator command is been executed.

For example, in some implementation, a piezo beeper may be configured to emit different tones whereby each tone indicates a different action.

The communication architecture (CA) for the systems and methods, may include one or more of a plurality of personal area network (PAN) protocols such as (802.15.4/BLE) to communicate with the remote device.

The CA may be configured to detect beacon signals for asset tracking, provide environmental sensor and tamper detection monitoring, generate real time and offline mode support, or identify tote contents and track inventory. Because some health care supplies are temperature sensitive, if an environmental sensor determines that the temperature or humidity to which an item was exposed is outside an expected range, the system may dynamically adjust to alert or prevent dispensing of exposed items. Similarly, a sensitive item may have been tampered with. The system may direct storage or prevent distribution of such items until the integrity is confirmed. The confirmation may include an authorized user verifying the item before being eligible for dispensing and use in the healthcare facility.

According to various implementations, the smart lock CA can bypass set up and attachment to hospital IT resources. This can reduce implementation time and make it a drop ship model because of PAN protocol support.

A smart lock device may be configured to act as a companion device for devices placed inside the enclosure to bridge communications. Connected devices placed inside enclosures, such as refrigerators and metal cabinets, may have their radio signals attenuated and have difficulty communicating to hubs located further away. In these cases, another device such as the Smart lock is used as companion device to enable reliable communication to the hub/gateway. Smart lock when acting as a companion device can fill two roles: (i) a slave role communicating to the hub; (ii) a master role communicating to the devices behind the enclosure.

Figure 15:
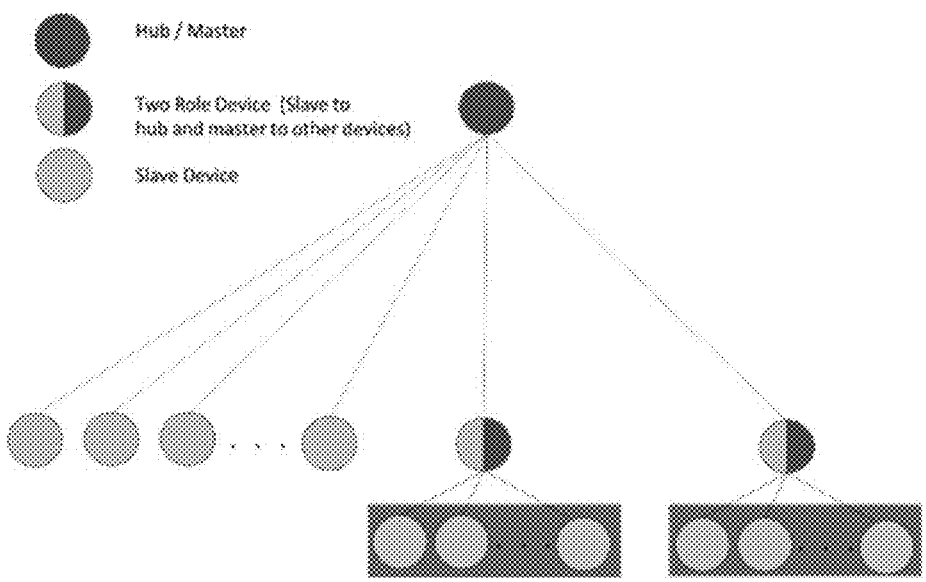
FIG. 15 depicts the disclosed devices arranged in a multi-level network hierarchy, in which the devices communicate back to the hub either directly or through another device.

FIG. 15 depicts the disclosed devices arranged in a multi-level network hierarchy, in which the devices communicate back to the hub either directly or through another device.

The power architecture of the smart lock device and/or system may include disposable batteries and in other implementations it may include rechargeable batteries. To improve efficiency of the devices by conserving power in battery operated devices, the power management module may operate based on system factors and user preference. The power management module may be implemented within a specific device to conserve resources of the device in which it is implemented. The power management module may be a central device configured to manage power for a group of devices in data communication therewith.

Devices may be placed in various low power states and may be configured to wake up periodically. The power management module may transmit a control signal to the devices in various low power states to wake up them up periodically (wake up period) and enable radio communications and check in with a gateway/hub for updates or to perform transactions.

The power saving states may be used to adjust device responsiveness versus power savings. The low power states and wake up period may be dynamically configured by the gateway/hub for devices based on system usage factors and user preferences.

Power states may be adjusted based on user presence. For example, if a sensor detects that users are present, the devices may be controlled to operate in more responsive states in anticipation of the system being used. If a sensor detects that users are not present or have left an area including one or more devices, the power management module may adjust devices within the area to operate in less responsive states, to maximize power savings.

User presence can detected in different ways including users logging into the system or by occupancy sensors such as motion, radar, and proximity sensors. Occupancy sensors are envisaged to be powered devices located in the health care service area (e.g., examination room, procedure room) and interface to the gateway/hub.

In some instances, users may provide an office schedule into the system and power states are adjusted based on this schedule (e.g., when an appointment is included for a time period on the schedule). The office schedule may indicate times when clinicians are working in the health care facility. Similar power adjustments may be controlled based on shifts when clinicians are active as indicated by the schedule.

Some instances may include microphones coupled with a speech detection system. The speech detection system may identify a key word to activate one or more device (e.g., adjust power state to an active/ready mode). In some implementations, a user action such as pushing a button or system usage factors such as user presence, may be used to wake up the device from a sleep mode.

In some instances power states may be adjusted by ML algorithms running on the hub/gateway and/or cloud. For example, historic patterns of usage may be analyzed to develop a model of power state activity that may be used to control one or more devices.

Features may also be included for harvesting energy using plurality of sources to increase smart lock operation life. In some instances uses piezo transducers interfaced to buttons or electromagnetic induction from lock actuator or drawer/door open and close action or wireless energy from RF sources to harvest energy.

The latch and door sensors included the system may include sensors to read the status of both the latch and door/drawer at all times. This capability enables workflow execution and also is used to detect tamper detection.

The following commentary and illustrations define a solution for dispensing items.

With reference to FIGS. 1-8 and FIG. 16 depicts a remote activated keyless lock that may be added to existing cabinet doors and/or existing cabinet drawers for controlled security, according to various aspects of the subject technology. FIGS. 17A and 17B depict a smart lock including a smart lock reader module, according to various aspects of the subject technology. In the depicted example, a smart lock reader module may be implemented as a mobile device that contains a PCBA, NFC reader, Multi Colored LEDs, Common Batteries, mounting features, e-ink display, biometric reader, audio buzzer, LED light pipe, barcode, snap-on cover in order to access the batteries.

Figure 18:
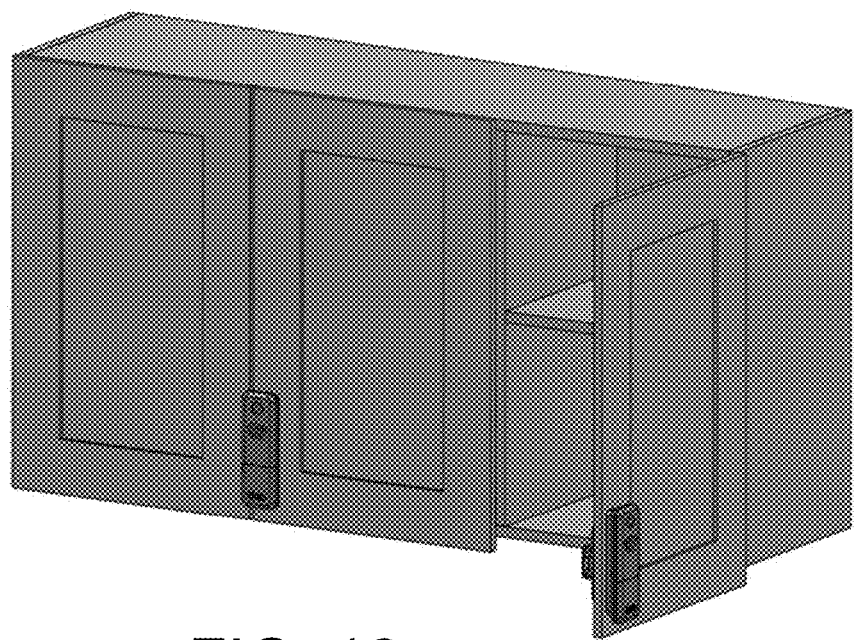
FIG. 18 depicts the smart lock reader module mounted on the external surface of a door or drawer using existing handle mounting holes, according to various aspects of the subject technology.
Figure 19:
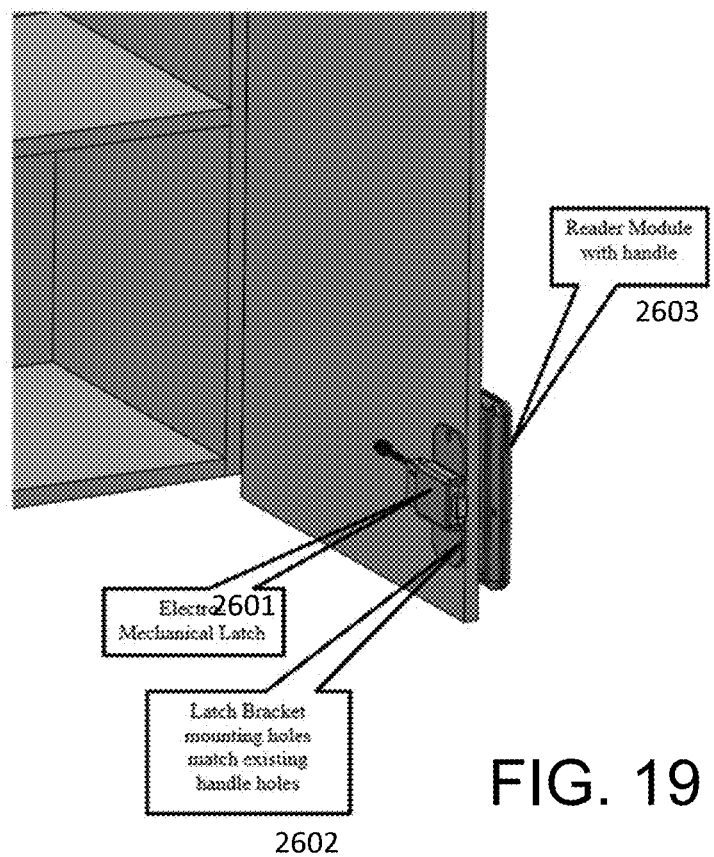
FIG. 19 depicts an electromechanical latch mounted to an interior surface of the door or drawer using a bracket, according to various aspects of the subject technology.

FIG. 18 depicts the smart lock reader module mounted on the external surface of a door or drawer using existing handle mounting holes, according to various aspects of the subject technology. FIG. 19 depicts an electromechanical latch 2601 mounted to an interior surface of the door or drawer using a bracket 2602, according to various aspects of the subject technology. The electromechanical latch is operably connected to the smart lock reader module 2603, which may electronically control the latch. The shape of the housing allows the user to grip the smart lock and use it has a door or drawer handle.

The screws that mount the bracket pass through the door or drawer and thread into the outer housing. When the batteries expire, the latch remains in the locked position and the batteries are replaced to continue operation. The LEDs indicate location. Audio indicator can alert an open door or drawer. A sensor is used to determine if the door(s) are in the closed or open position. A sensor is used to determine if the latch is locked or unlocked.

Figure 20:
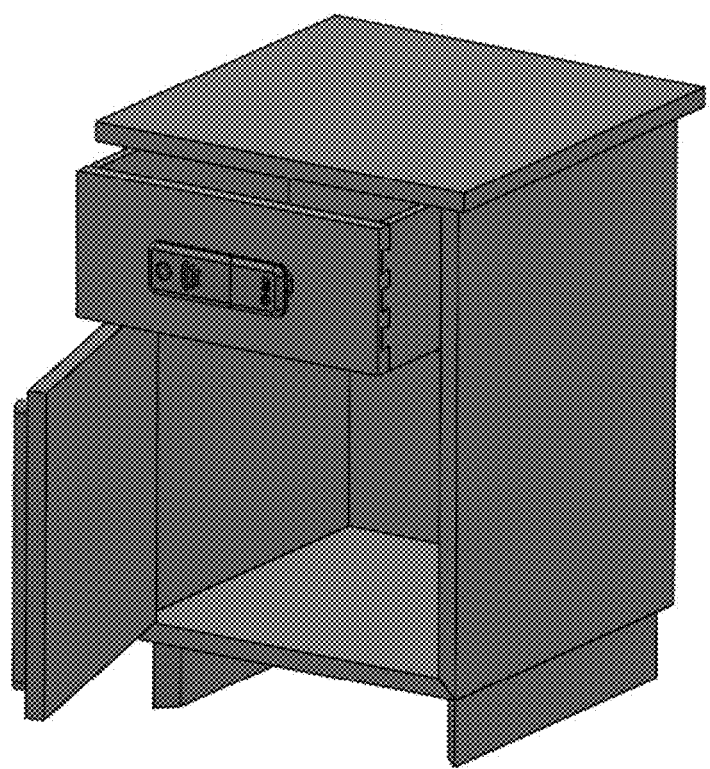
FIG. 20 depicts an example smart lock mounted to a cabinet drawer, according to various aspects of the subject technology.

The smart lock can communicate wirelessly to other devices. The smart lock units can have overlapping features, interlocks and to prevent diversion and indicate tamper evidence. FIG. 20 depicts an example smart lock mounted to a cabinet drawer, according to various aspects of the subject technology.

Connected Security Latch

Another aspect of the disclosure relates to a wireless activated smart remote manager (waSRM) system and methods that enables secured access to refrigerated medication that already exist in user healthcare settings. This solution provides safe and secured medication management with a focus on optimizing the existing user space and resources. The disclosed system and/or device includes a wireless latch, display and an enclosure that mounts effortlessly to a refrigerator. The system and/or device also includes a plurality of user interfaces along with actuator that unlock the waSRM with a secured authorization from a server. Optionally, the disclosed system, device, and/or method may also implement a machine learning (ML) inference and data analytics to optimize power consumption on waSRM based on its awareness of spatial context.

In the realm of regulated products in healthcare settings there is a need for space & cost optimized enterprise secured medication storage and dispensing solutions. In prior art, one solution is to use a remote manager with wired interfaces to a med station and proprietary message to unlock a refrigerator. The limitations are lock's proximity to med station and take up a significant space. In other implementations there are wireless activated refrigerator lock with temperature sensor but lack user interface, restricts just peer to peer protocol and no support for internet of things (IoT) architecture and hence can't aggregate and provide insight on data using a field hub or gateway. The subject technology involving a waSRM transforms the user experience with lot more insight on its usage using analytics and supports star, mesh, broadcast mode in a highly optimized enterprise medication management space. To the best ability of our knowledge the systems and methods we proposed using waSRM is unique and enables all the shortcomings of the prior art.

A system, device, and method associated with highly optimized medication storage and dispensing solutions in healthcare settings is disclosed.

The solution includes a waSRM with plurality of user interfaces, server authorized actuator lock, location tracking, and enables enterprise solution for inventory tracking.

According to various implementations, the system and/or device includes a processor, memory, input/output device, environmental sensor, tamper detection mechanism, and wireless interface. Other features include one or more of the following: E-ink display, microphone, buzzer and multicolor LED for user interface; identity authentication module (IAM) interface that enables plurality of user authentication methods such as smart card reader or biometric; FET based drive circuitry to drive the multicolor LED that supports plurality of colors, intensity and flash pattern to indicate glanceable status of the system; drive circuitry for E-ink user interface with plurality of views each configured to present the current state of the workflow; drive circuitry for piezo electric buzzer to provide audio feedback to the user; microphone interface circuitry for the user to provide wakeup words and or voice prompts; actuator latch drive circuitry and latch state read back methods; memory interface to store state and statistics of waSRM status; sensor interface to monitor tamper & environmental condition; and crypto and secure element interface to safely store public/private keys.

The disclosed system, device, and/or method may include an authentication system that automatically determines a plurality of user authorization methods. A user may then select one of the determined authorization methods to unlock the waSRM.

The disclosed system, device, and/or method may include a mechanism to securely transmit the user identity to the server and gets authorization to unlock the waSRM.

In some implementations, the authentication system may use contactless smart card. In some implementations, the authentication system may use a barcode, biometric identification, ECG based wearable device, or a mobile phone. The authentication method may include remote authentication. For example, if the user loses their badge or smart phone the super user can provide remote authentication.

The disclosed system, device, and/or method may include an optical or electromagnetic sensor interface that monitors for tamper detection on waSRM attached to refrigerator in real time.

The disclosed system, device, and/or method may include an environmental sensor interface system. In some implementations, the environmental sensor interface system may be capable of monitoring NIST traceable temperature sensors used for cold storage of vaccines.

In some implementations, the environmental sensor interface system may be capable of monitoring plurality of sensors including: temperature, humidity, vibration and acceleration of the waSRM.

The disclosed system, device, and/or method may include a mechanism by which an audible sound indicates user actions such as presenting badge to the waSRM or when an actuator command is been executed. In some implementations, the disclosed system, device, and/or method uses a piezo beeper with different tones to indicate different actions.

The disclosed system, device, and/or method may include a display user interface that functions as a glanceable status indicator and is configurable by the user. In some implementations, the display may provide detail information from the environmental sensors such as temperature and humidity.

Example 1: Display medication names and quantity that is been tracked.

Example 2: Display environmental sensor information inside and outside of the refrigerator.

Example 3: Display icons such as loading truck to indicate the status of the medication being tracked.

Example 4: Display battery level, network connectivity and status of the latch.

The disclosed system, device, and/or method may include a multicolor LED user interface. In some implementations, the LED user interface functions as a glanceable status indicator. The LED color, flash pattern and intensity may indicate different status based on user accessing the secure storage location and workflow.

Example 1: During medication loading workflow the led lighting can guide the user to the medication at a glance.

Example 2: If the medication in the slimline bin expired the LED can flash red.

Example 3: During medication audit the system may guide by lighting the LED's so the user can identify the med easily.

Example 4: If the battery level lower than threshold led can flash.

The disclosed system, device, and/or method may include a communication architecture (CA). In some implementations, the CA may be configured with a plurality of PAN protocols such as (802.15.4/BLE) to talk to a remote device. A method that utilizes the CA may include one or more of the following features: beacon for asset tracking; real time and offline mode support. In some implementations, the waSRM (e.g., using CA) may bypass hospital IT, thereby reducing implementation time (e.g., implementing a drop ship model based on PAN protocol support).

The system and/or method implementing communication architecture (CA) may support an offline mode. When a network connection to the field hub or gateway is lost the waSRM may still allow the user to continue with their action, and the system may store and forward the actions when the network is restored.

In some implementations, the waSRM is configured to broadcast beacons to the remote host with the medication information for asset tracking. In some implementations, users may also read the beacons using a mobile device such as a phone or tablet.

In some implementations, the waSRM may be configured as a companion device for devices placed inside the enclosure to bridge communications. Connected devices placed inside enclosures, such as refrigerators and metal cabinets, may have their radio signals attenuated and have difficulty communicating to hubs located further away. In these cases another device such as waSRM is used as companion device to enable reliable communication to the hub/gateway. smart bin when acting as a companion device may play two roles: (1) A slave role communicating to the hub; and (2) A master role communicating to the devices behind the enclosure. With brief reference to FIG. 15, This may create a multi-level network hierarchy in the network of devices all communicating back to the hub either directly or through another device.

In some implementations, the disclosed system and/or methods may include power architecture (PA) that utilizes disposable batteries or, in other implementations, the power architecture may implement rechargeable battery or a supercapacitor as an energy source for each waSRM.

The PA may use wireless power transfer to access the waSRM.

The system and/or device may be charged using one or more of a plurality of wireless energy sources. In some implementations, the PA is configured to utilize far field (such as WiFi, UHF) wireless power transfer are used as energy source to access the waSRM.

The disclosed system, device, and/or method may be configured to conserve power in battery operated devices based on system factors and user preference. A corresponding method may include placing devices in low power states (ranging from system off state to various levels of sleep state) and waking up the devices periodically (wake up period) to enable radio communications and to check in with a gateway/hub for updates or to perform transactions.

The low power state and wake up period may be configured by the gateway/hub for devices based on system usage factors and user preferences.

In some implementations, the system, device, and/or method uses environmental sensors such as occupancy sensors. In some implementations, the system, device, and/or method may use a microphone with key word activation or system usage factors such as office schedule to wake up the device from deep sleep mode.

In some implementations, the system, device, and/or method may be configured for energy harvesting using a plurality of sources to increase waSRM operation life. In some implementations, the system, device, and/or method may utilize electromagnetic induction from lock actuator action or wireless energy from RF sources to harvest energy.

Figures 21A, 21B:
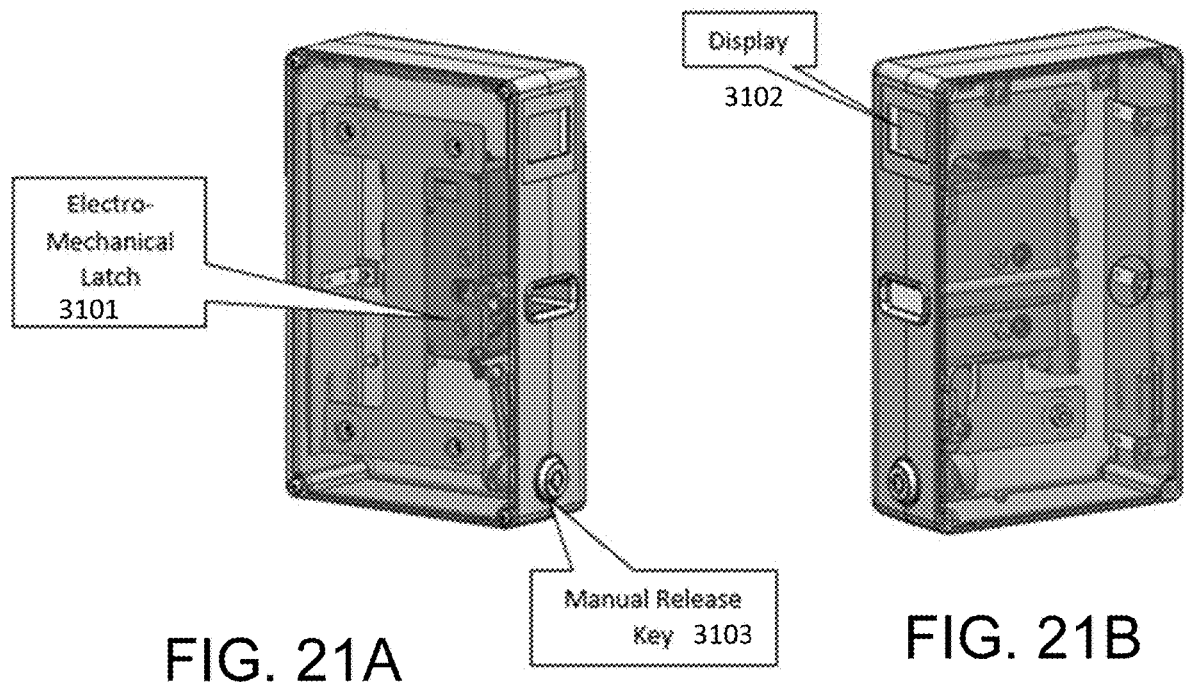
FIGS. 21A and 21B depict a cut-away view of an example IOT (Internet-of-things) smartlock reader module (SRM), according to various aspects of the subject technology.

FIGS. 21A and 21B depict a cut-away view of an example IOT (Internet-of-things) smartlock reader module (SRM), according to various aspects of the subject technology. According to some implementations, the disclosed IOT SRM includes a device that may be attached to a refrigerator, as described with respect to FIGS. 9A-13. In this regard, the IOT SRM may incorporate an electro-mechanical lock 3101 for secured access to the refrigerator. The IOT SRM may include an (e.g. e-ink) display 3102, LED indicator, Temperature readout, and common batteries for ease of replacement. The JOT SRM may be configured to communicate wirelessly with other devices. The JOT SRM may include a manual release key 3103 to release lock 3101 by mechanical means (e.g., when power has been removed from the lock).

Figure 22:
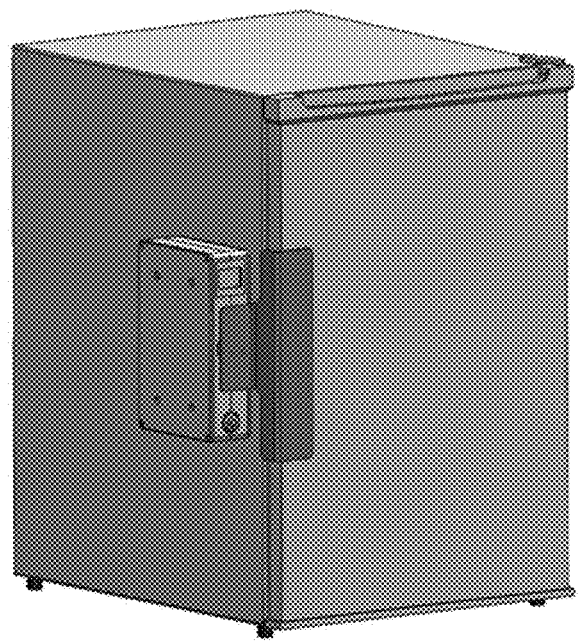
FIG. 22 depicts an example IOT SRM mounted on the exterior surface of a refrigerator, according to various aspects of the subject technology.

FIG. 22 depicts an example IOT SRM mounted on the exterior surface of a refrigerator, according to various aspects of the subject technology. The refrigerator may include an off-the-shelf "dorm" style refrigerator for controlled security. The IOT SRM may include a repeater to aid in the communication of IOT devices within the refrigerator. The IOT SRM may include overlapping features, interlocks and materials to indicate tamper evidence. The JOT SRM may include a key lock for manual release.

Further Implementations

Further features are described herein for facilitating rapid deployment of a variety of devices within a clinical setting. The clinical settings for the described features may include a non-acute health service facility such as a doctor's office, pharmacy clinic, outpatient clinic, institutional infirmary (e.g., school nurse's office), hospital, or the like. In such settings, the physical resources available, including space and network coverage, may be limited. Furthermore, such facilities may face limited resources for installing and managing critical dispensing devices. The features described may be used independently or integrated in various combinations to provide efficient and secure dispensing systems compatible with dynamic clinical needs.

Secure Tote

The subject technology may relate to a smart tote system and method for securely transporting controlled and non-controlled medication in acute or non-acute healthcare settings.

The disclosed system enables evidence for real time location tracking, chain of custody, environmental state of the transport, and automatic inventory tracking and loading of medication both at rest and transit. The system may include a plurality of user interfaces along with actuator that unlock the tote with a secured authorization from a server. The system and/or method may implement a machine learning (ML) inference and data analytics to optimize power consumption (e.g., on the smart tote device) based on its awareness of spatial context. The system and/or method may further include a handheld device or mobile application that can scan multicolor led and identify system status during manufacturing or field.

Existing medication transport solutions do not provide any data or evidence on the environmental state of the transport (temperature, humidity, shock, vibration), security, real time location, or assist the end user in automatic inventory tracking and loading of assets. Some solutions (e.g., involving a tote that transports medication from a central pharmacy or a wholesale distribution to a clinic) use zip ties to secure the tote and provide no evidence to real time location, security, and environmental condition of the transport. Few implementations provide silo solutions which just address the cold chain tracking of medications that requires temperature evidence. The proposed systems and methods include an enterprise solution that addresses the above short comings using a smart tote of the subject technology.

Accordingly, systems and methods associated with secured medication transport solutions in non-acute and acute healthcare settings is disclosed herein.

The disclosed solution may include a smart tote with plurality of user interfaces, one or more server authorized actuator locks, one or more environmental sensors to monitor the state of transport, and may include location tracking and evidence of custody and enables enterprise solution for inventory tracking and guided loading of medication.

According to various implementations, the system comprises a processor, memory, input/output device, environmental sensor, tamper detection mechanism, and wireless interface.

Other features may include one or more of the following: E-ink display, buttons, microphone, buzzer and multicolor LED for user interface; Identity authentication module (IAM) interface that enables plurality of user authentication methods such as smart card reader or biometric; FET based drive circuitry to drive the multicolor LED that supports plurality of colors, intensity and flash pattern to indicate glanceable status of the system; drive circuitry for E-ink user interface with plurality of views each configured to present evidence on state of the transport; drive circuitry for piezo electric buzzer to provide audio feedback to the user; microphone interface circuitry for the user to provide wakeup words and or voice; Actuator latch drive circuitry and latch state read back methods; memory interface to store state and statistics of transport; environmental & tamper detection sensor interface to monitor temperature, shock and vibration; and crypto and secure element interface to safely store public/private keys.

In some implementations, the E-ink may display icons such as loading dock or in transit to show the current status of associated medication that is been tracked.

In some implementations, the E-ink may display shipment tracking details. For example, information such as from & to destination, travel time and who signed at tote departure and arrival may be displayed or otherwise communicated by a user interface.

In some implementations, the E-ink may display information collected from the environmental sensor. For example, information such as temperature of medication in transit, monitor tamper evidence sensor signal, humidity, shock and vibration over time may be displayed or otherwise communicated by a user interface.

In some implementation, the multicolor LED user interface may act as a glanceable status indicator. In this regard, the LED color, flash pattern and intensity may indicate different status based on user accessing the secure storage location and workflow.

Example 1: During medication loading workflow the led lighting may guide the user to the medication at a glance.

Example 2: If the medication in the tote expired then the LED may flash red.

Example 3: During medication audit the system may guide by lighting the LED's so the user can identify the med easily.

Example 4: If the battery level lower than threshold then the led may flash.

Example 5: Led color and flash pattern may indicate that an authorized user unlocked the tote.

A handheld device may scan the led color, intensity and flash pattern and identify ifs glanceable status during manufacturing or in field. The device may comprise an inspection equipment or a mobile application, and/or an optical reading device to read the multicolor visual indicator and obtain the failure modes and conditions on the smart tote.

An authentication system may automatically determine a plurality of user authorization methods, and the user may then select one or more of the determined authorization methods to unlock the smart tote. User identity may be securely transmitted to the server, and authorization may be returned from the server to unlock the smart tote. In some implementations, the authentication mechanism may use contactless smart card, and in some implementations the authentication mechanism may use barcode, biometric identification, ECG based wearable device, or a mobile phone. In some implementation, the authentication mechanism may include remote authentication. For example, if the user loses their badge or smart phone, super user may provide remote authentication.

In some implementations, the disclose system and method may include a sensor interface system, which monitors NIST traceable environmental sensor & tamper detection data in real time.

An audible sound may indicate user actions such as presenting badge to the smart lock or when an actuator command is been executed. For example, in some implementation a piezo beeper may be used with different tones to indicate different actions.

The system and/or method may include communication architecture (CA), which may use plurality of PAN protocols such as (802.15.4/BLE) to talk to the remote device. In this regard, the system and/or method may utilize the CA to achieve one or more of the following features: beacon for asset tracking; environmental sensor and tamper detection monitoring; Real time and offline mode support; and tote content identification and inventory tracking. In some implementations of smart tote, the CA may bypass hospital IT, thereby reducing implementation time (e.g., implementing a drop ship model based on PAN protocol support).

The system and/or method implementing communication architecture (CA) may support an offline mode. When a network connection to the field hub or gateway is lost the smart tote may still allow the user to continue with their action, and the system may store and forward the actions when the network is restored.

The system and/or method implementing communication architecture (CA) may enable the smart tote to broadcast beacons to remote host with the medication information for asset tracking. In some implementations, users may also read the beacons using a mobile device such as a phone or tablet.

The system and/or method may automatically identify the contents in the tote and assist the end user in inventory tracking and loading the medication.

In some implementations, the disclosed system and/or methods may include power architecture that utilizes disposable batteries or, in other implementations, the power architecture may implement rechargeable battery or a supercapacitor.

A method for conserving power in battery operated devices based on system factors and user preference is disclosed. Devices may be placed in low power states (ranging from system off state to various levels of sleep state) and may be woke up periodically (wake up period) to enable radio communications, to check in with a gateway/hub for updates or to perform transactions.

The low power state and wake up period may be configured by the gateway/hub for devices based on system usage factors and user preferences.

In some implementations, environmental sensors such as occupancy sensors may be used. In some implementations, a microphone may be used. Activation to wake up the device from deep sleep mode may be by key word activation, user action by pushing a button, or system usage factors such as user presence, or office schedule.

A system and method for energy harvesting using plurality of sources is disclosed to increase smart tote operation life. In some implementations, the system or method uses piezo transducers interfaced to buttons or electromagnetic induction from lock actuator action or wireless energy from RF sources to harvest energy.

The following commentary and illustrations define a solution for storing, transporting and dispensing items using the foregoing technology.

Figure 23A:
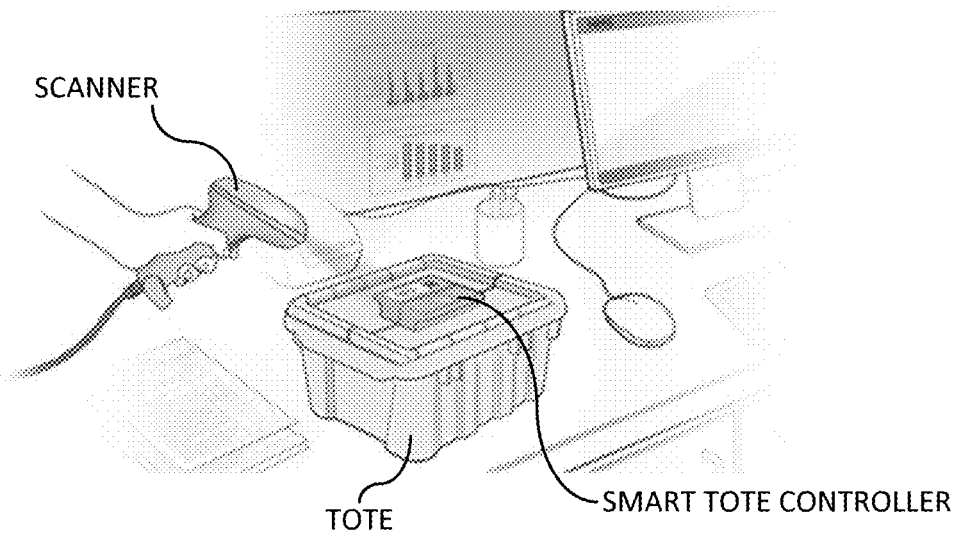
FIGS. 23A-24F, depicts a smart tote concept, according to various aspects of the subject technology.
Figure 23B:
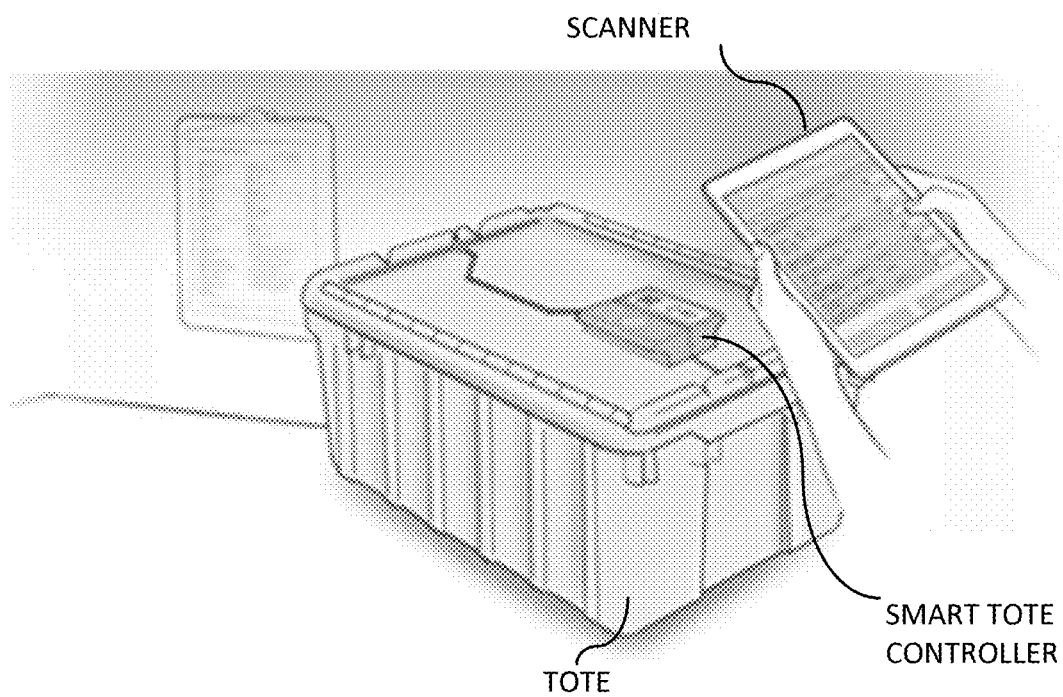

As shown in FIGS. 23A and 23B, the smart tote concept may include a lockable device activated bin for secure item storage and transport.

The smart tote may be retrofitted to an existing tote for controlled security.

Figure 24A:
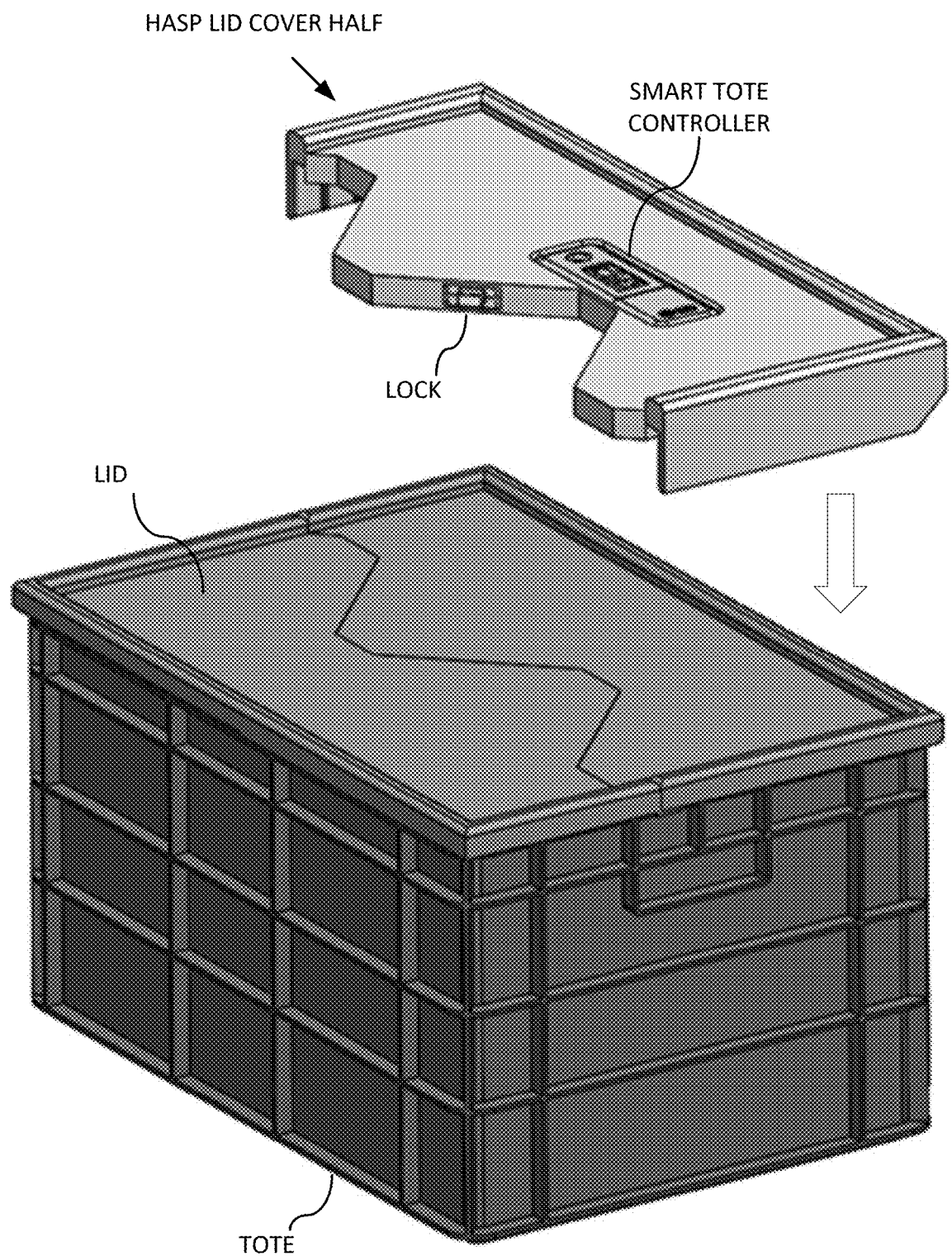
Figure 24B:
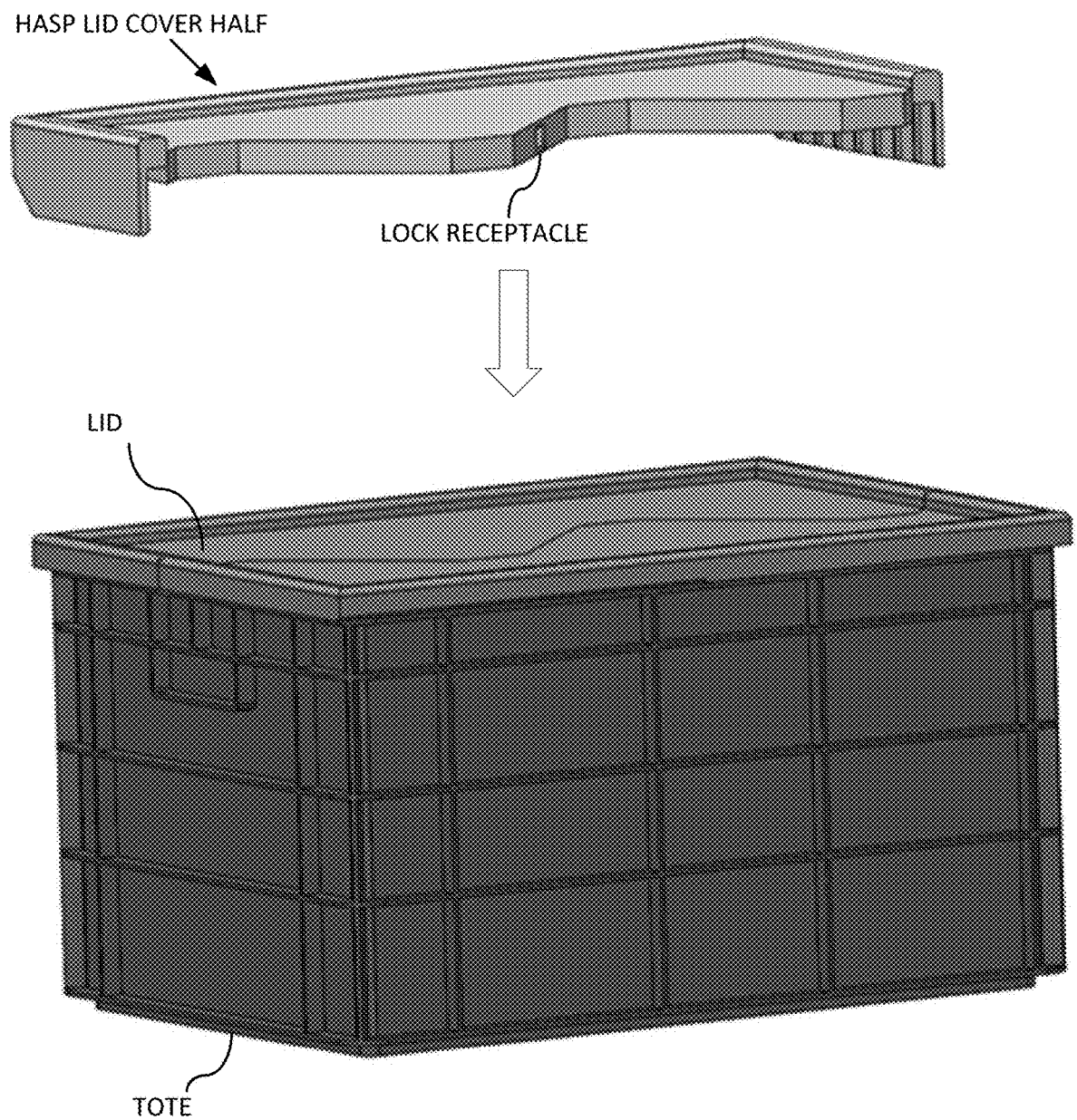
Figure 24C:
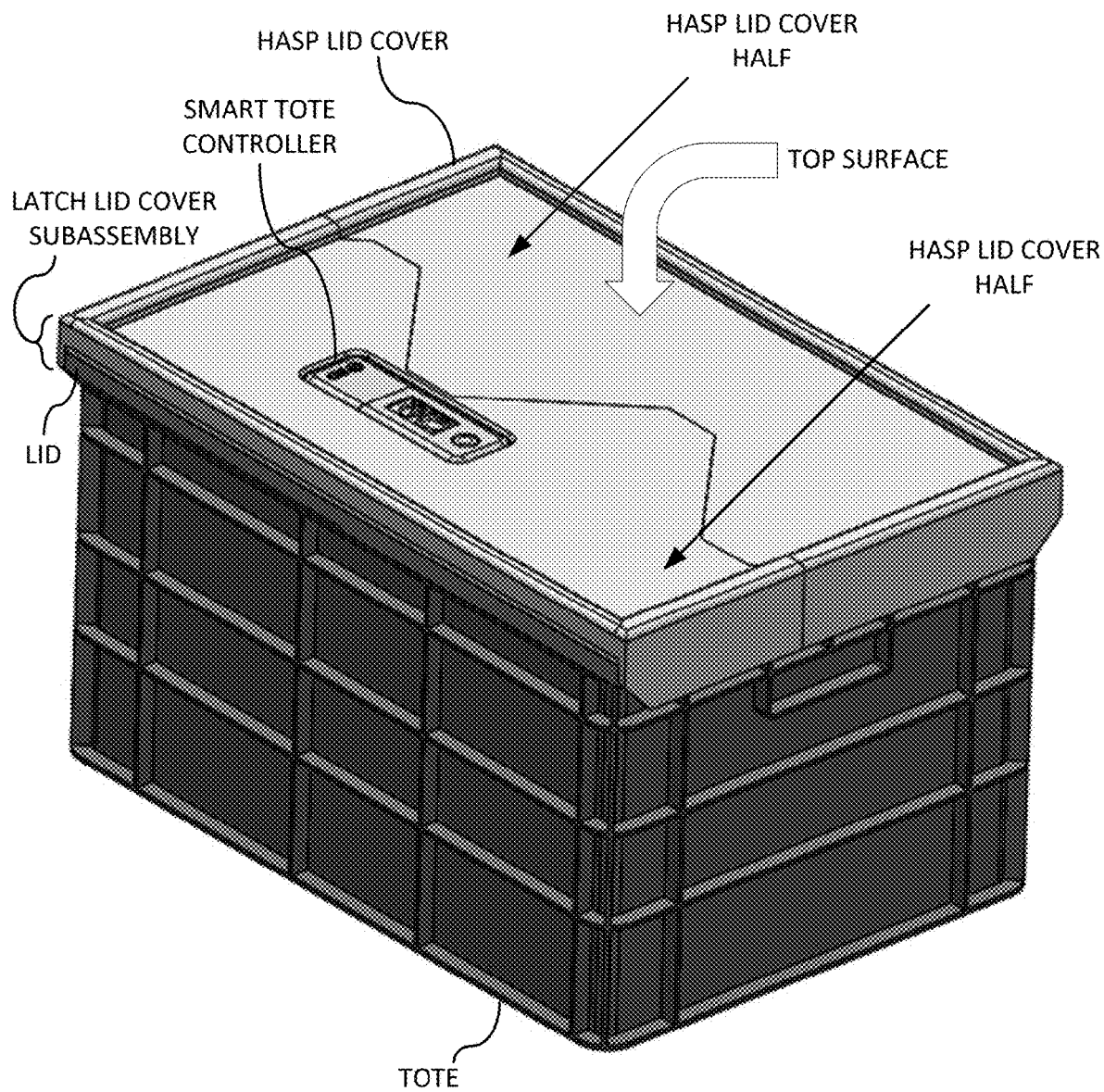
Figure 24D:
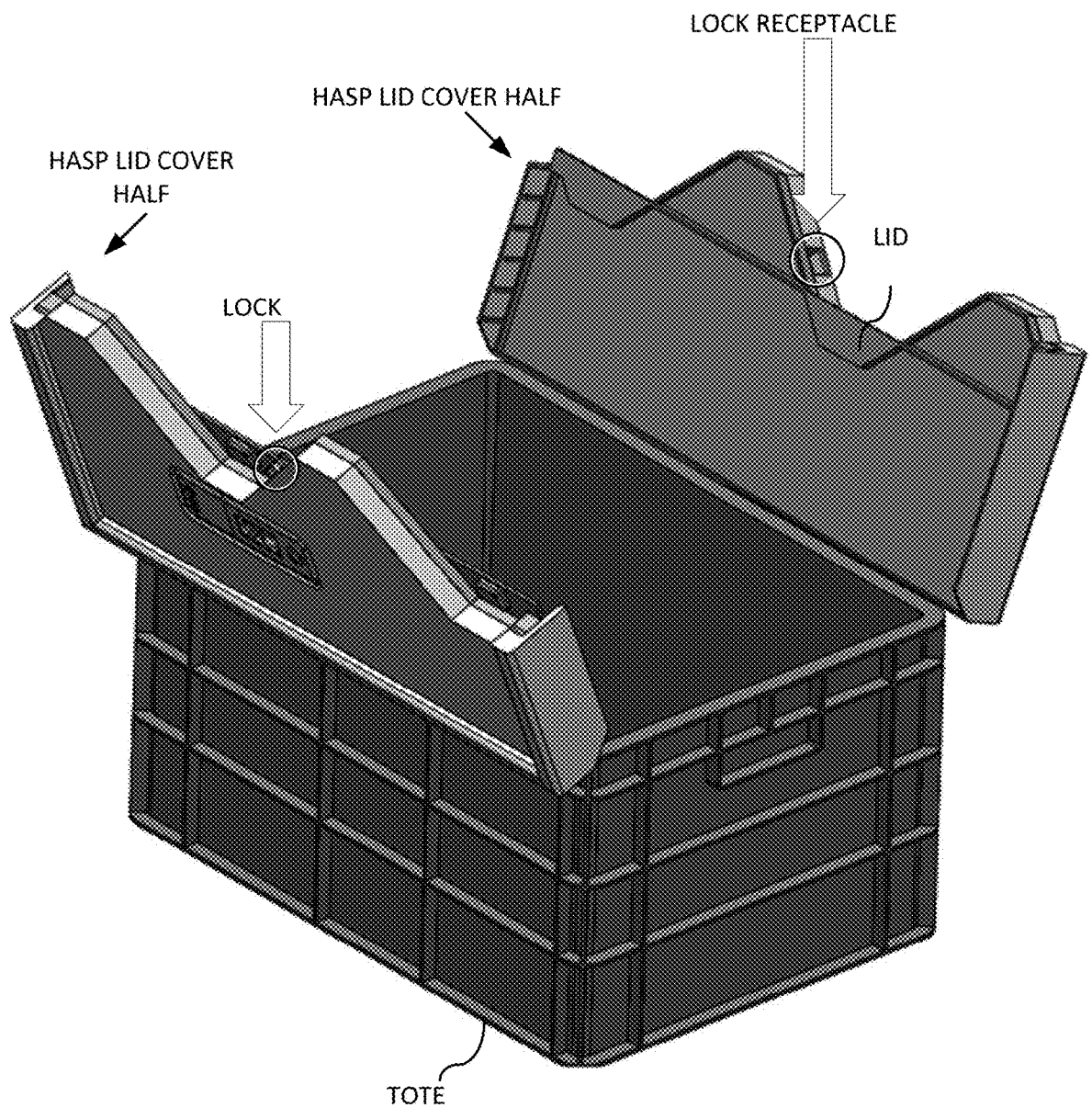
Figure 24E:
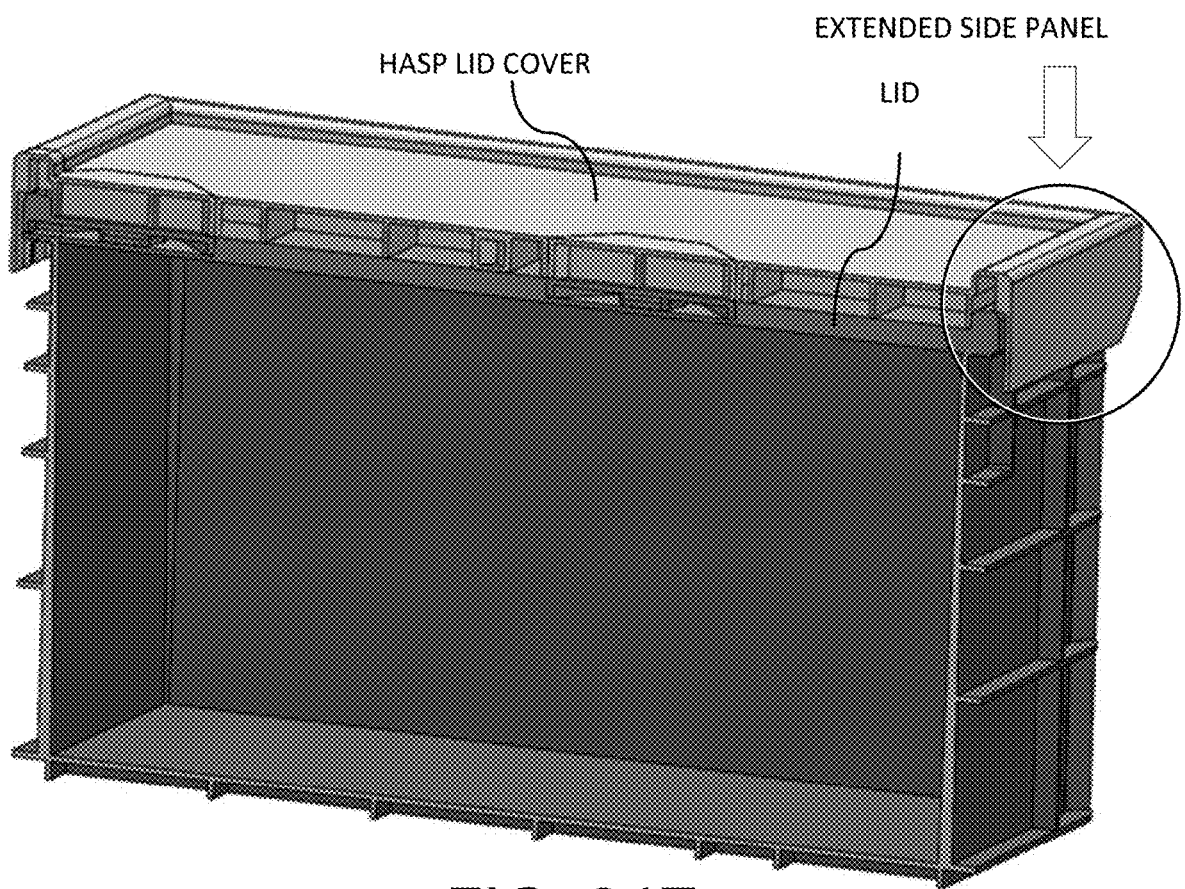
Figure 24F:
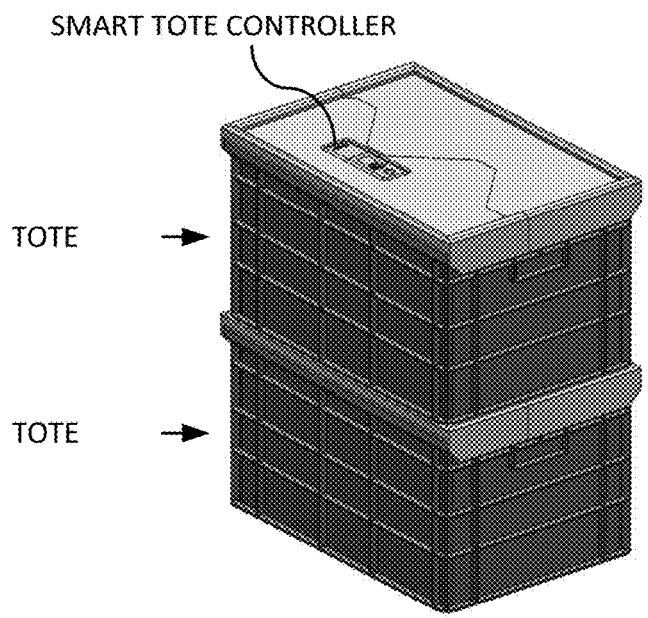

The smart tote may include an off-the-shelf lidded tote that includes reader module and electro-mechanical latch and latch bracket. The reader module may include one or more of a NFC reader, LEDs, light pipe, global positioning system (GPS) device, shock recording, batteries, audio indicator, barcode, temperature monitoring, and e-ink display. The e-ink display may visually (and/or audibly) indicate to and from information, content information, date, etc. The smart tote may communicate wirelessly to other devices to manage access and inventory. Automatic population of stock numbers may be performed when received by clinic. The smart tote may include a latch lid cover subassembly and a hasp lid cover that are mechanically attached to a tote's existing lids. (See FIGS. 24D and 24F.)

The latch lid cover subassembly may include a latch lid cover, smart reader and electro-mechanical latch. The latch lid cover may include features that mount the smart reader and latch. The reader may sit flush to the top exterior of the lid cover. By sitting flush, multiple smart totes may be stacked on top of each other. The smart reader's batteries may be externally accessed. When the smart reader batteries expire, the latch may remain in the locked position, and the batteries may be replaced to continue operation. The smart reader LED may indicate smart tote location. An audio indicator may alert an unlocked or open lid. The hasp lid cover may include a feature that interfaces with the latch. (See FIGS. 24A-24F.)

The smart tote reader module and latch Hook may be designed to indicate an attempt to divert. They may include material that may be deformed showing tamper evidence. Both the latch lid and hasp lid may have extended side panels to increase security against diversion by prying up the lids. (See FIGS. 24D and 24E.)

Secure Modular Bin Array

Another aspect of the disclosure relates to a slimline smart bin array system and methods, which enables safe and secured medication management solution with a focus on optimizing the existing user space and resources ("slimline bin" or "slimline"). According to various implementations, the disclosed system includes configurable smart bins (different sizes), wireless connectivity, and an enclosure to hold the array of bins securely on a wall. The system and method may also include a plurality of user interfaces, along with actuator that unlocks the slimline bin with a secured authorization from a server. The system and method may further implement a machine learning (ML) inference and data analytics to optimize power consumption on the slimline bin based on its awareness of spatial context.

In healthcare settings, there is a need for space & cost optimized enterprise secured medication storage and dispensing solutions. Some solutions use an automated dispensing cabinet (ADC) to control medications. ADC are expensive and take up a significant space. Existing user space such as drawers, cabinets and carts may be used to store and dispense medications. However, drawbacks include a lack of security, poor traceability of the medications, and a very manual process which utilizes more nurses or care giver resources. The disclosed solution includes a slimline with smart bin array transforms the underutilized or unutilized user wall space into a highly optimized enterprise medication management space.

Systems and methods for highly optimized medication storage and dispensing in healthcare settings are disclosed. The systems and methods may include a wall mounted slimline smart bin array system with configurable wirelessly connected smart bins (e.g., in different sizes), a plurality of user interfaces, a server authorized actuator lock, and may include location tracking, and may enable an enterprise solution for inventory tracking.

The disclosed system may include a processor, memory, input/output device, environmental sensor, tamper detection and wireless interface.

Other features may include one or more of the following: E-ink display, microphone, buzzer and multicolor LED for user interface; identity authentication module (IAM) interface that enables plurality of user authentication methods such as smart card reader or biometric; FET based drive circuitry to drive the multicolor LED that supports plurality of colors, intensity and flash pattern to indicate glanceable status of the system; drive circuitry for E-ink user interface with plurality of views each configured to present the current state of the workflow; drive circuitry for piezo electric buzzer to provide audio feedback to the user; microphone interface circuitry for the user to provide wakeup words and or voice prompts; actuator latch drive circuitry and latch state read back methods; memory interface to store state and statistics of slimline bin status; sensor interface to monitor tamper, environmental condition & content sensing; and crypto and secure element interface to safely store public/private keys.

The disclosed system architecture may optimize an existing user space with a wall mounted slimline enclosure and configurable smart bins with wireless connectivity. In some implementations, a slimline enclosure and bin may be placed on a countertop.

In some implementations, the disclosed system architecture may include a latch and electronics to drive the latch as part of the bin. In some implementations, both the latch and electronics may be part of slimline enclosure.

In some implementations, the disclosed system architecture may include a bin that tilts open giving user access to medication and in other implementation bin pops open as a drawer.

In some implementations, the disclosed system architecture may automatically determine a plurality of user authorization methods. The user may then select one of the determined authorization methods to unlock the slimline bin.

An authentication method that securely transmits the user identity to the server and gets authorization to unlock the slimline bin is also disclosed. In some implementations, the system may include, and the authentication method may use, contactless smart card and in other implementations it could use barcode, biometric identification, ECG based wearable device or a mobile phone. In some implementations, the authentication method may include remote authentication. For example, if the user loses their badge or smart phone, a super user can provide remote authentication.

In some implementations, the systems and/or methods may utilize a sensor interface to automatically identify the quantity of contents in the slimline bin and tamper detection of slimline bin or enclosure. For example, the method may include monitoring for tamper detection on slimline enclosure attached to wall (e.g., using one or more sensors), and the slimline bin attached to enclosure, in real time using optics or electromagnetic sensing. In some implementations, the system and/or method includes a sensor interface such as load cell, optics with a led & photodiode, acoustics or RF to sense the quantity of content inside the bin.

A method by which an audible sound indicates user actions such as presenting badge to the slimline or when an actuator command is been executed is also disclosed. In some implementations, the system may include, and the method may use, a piezo beeper with different tones to indicate different actions.

According to various implementations, the system may include communication architecture (CA), which may use plurality of PAN protocols such as (802.15.4/BLE) to talk to the remote device. Accordingly, the disclosed system and/or method may use the CA to achieve one or more of the following features: beacon for asset tracking; real time and offline mode support.

In some implementations, the disclosed slimline bin (e.g., using CA) may bypass hospital IT, thereby reducing implementation time (e.g., implementing a drop ship model based on PAN protocol support).

The system and/or method implementing communication architecture (CA) may support an offline mode. When a network connection to the field hub or gateway is lost the disclosed slimline bin(s) may still allow the user to continue with their action, and the system may store and forward the actions when the network is restored.

In some implementations, the slimline bin(s) have the ability to broadcast beacons to a remote host, with the medication information for asset tracking. In some implementations, users can also read the beacons using a mobile device such as a phone or tablet.

In some implementations, the disclosed system and/or methods may include power architecture that utilizes disposable batteries or, in other implementations, the power architecture may implement rechargeable battery or a supercapacitor as an energy source for each bin. In some implementations, the power architecture (PA) may require one high capacity energy source to power the entire slimline bin array. For different implementations of high capacity energy source (PoE, battery, external power supply) and its interface using wired or docking connector see attached slides and docs.

In some implementations, a slimline bin array may be connected to an external power supply, the external power supply may directly power the slimline bin, or may charge the battery on the bin or enclosure. In some implementations, the disclosed system and method may include power architecture that uses wireless power transfer to access the slimline smart bin.

A method for charging the system using a plurality of wireless energy sources is also disclosed. In some implementations, a near field (such as NFC, Qi, Resonant and inductive) or far field (such as WiFi, UHF) wireless power transfer are used as energy source to access the slimline bin.

In some implementations, a multiplexed wireless charging scheme may be used to charge the secure storage solution. In some implementations, only one storage location may be accessed at a given time inside a slimline.

In some implementations, guided lights or mechanical features are used to dock the secured storage space for wireless charging.

A method for conserving power in battery operated devices based on system factors and user preference is disclosed. In some implementations, the method may include placing devices in low power states (ranging from system off state to various levels of sleep state) and waking up the devices periodically (wake up period) to enable radio communications, and checking in with a gateway/hub for updates or to perform transactions.

The low power state and wake up period may be configured by the gateway/hub for devices based on system usage factors and user preferences.

In some implementations, the system may include, and the method may include using, environmental sensors such as occupancy sensors. In some implementations, the system and/or method may use microphone with key word activation, user action by pushing a button or system usage factors such as user presence, office schedule to wake up the device from deep sleep mode.

A method for energy harvesting using plurality of sources to increase slimline smart bin operation life is also disclosed.

In some implementations, electromagnetic induction from lock actuator action or wireless energy from RF sources may be used to harvest energy.

In some implementations, the e-ink of the user interface of the device may display medication name, dosage and expire date. In other implementations, icons such as loading dock or in transit may be displayed to show the current status of associated medication that is been tracked.

In some implementations, the multicolor LED user interface may act as a glanceable status indicator. For example, the LED color, flash pattern and intensity may indicate different status based on user accessing the secure storage location and workflow.

Example 1: During medication loading workflow the led lighting can guide the user to the medication at a glance.

Example 2: If the medication in the slimline bin expired the LED can flash red.

Example 3: During medication audit the system may guide by lighting the LED's so the user can identify the med easily.

Example 4: If the battery level lower than threshold led can flash.

FIG. 18 depicts an array of secure modular bin assemblies for secure item storage and retrieval, according to various aspects of the subject technology. The bin array may be placed on the counter top or wall mounted. The assembly array may include storage bins that may be created by connecting bin subassemblies. The bin assemblies may come in different sizes and may be arranged to create the bin array.

As described previously, the slimline smart bin array system includes configurable smart bins that may be of different sizes, interconnected with each other to form a single unit. A slimline bin may be placed and used anywhere the storage and retrieval of items are needed such as a med-room, caregiver station, and/or patient's bedside.

A wall mounted unit may be locked to the wall by mechanical means. A key or electro-mechanical latch may be used to unlock the slimline from the wall. Releasing the unit from the wall gives the user the access to the rear of the unit. A manual release mechanism may be accessible from the rear of the unit. The manual release mechanism may include a color-coded lever that the users uses to unlock all storage bins. All storage units may be unlocked simultaneously using the manual release mechanism, and the user may be given immediate access to all contents.

The slimline assembly may also be placed on a shelf or counter. Also, the unit may be mounted on the wall to keep counter top space clear. The slimline may be configured to use an electrical wall outlet to power units. The slimline assembly may be operated by common batteries.

The slimline assembly may communicate wirelessly to other devices. Each bin can contain an e-ink display. The display may indicate information about its contents. Each bin subassembly may have a barcode located on its front face.

The bin subassemblies may all have overlapping features and interlocks to prevent diversion. The unit may be designed to indicate the attempt to divert. For example, material may be deformable such that, when diversion occurs, the material is deformed showing tamper evidence. In some implementations, the bin hook may break and leave a piece in the latch making it unusable thereby indicating a break-in.

The slimline may be used in a refrigerated environment. The material and components may be used at lower temperatures.

Figure 25A:
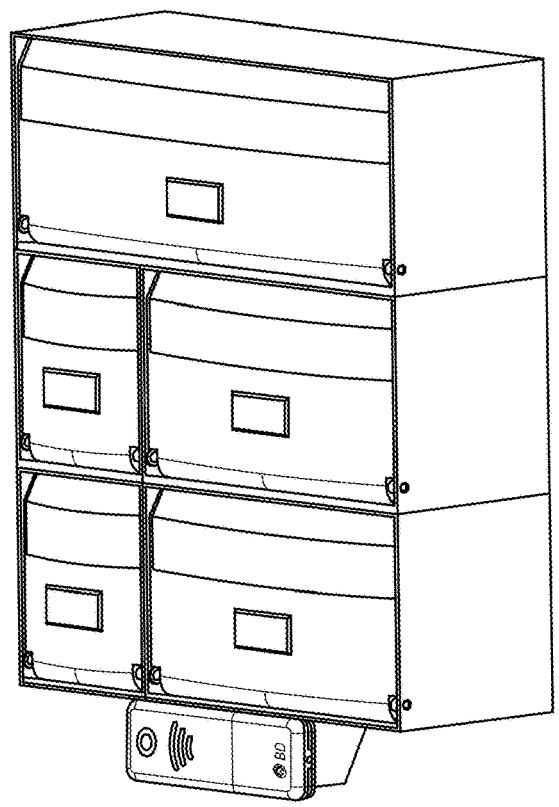
FIGS. 25A and 25B depict a wall-mounted slimline bin assembly with an integrated smartcard reader, according to various aspects of the subject technology.
Figure 25B:
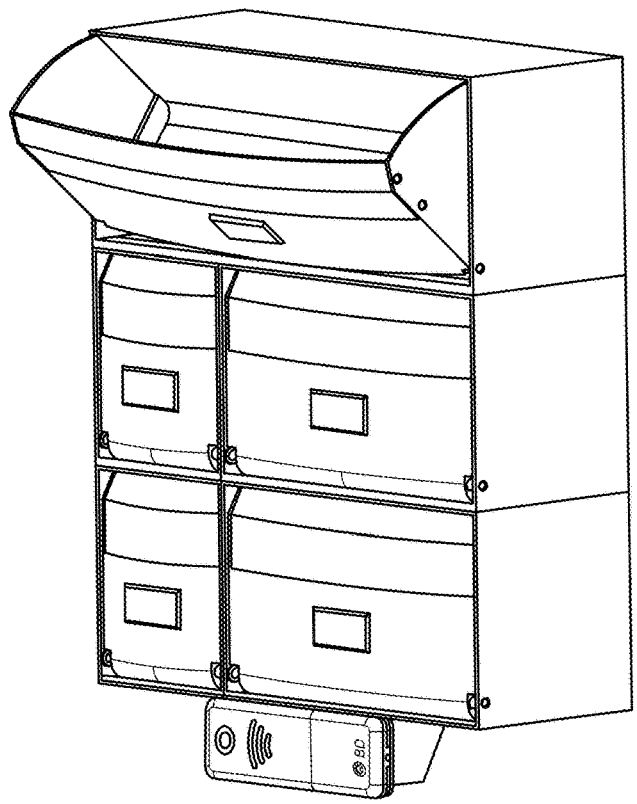
Figure 26:
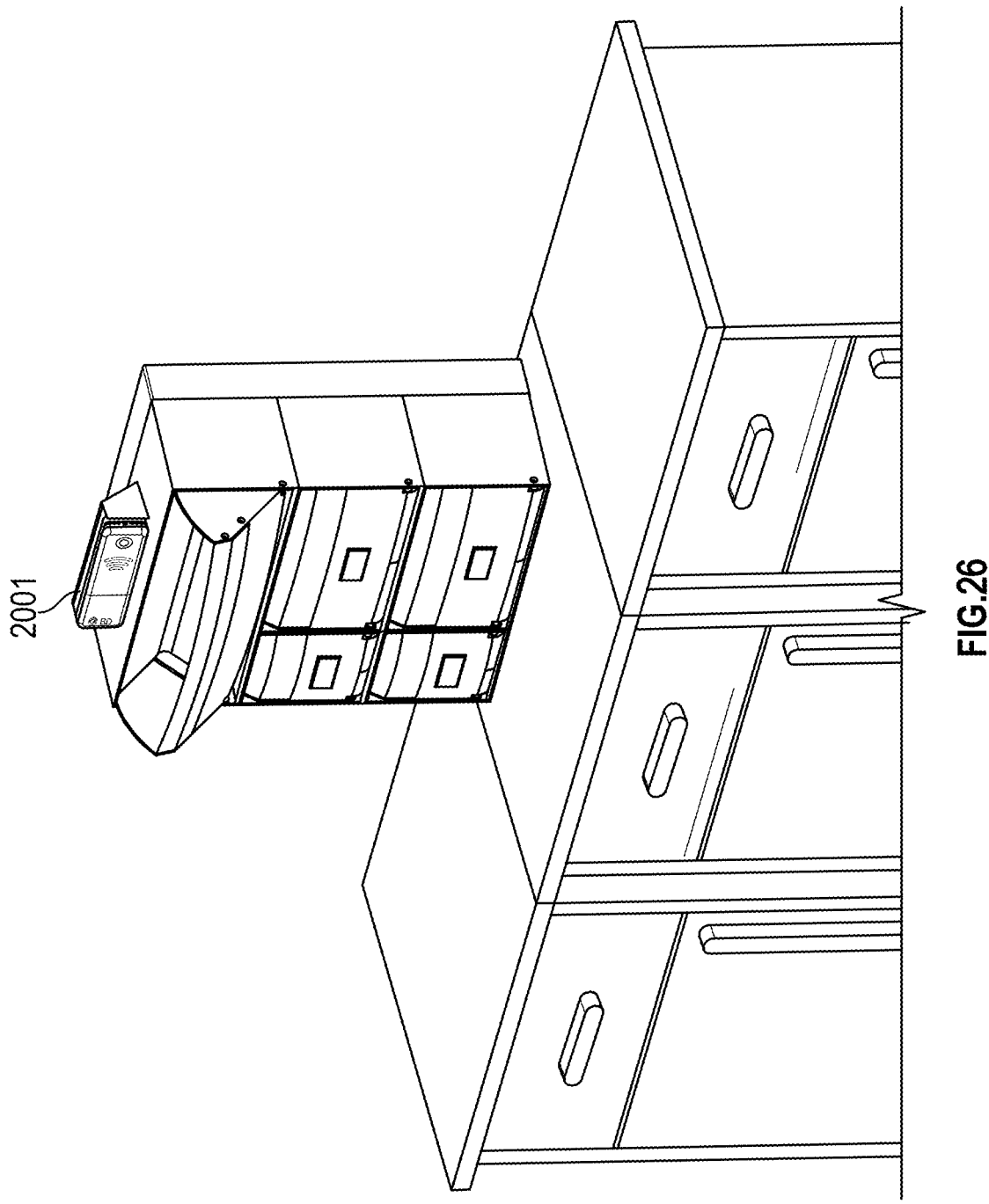
FIG. 26 depicts the bin array placed on a counter top, according to various aspects of the subject technology.

FIGS. 25A and 25B depict a wall-mounted slimline bin assembly with an integrated smartcard reader, according to various aspects of the subject technology. In the depicted example the assembly is created by connecting different size bin subassemblies together. The different size bins may be custom arranged in any pattern. The connection features and hardware to connect the bins are at the rear of the unit. FIG. 26 depicts the bin array placed on a counter top, according to various aspects of the subject technology. In the depicted implementation, the smartcard reader 2001 is relocated to the top of the assembly.

As depicted in FIGS. 25A and 25B, the smartcard badge reader may be used for controlled security. The slimline may be accessed using the card reader. Additionally or in the alternative, the bin assembly and/or the smartcard badge reader may be integrated with or accessed using a PC, tablet computer, smartphone, barcode reader. A biometric reader may be part of the bin assembly and/or implemented as the reader, and used for controlled security.

Figure 27:
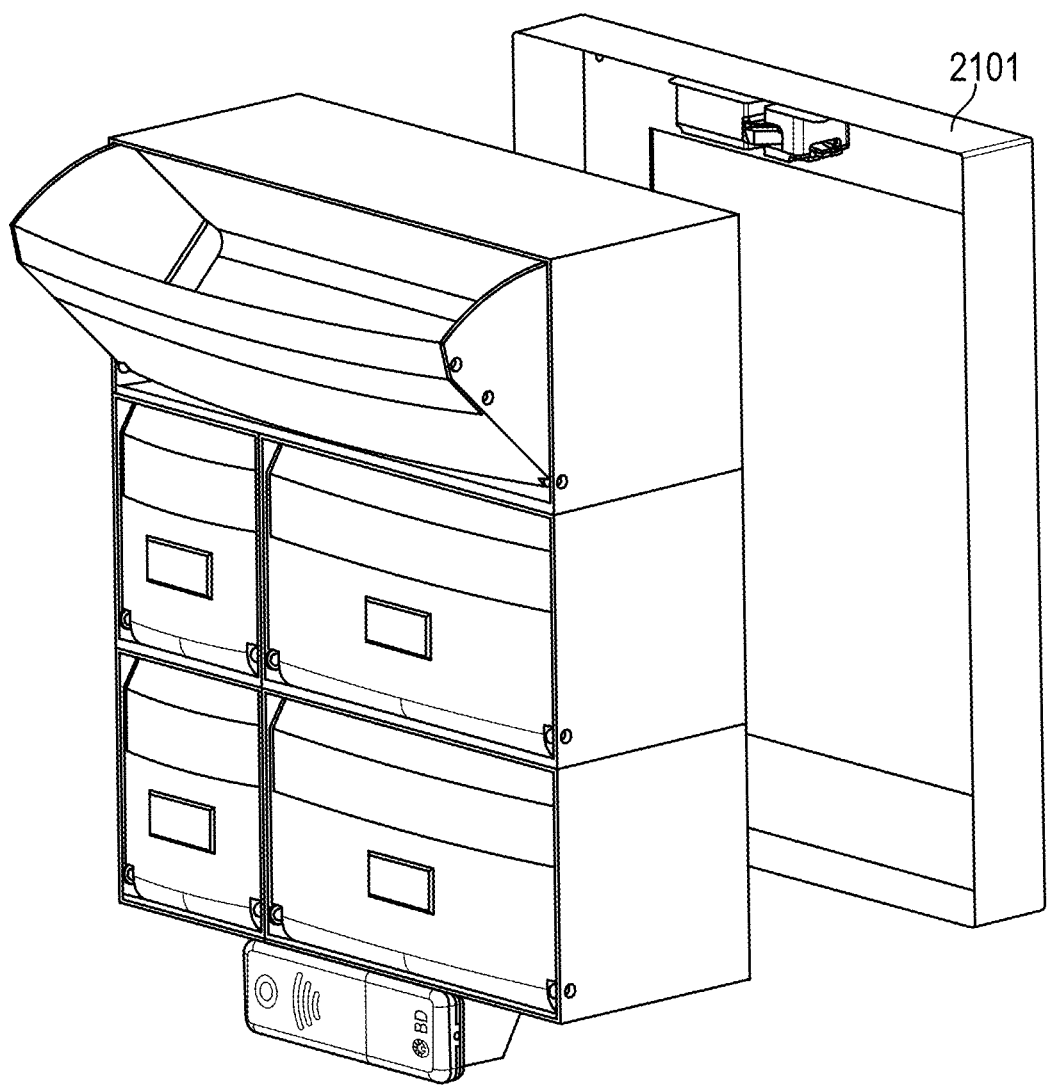
FIG. 27 depicts an example slimline bin assembly mounted to a wall using a mechanical support bracket 2101, according to various aspects of the subject technology.

FIG. 27 depicts an example slimline bin assembly mounted to a wall using a mechanical support bracket 2101, according to various aspects of the subject technology. According to various implementations, a wall mounted unit may be locked to the wall by mechanical means. A key or electro-mechanical latch may be used to unlock the assembly from the wall.

In some implementations, the bin subassemblies may include a storage bin, outer housing, latch, PCBA, battery, cabling, and bin latch hook, spring, window, barcode and features that would indicate tamper evidence. The width of the bin subassemblies may be single wide (1x), double wide (2x) or triple wide (3x). The bin subassemblies may share the same components and geometry except for the width. The outer housing may include features to mount latch, PCBA, LEDs, and battery. Also, features to pivot the storage bin and stops that limit bin rotation. The Outer Housing also may include mounting features that interface with other outer frames (e.g., in order to create a slimline module assembly).

Figure 28:
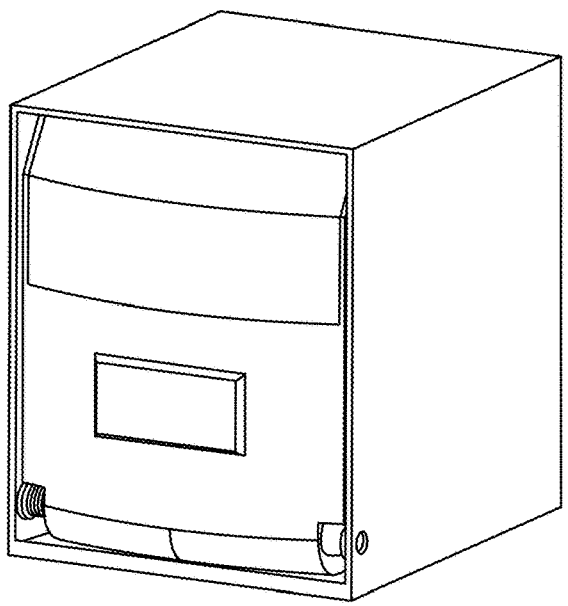
FIG. 28 depicts an example single-width storage bin with a pivoting storage bin, according to various aspects of the subject technology.
Figure 29:
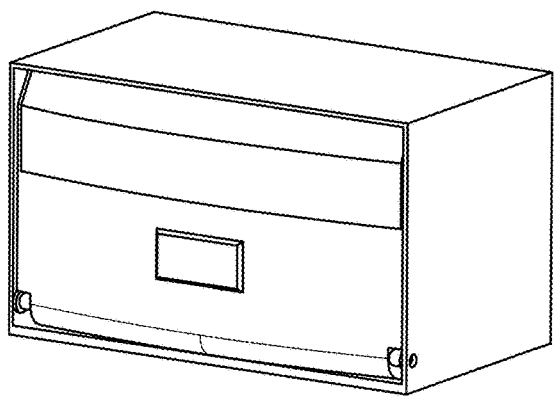
FIG. 29 depicts a double-width and triple-width storage assemblies with pivoting storage bins, according to various aspects of the subject technology.
Figure 29:
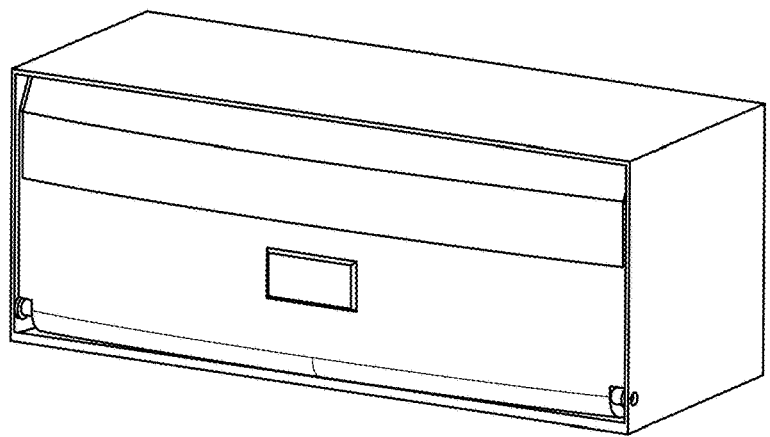

FIG. 28 depicts an example single-width storage bin 2200 with a pivoting storage bin, according to various aspects of the subject technology. FIG. 29 depicts a double-width and triple-width storage assemblies with pivoting storage bins, according to various aspects of the subject technology. The storage bin may include features to mount a bin hook (that interfaces with the latch), mounting features for a window and spring mounting. The latch may operate from common batteries. It also contains sensors that can interface with indicating open/close status. The latch may include an on-board memory to digitally store content/location information. The latch may be part of the storage bin subassembly. The storage bin may be connected to the outer housing 2201 via its pivot feature 2202. Spring loaded and locked by latch, when released the storage bin pivots forward allowing the access to its stock. The user may be indicated which bin to access when one of the slimline bins pivot forward for item removal.

Figure 30:
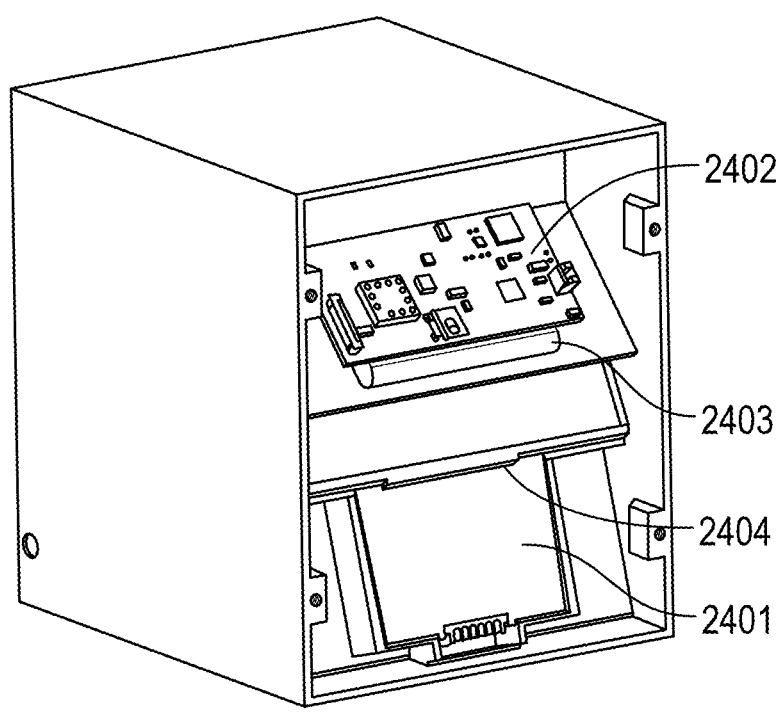
FIG. 30 depicts an example outer housing of a bin assembly with an electro-mechanical latch, PCBA, and battery, according to various aspects of the subject technology.

FIG. 30 depicts an example outer housing of a bin assembly with an electro-mechanical latch 2401, PCBA 2402, and battery 2403, according to various aspects of the subject technology. In such implementations, the PCBA may be communicated via a wire and operate the latch 2401.

Figure 31A:
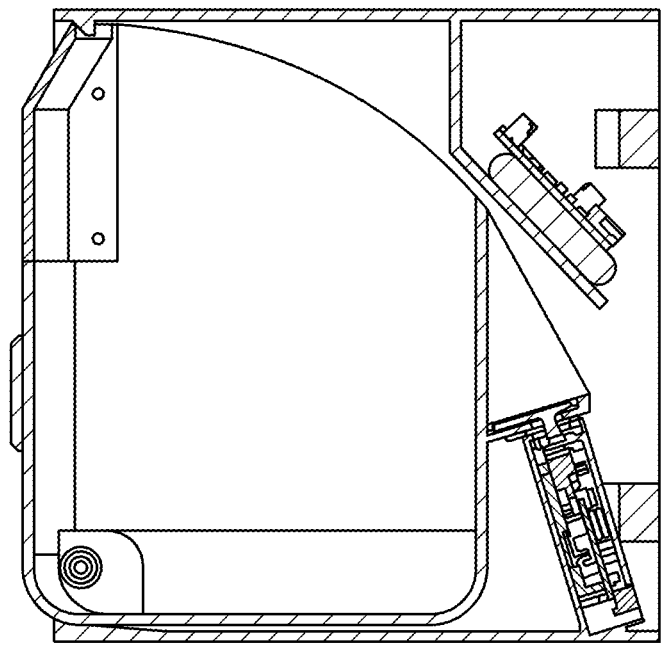
FIGS. 31A and 31B depict cut-away views of an example disclosed storage bin, including a hook that interfaces with the disclosed electro-mechanical latch, according to various aspects of the subject technology.
Figure 31B:
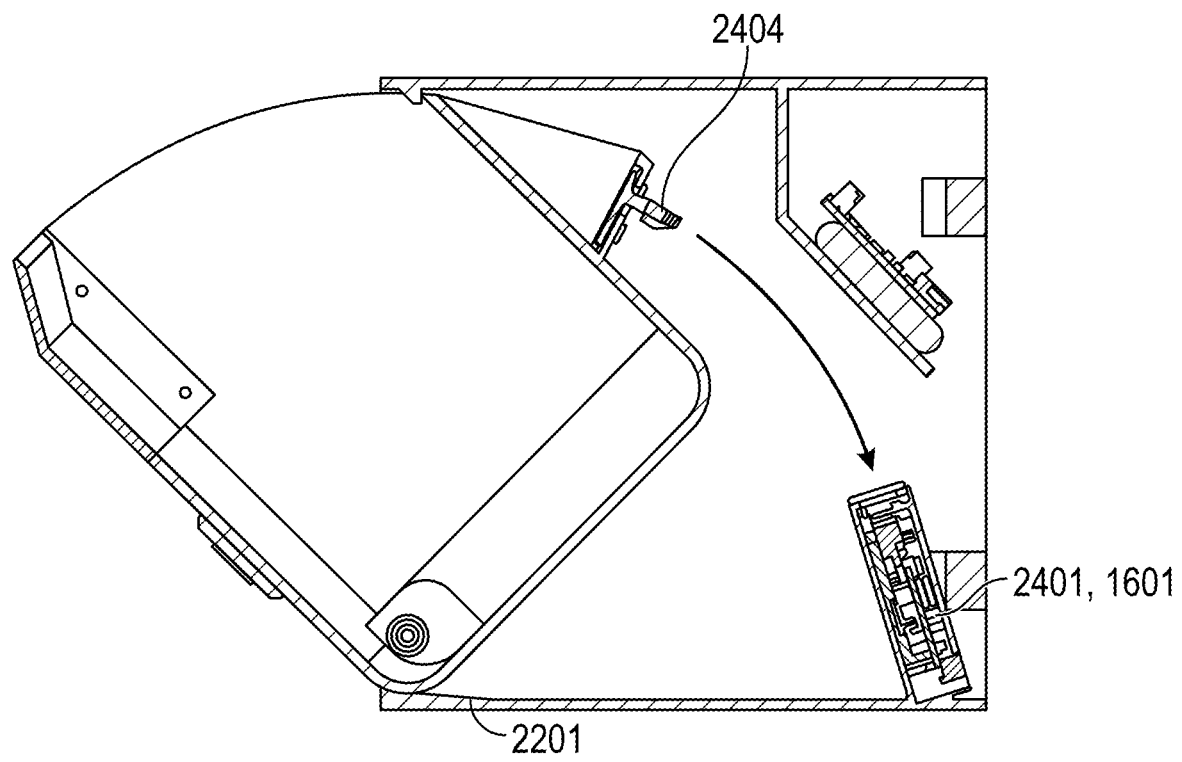

FIGS. 31A and 31B depict cut-away views of an example disclosed storage bin, including a hook 2404 that interfaces with the disclosed electro-mechanical latch, according to various aspects of the subject technology. The (tipping) storage bin, when manually being closed, may pivot rearward and the hook passes through an arc and interfaces with the latch. In its locked position, the outer housing protects access to the contents of the storage bin. The storage bin may include a spring-loaded pivoting feature. The front of the storage bin may include a window. The window may be clear or translucent. The translucent window may be configured to let a user know that the bin contains items but mask the wordings on item labels. The tipping outward of the storage bin allows for the easy retrieval of its contents. The access opening at the max tip angle leaves the user an unobstructed access path to its contents.

Figure 32:
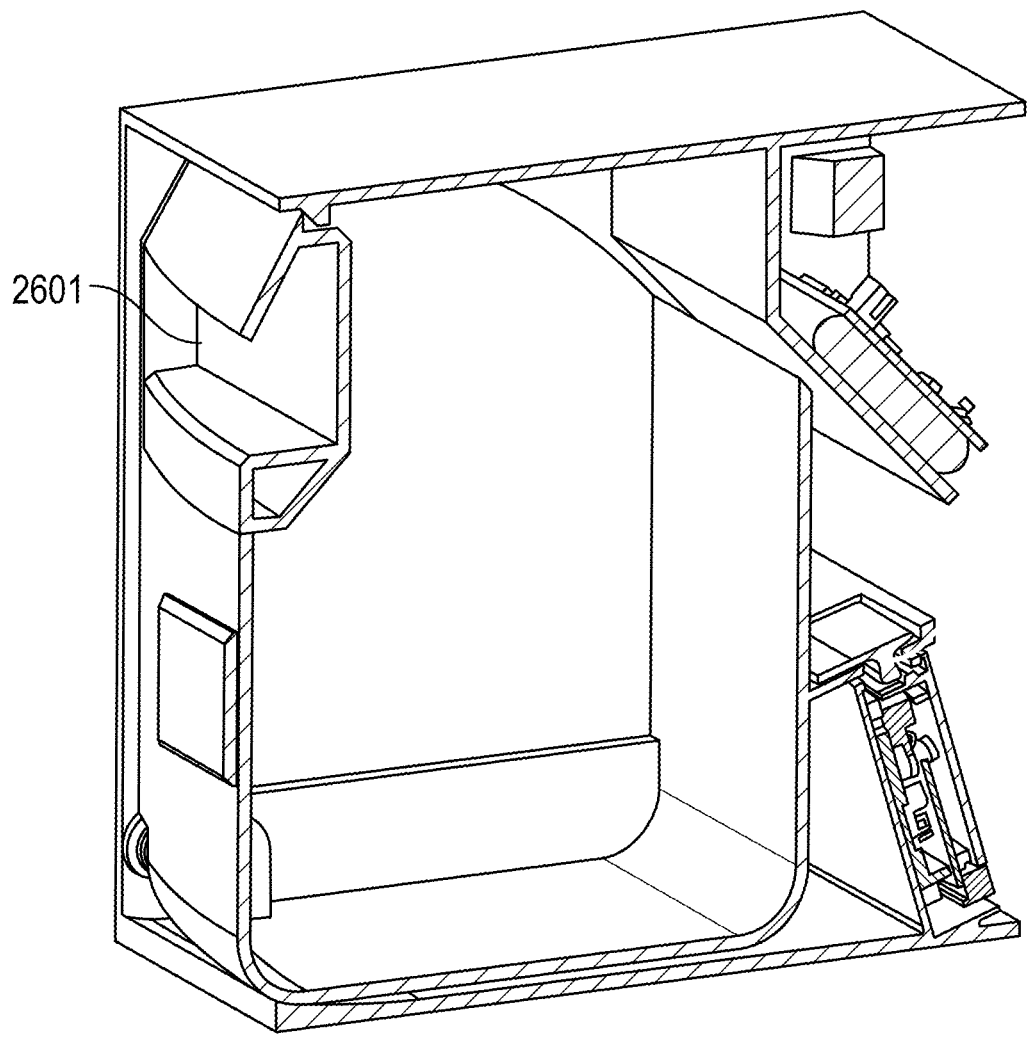
FIG. 32 depicts a cut-away view of an example storage bin with a handle feature, according to various aspects of the subject technology.

FIG. 32 depicts a cut-away view of an example storage bin with a handle feature 2601, according to various aspects of the subject technology. The handle feature may be used with a storage bin without a pivot spring. Additionally or in the alternative, the storage bin may include a window feature. Furthermore, some implementations may also include multi-colored LED lights. The system may activate the LEDs, and the window could become a light pipe and illuminate the LEDs output. The illuminated window would alert the user with the location of the contents.

In implementations according to FIG. 32, one or more of the following features may be included: (1) The storage bin incorporates a handle. (2) The storage bin pulls out horizontally from the outer housing and eventually hits a stop feature. Once the storage bin the bin hits the stop feature it may be tilted downward and come to a stop. The angled bin allows for easy retrieval of items. (3) The storage bin may be spring loaded and "pop" outward on latch release indicating location of item. (4) The storage bin can use LED's for item location.

Figure 33:
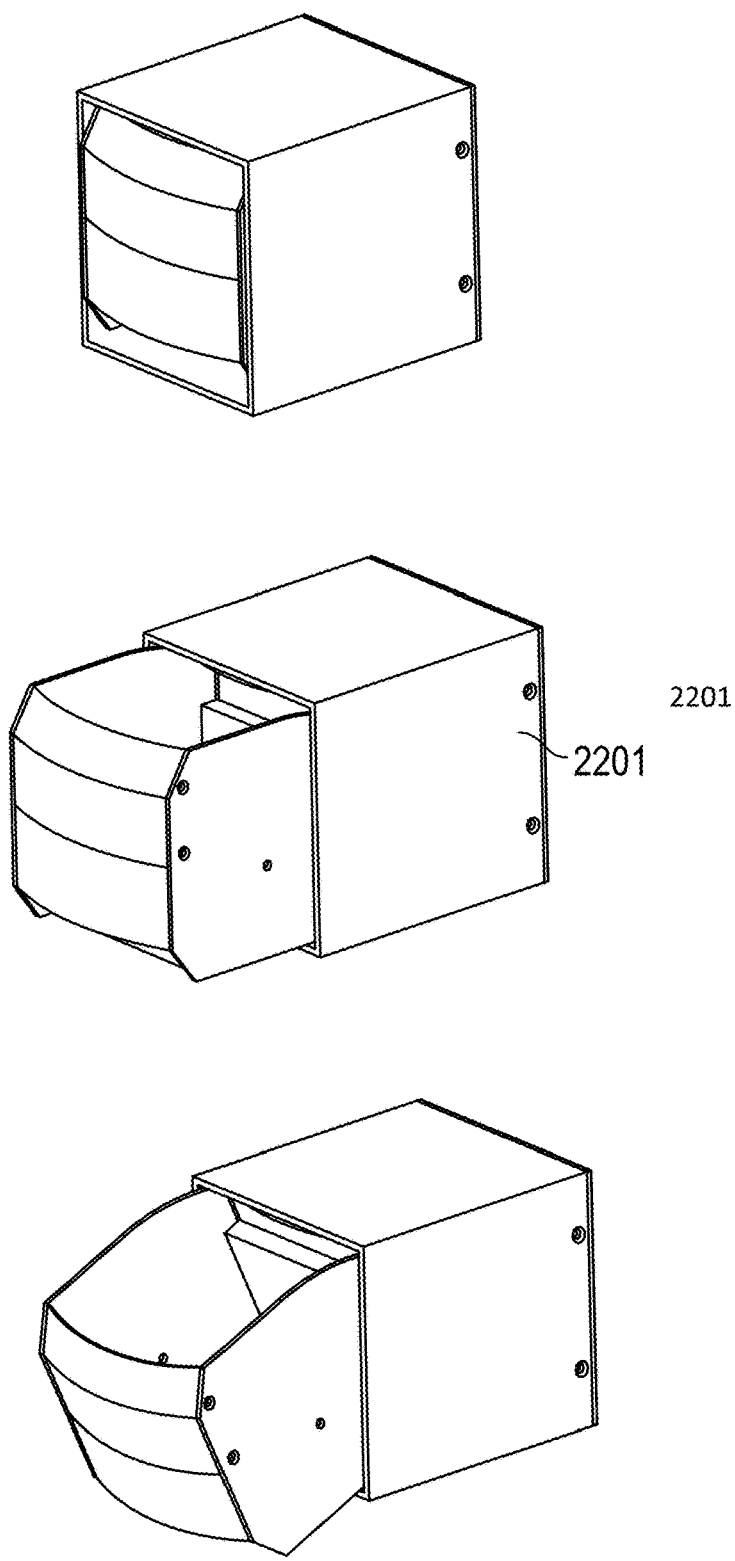
FIG. 33 depicts an example slimline storage assembly, according to various aspects of the subject technology.

FIG. 33 depicts an example slimline storage assembly, according to various aspects of the subject technology. In the depicted example, a handle feature is incorporated into the storage bin. The storage bin may be pulled from the housing, and may tilt and/or rotate after reaching a predetermined location. In certain implementations, one or more of the following features may be included: (1) The boarder frame contains the storage bin locking mechanism. (2) The bin subassembly frame does not contain a latch. (3) The storage bin has features that interact with the latch. (4) The bin locking is done by a latching mechanism that is part of the boarder frame. (5) The boarder frame latch can consists of horizontal rotating rod and a vertical rotating rod.

Figure 34A:
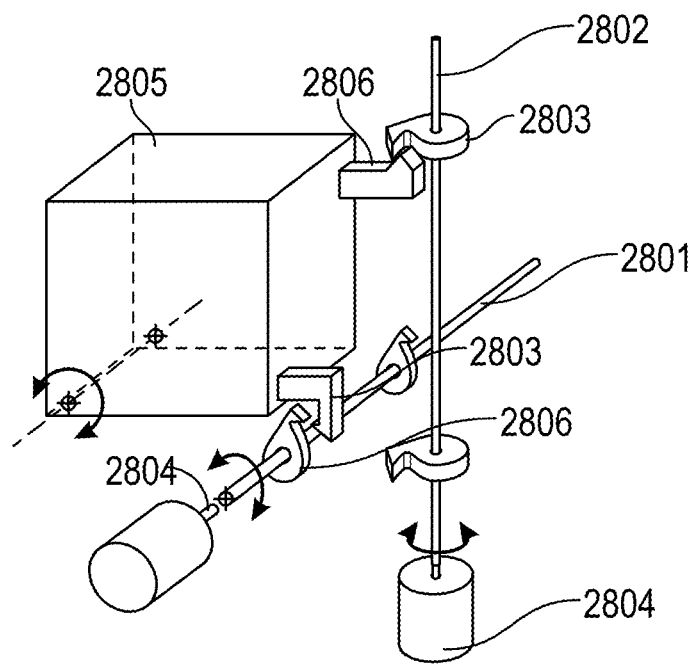
FIGS. 34A and 34B depict an example storage bin latching mechanism, according to various aspects of the subject technology.
Figure 34B:
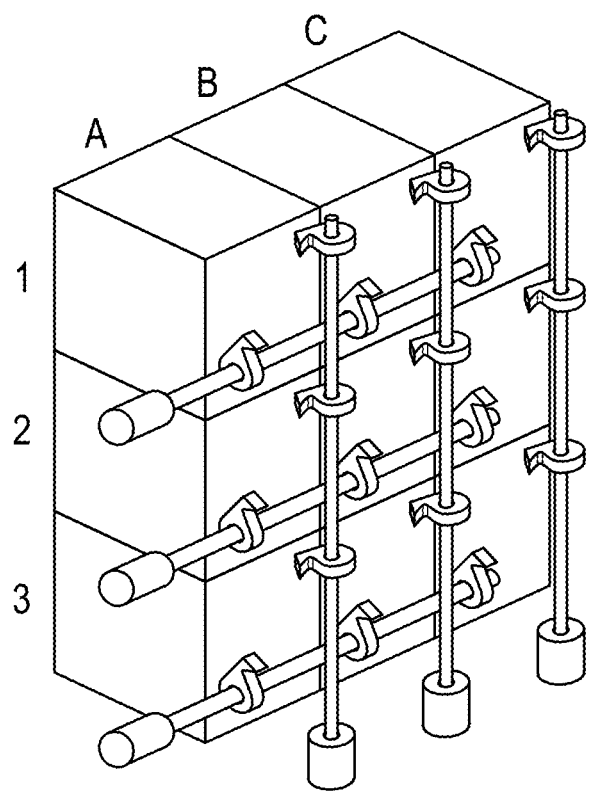

FIGS. 34A and 34B depict an example storage bin latching mechanism, according to various aspects of the subject technology. In the depicted example of FIG. 34A, rods 2801, 2802 are implemented within the housing 2201, and have latch features 2800 on them the allow it to lock and unlock the storage bin. In this regard, the bin may be released when both the horizontal and vertical latches are in the open position.

Figure 35:
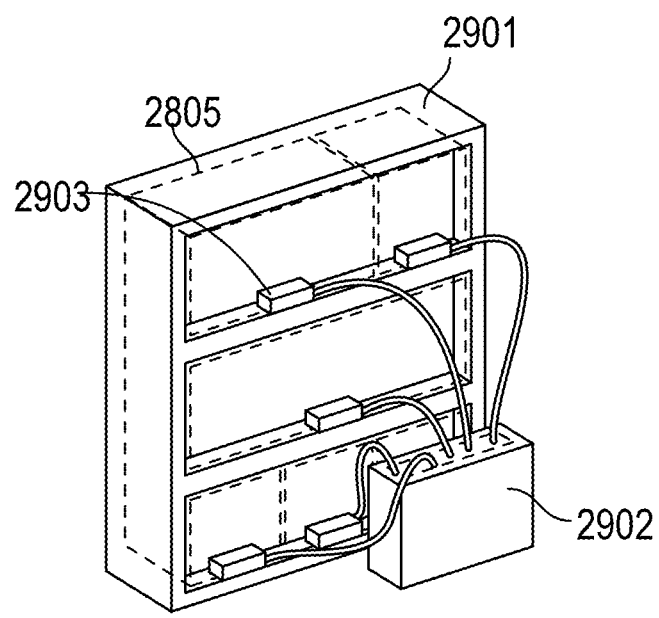
FIG. 35 depicts a rear view of an example slimline frame with a latch control module, according to various aspects of the subject technology.

As depicted in FIG. 34B, the boarder frame assembly may include three horizontal rod assemblies 2801 and three vertical rod assemblies 2802. Each rod assembly may include three latches 2803 and an actuator 2804. A 3×3 array may include nine horizontal latches, nine vertical latches and six actuators. With the depicted example, up to nine storage bins 2805 may be independently unlocked with the horizontal and vertical rod assemblies arranged in an 3×3 array. FIG. 35 depicts a rear view of an example slimline frame 2901 with a latch control module 2902, according to various aspects of the subject technology. In implementations according to FIG. 35, one or more of the following features may be included: (1) The bin frame 2901 contains the storage bin locking mechanism. (2) The bin subassembly frame 2901 does not contain a latch. (3) The bin frame includes a latch controller module. The latch controller module has a connector ports to accommodate up to nine latches. The latch control module contains electronic hardware to operate up to 9 latches independently. (4) Each latch is positioned and mounted to the frame as needed to control its mating bin. (5) Each storage bin has at least one hook 2806 that interfaces with a corresponding latch. (6) Each latch is connected to the latch control module.

Connected Bin Inventory Tracker

Another aspect of the disclosure relates to a smart touch to retrieve system and corresponding methods for inventory management of items in both non-acute and acute care settings. The disclosed touch to retrieve system includes a wireless connected device which interfaces to a gateway and an enterprise level inventory management application. A connected bin inventory tracker within the touch to retrieve system may provide configurable buttons, display and multi-color LEDs as a user interface. The touch to retrieve system may be used in a multitude of locations where medication and supplies need to be managed including med rooms, med carts, supply rooms, operating rooms, emergency rooms, and intensive care units. In some implementations, all or part of the touch to retrieve system is placed inside refrigerators to manage refrigerated items. In some implementations, the touch to retrieve system includes a mobile device used for location tracking of items within the hospital. In some implementations, the disclosed system and device and corresponding method implements machine learning (ML) inference and data analytics to optimize power consumption on the touch to retrieve system or a connected bin inventory tracker included therein based on its awareness of usage context. In some implementations, the disclosed system and device and corresponding method includes handheld device or mobile application that can scan multicolor led and identify system status during manufacturing or field. The disclosed system and device and corresponding method is an enterprise level solution that provides inventory management and location tracking of items in a multitude of use cases.

Existing solutions for inventory management in non-acute care settings is performed manually and is not accurate. A connected bin inventory tracker may be attached to off the shelf bins or smart bins and provides a screen and buttons for user interaction. The configurable display can show the item name and quantity available and buttons are used to increment or decrement quantities. The user interface is configurable to enable other functionality such as automated loading and guide by light to aide in finding items. The connected bin inventory tracker is connected to an enterprise level medication management software which enables end to end inventory management.

The disclosed smart touch to retrieve technology has two-way communications which enables a multitude of functionalities including guide by light and display updates.

The connected bin inventory tracker, in some implementations, may include a mobile device which may be used for tracking of items. In asset tracking mode the connected bin inventory tracker may beacon its unique ID over the wireless interface, for location tracking of mobile bins and containers.

In some implementation, the connected bin inventory tracker is a stationary device attached to bins in open shelf inventory locations or behind cabinets/locks.

In some implementations, the connected bin inventory tracker is located inside refrigerators. The connected bin inventory tracker may be fashioned of material hardened to withstand refrigerated environments.

In some implementations the connected bin inventory tracker is a mobile device used for asset tracking of items.

Figure 36:
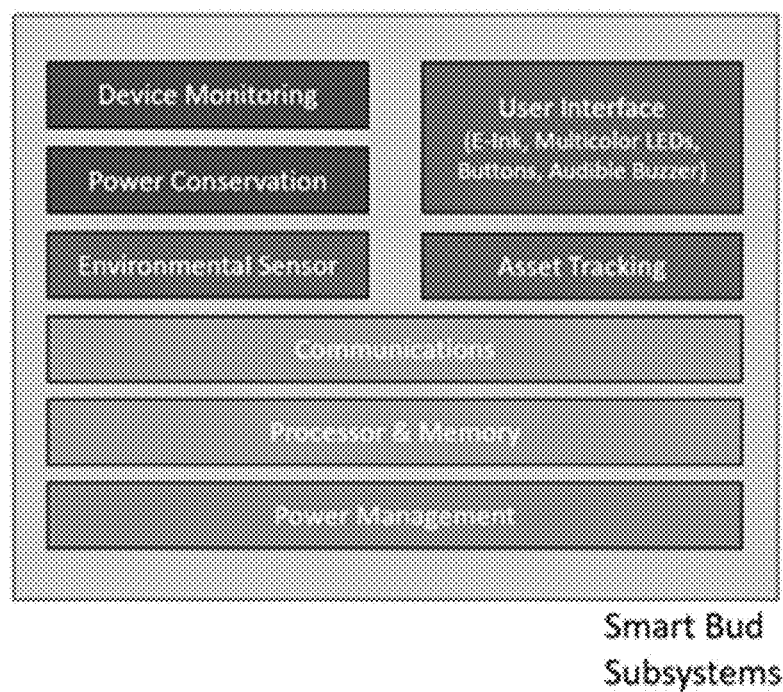
FIGS. 36 and 37 depict components of the disclosed connected bin inventory tracker system and/or device, according to some aspects of the subject technology.

With brief reference to FIG. 36, the disclosed system and/or device may include an E-ink user interface. In some implementations, the user interface may display status of the connected bin inventory tracker using icons such as battery level, network connectivity, and/or status of the latch and door. In some implementations, the user interface may display alerts such as expired medication, below par, tamper detection etc. In some implementations, the user interface may display information collected from the environmental sensor. For example, the user interface may display information such as temperature of medication, monitor tamper evidence sensor signal, humidity, shock and vibration over time. In some implementations, the user interface may display item name and item quantity. In some implementations, the contents of the display is configurable by the user.

In some implementations, the user interface may include buttons that have different functionality depending on the context:

Example 1: In remove workflows the buttons function as decrement and increment quantity of the items Example 2: In load workflows the buttons function as Accept/Reject quantities Example 3: In other workflows buttons are used to navigate through menus of E-Ink In some implementations, the user interface may function as a glanceable status indicator. For example, LED color, flash pattern and intensity may indicate different status based on user accessing the secure storage location and workflow.

Example 1: During medication loading workflow, the LED lighting can guide the user to the medication at a glance.

Example 2: If the medications being secured or monitored by the connected bin inventory tracker has expired, the LED can flash red or other predetermined color.

Example 3: During medication audit, the system may guide by lighting the LEDs so the user can identify the med easily.

Example 4: If the battery level lower than threshold led can flash in low intensity.

Example 5: LED color and flash pattern to indicate authorized user unlocked the latch.

Example 6: Specific LED colors assigned to users who are using the system simultaneously. For example, two users with different pick lists access the system at once; the connected bin inventory trackers for user 1 may flash one color and the connected bin inventory tracker s for user 2 may flash a different color.

In accordance with the above system and/or device, disclosed is a method by which a handheld device may scan the LED color, intensity, and flash pattern and identify its status during manufacturing or in field.

The foregoing system and/or method may include use of an inspection equipment or a mobile application. For example, an optical reading device may be implemented to read the multicolor visual indicator and obtain the failure modes and conditions on a connected bin inventory tracker.

Access to a connected bin inventory tracker may be authenticated via remote authentication. For example, users can enter credentials at tablet or PC or use a standalone authentication module to perform load workflow or reconfigure the connected bin inventory tracker. If a user loses their badge or smartphone the super user can provide remote authentication.

The system, device, and/or method may include producing an audible sound indicating user actions such as when an actuator command is been executed. For example, the audible sound may be produced by a piezo beeper with different tones to indicate different actions.

In some implementations, the system, device, and/or method may include an environmental sensor interface system that is capable of monitoring NIST traceable temperature sensors used for cold storage of vaccines. The environmental sensor interface system may be capable of monitoring plurality of sensors including: temperature, humidity, vibration, orientation and acceleration of the connected bin inventory tracker.

In some implementations, the system, device, and/or method may include a tamper detection system that detects tamper via the foregoing environmental sensors and/or additional sensors (e.g. optical and electromagnetic sensors).

In some implementations, the system, device, and/or method may include a communication and power subsystem that supports a distributed architecture. In such implementations, each connected bin inventory tracker may include its own wireless communication interface and power source.

In some implementations, the communication and power subsystem may support a central architecture where multiple connected bin inventory trackers are wired to a single controller. The controller may provide wireless communications and/or power source for multiple connected bin inventory trackers. In such implementations, the number of wireless communication interfaces, electronics and power sources may be reduced, which may be desirable in cases where many connected bin inventory trackers are co-located.

The system, device, and/or method may include communication architecture (CA), which may use plurality of PAN protocols such as (802.15.4/BLE) to talk to the remote device. In this regard, the system, device, and/or method may utilize the CA to achieve one or more of the following features: beacon for asset tracking; environmental sensor and tamper detection monitoring; Real time and offline mode support; and tote content identification and inventory tracking. In some implementations of a connected bin inventory tracker, the CA may bypass hospital IT, thereby reducing implementation time (e.g., implementing a drop ship model based on PAN protocol support).

The system, device, and/or method may include power architecture that implements disposable batteries or rechargeable batteries.

The system, device, and/or method may include an energy harvesting system that uses plurality of sources to increase connected bin inventory tracker operation life. In some implementations, the system, device, and/or method may include piezo transducers interfaced to buttons or electromagnetic induction from lock actuator or drawer/door open and close action or wireless energy from RF sources to harvest energy.

The system, device, and/or method may include a power management subsystem for conserving power in battery operated devices based on system factors and user preference. In this regard, a method for conserving power may include placing devices in various low power states to wake up periodically (wake up period) and enable radio communications and check in with a gateway/hub for updates or to perform transactions. Power saving states may adjust device responsiveness versus power savings. The low power states and wake up period may be configured by the gateway/hub for devices based on system usage factors and user preferences.

In some implementations, the power states may be adjusted based on user presence, if users are present, the devices are placed in more responsive states in anticipation of the system being used. If users are not present, the devices are put in less responsive states, to maximize power savings.

In some implementations, the power states may be adjusted by machine learning algorithms running on the hub/gateway and/or cloud.

In some implementations, the user presence may be detected in plurality of methods including users logging into the system, by occupancy sensors such as motion, radar, and proximity sensors. Occupancy sensors are envisaged to be powered devices located in the med room area and interface to the gateway/hub.

In some implementations, the users input office schedule into the system and power states are adjusted based on this schedule.

In some implementations, the system, device, and/or method uses microphones with key word activation to wake up the device from deep sleep mode.

In some implementations, the system, device, and/or method may include sensors which monitor health of a device (e.g., including the foregoing environmental sensors) and additional sensors monitoring the operation of the device such as currents, voltages, temperatures of critical components, etc.

In some implementations, the system, device, and/or method may include a device monitoring subsystem that transmits collected data to the hub/gateway/cloud for analytics.

In some implementations, the system, device, and/or method may include an asset tracking subsystem wherein the connected bin inventory tracker is placed inside or affixed to the outside of off the shelf containers such as totes to convert them to a trackable container. In some implementations, an asset tracking subsystem plays a beacon role, advertising its unique ID, so it may be identified and located for asset tracking by hubs or mobile devices.

Unique ID and configuration information including contents of the container may be stored locally on the device in non-volatile memory. This information is also available on an online database.

A device including the asset tracking subsystem may be tracked by hubs which are in areas of interest. As the device moves hubs located in the area may be able to read the beacon and identify the device. Hubs are placed in areas of interest such as shipping and receiving, staging areas, hallways etc. Beacons may also be read by mobile devices. In some implementations, an asset tracking enabled device may be queried directly by hubs or mobile devices for additional information such as contents of connected bin inventory tracker, destination, battery level, environmental sensors etc. Alternatively, the mobile device and/or hubs are network connected and may be configured to retrieve information about the connected bin inventory tracker from a network database using the beacons unique ID. In some implementations, wireless signal characteristics may be used to locate and guide the user to specific connected bin inventory tracker(s). This may be useful in scenarios where a specific device needs to be located and a user may be guided to the unit they are looking for.

The following commentary and illustrations define a solution for dispensing items.

The connected bin inventory tracker may be a modular "Internet of Things" (IOT) device that may be attached to a bin. In some implementations, a user can keep track of inventory by using a "take" button or "return" button. The items description, quantity, etc. may be shown on the e-ink display. The IOT connected bin inventory tracker may communicate wirelessly with other devices. (See FIGS. 1B and 1C.)

The IOT connected bin inventory tracker (see FIGS. 1B and 1C) may include an e-ink display, take/return buttons, multi-colored LED indicator, and external snap-on battery access cover for easy access.

The IOT connected bin inventory tracker may use common batteries such as AAA batteries.

The IOT connected bin inventory tracker may be configured to withstand a refrigerated environment. The material and components may be used at lower temperatures. The IOT connected bin inventory tracker may be placed in a refrigerator.

The IOT connected bin inventory tracker have overlapping features, interlocks and materials to indicate tamper evidence.

Figure 37:
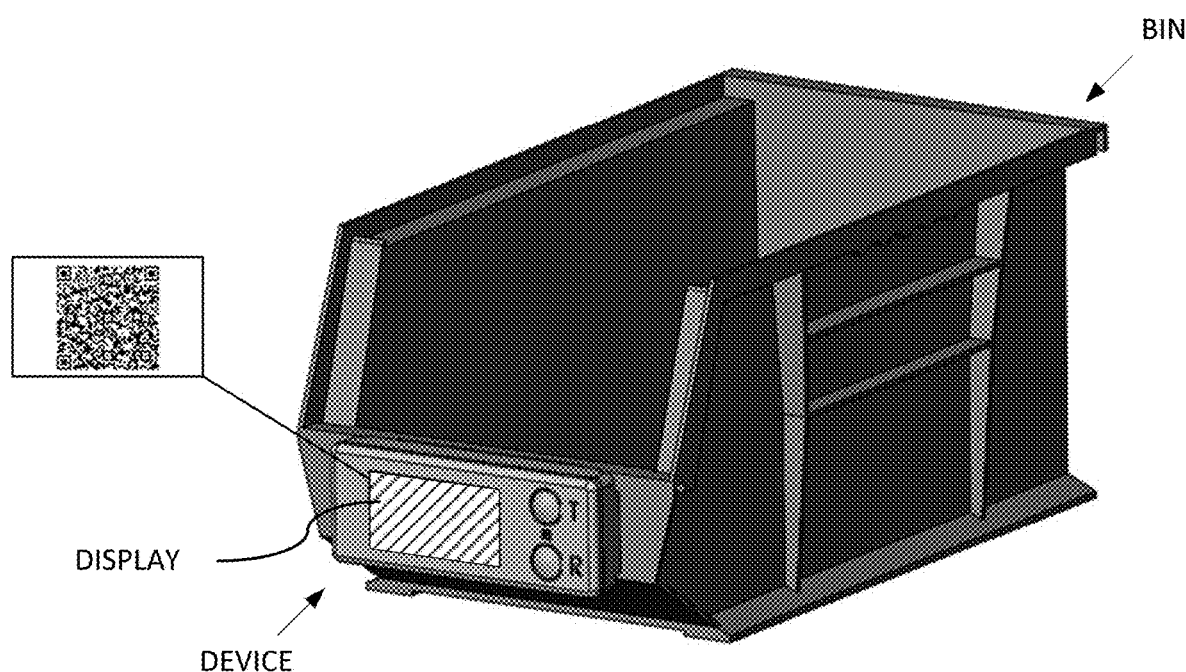

The IOT connected bin inventory tracker housing may include clip-on features with a push button clip and may be attached to off-the-shelf bins. (See FIG. 37.)

Modular Dispensing Bin

Another aspect of the disclosure relates to a smart bin or tote system, device, and/or corresponding methods which provide secure access and transport of items including medications and supplies (the "smart bin"). The disclosed smart bin may be configured for controlled, non-controlled, refrigerated and non-refrigerated items in both acute and non-acute health care settings. The disclosed smart bin may be configurable to allow the different authentication requirements of both regulatory bodies and hospitals.

The disclosed smart bin may provided in multiple sizes to accommodate different items and is stackable to optimize storage locations. The disclosed smart bin may be a wireless connected device connected to a gateway and connects to an enterprise level application. According to various implementations, users may authenticate using remote authentication methods (such as a tablet or standalone authentication modules) and a secure and traceable access is provided to the smart bin. The disclosed smart bin may include one or more user interfaces that include multi-color LEDs, E-Ink display, buttons and audible buzzers. In some implementations, smart bin may include a machine learning (ML) inference and data analytics to optimize power consumption on smart bin based on its awareness of usage context. In some implementations, the disclosed system, device, and/or method includes a handheld device or mobile application that can scan multicolor led and identify system status during manufacturing or field.

The disclosed smart bin and related systems and method may include implementation of an enterprise level solution that provides traceability and inventory tracking of item in a multitude of use cases.

Secured storage for controlled medications involve off the shelf keyed or combination lock bins that are placed on countertops or inside cabinets and drawers. Users may use the same key or combination numbers to access medication. However, these solutions are not traceable as to who accessed the medication. Additionally, tracking of inventory in non-acute care settings is performed manually and is not accurate. The smart bin described herein provide secure traceable access to these medications. The smart bin may also provide a display screen to indicate quantity and buttons for users to increment or decrement quantities, and may be connected to an enterprise level medication management software which enables end to end inventory management.

According to some implementations, the disclosed smart bin is configured to be placed inside refrigerators to provide secure access and inventory management to refrigerated medications. In some implementations, the smart bin may be configured as a mobile device which may be used for secure transport of medication. A secure bin may be used on its own or placed inside the previously described smart tote for secure transport. The smart bin may be configured to beacon its unique ID over the wireless interface and is used for location tracking of the bins.

In some implementations, the smart bin is a stationary device located in medication rooms, at a bedside of the patient, or at other care locations. In some implementations, the disclosed smart bin is located inside refrigerators. The disclosed smart bin may be configured to be hardened to withstand refrigerated environments. In some implementations, the disclosed smart bin is a mobile device used for secure transport of items. The disclosed smart bin may include a plurality of user interfaces which enables an enterprise solution for securing one or more items and guide the loading of the item(s).

Figure 38:
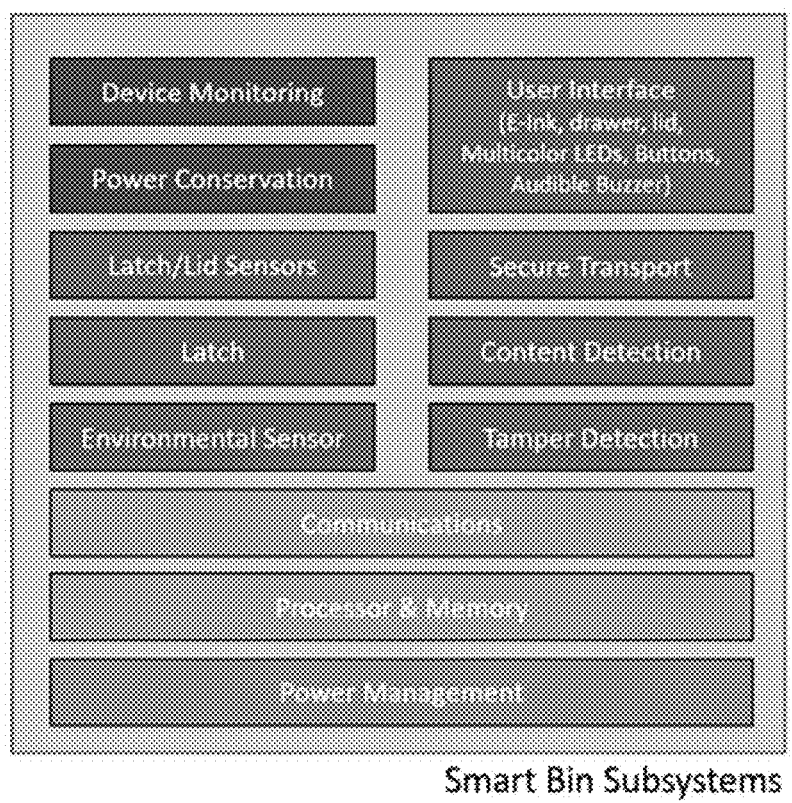
FIG. 38 depicts example subsystems of the disclosed smart bin system and/or device, according to various aspects of the subject technology.

FIG. 38 depicts example subsystems of the disclosed smart bin system and/or device, according to various aspects of the subject technology. As depicted in FIG. 38, the disclosed system and/or device may include an E-ink user interface. In some implementations, the user interface may display status of the disclosed smart bin using icons such as battery level, network connectivity, and/or status of the latch and door. In some implementations, the user interface may display alerts such as expired medication, below par, tamper detection etc. In some implementations, the user interface may display information collected from an environmental sensor. For example, the user interface may display information such as temperature of medication, monitor tamper evidence sensor signal, humidity, shock and vibration over time. In some implementations, the user interface may display item name and item quantity. In some implementations, the contents of the display is configurable by the user.

In some implementations, the user interface may include one or more buttons that are used to decrement and increment quantity of the item. In some implementations, the user interface may function as a glanceable status indicator. For example, LED color, flash pattern and intensity may indicate different status based on user accessing the secure storage location and workflow.

Example 1: During medication loading workflow the led lighting may guide the user to the medication at a glance.

Example 2: If the medications being secured by the Smart bin has expired the LED can flash red.

Example 3: During medication audit the system may guide by lighting the LED's so the user can identify the med easily.

Example 4: If the battery level lower than threshold led can flash in low intensity Example 5: Led color and flash pattern to indicate authorized user unlocked the latch.

In some implementations, the disclosed smart bin system may include or embody a handheld device that may scan the led color, intensity and flash pattern, and identify its status during manufacturing or in field. In some implementations, the Smart bin system may include inspection equipment or a mobile application, and/or an optical reading device to read the multicolor visual indicator and to obtain the failure modes and conditions on smart bin.

Access to disclosed smart bin may be authenticated via remote authentication. For example, users can enter credentials at tablet or PC or use a standalone authentication module to gain access to the disclosed smart bin. If a user loses their badge or smart phone the super user may provide remote authentication.

In some implementations, the disclosed smart bin may be configured to produce an audible sound that indicates user actions such as when an actuator command is been executed. In some implementations, the disclosed smart bin includes a piezo beeper is used with different tones to indicate different actions.

In some implementations, the disclosed smart bin may include an environmental sensor interface system. In some implementations the environmental sensor interface system may be capable of monitoring NIST traceable temperature sensors used for cold storage of vaccines. In some implementations the environmental sensor interface system may be capable of monitoring plurality of sensors including: temperature, humidity, vibration, orientation and acceleration of the smart bin.

In some implementations, the disclosed smart bin may include a tamper detection system. The tamper detection system may be configured to detect tamper via the foregoing environmental sensors and/or additional sensors (e.g. optical and electromagnetic sensors) located on the latch, drawer and lid which detect unauthorized access to contents of smart bin.

In some implementations, the disclosed smart bin may include a content detection subsystem. The content detection subsystem may utilize the sensor interface to automatically identify the quantity of contents inside smart bin. In some implementations, the disclosed smart bin may support a sensor interface such as load cell, optics with a led & photodiode, acoustics or RF to sense the quantity of content inside the bin. In some implementations, the disclosed smart bin may support a coarse level of identification used for auto-detection PAR levels.

In some implementations, the disclosed smart bin may include a power subsystem. The power subsystem may be configured to support a distributed architecture where each bin has its own wireless communication interface and power source. In some implementations, the power subsystem may include a central architecture where multiple bins are wired to a single controller. The controller may provide wireless communications and power source for multiple bins. Accordingly, the number of wireless communication interfaces, electronics and power sources may be reduced, which may be desirable in cases where many bins are co-located (i.e. multiple bins stacked inside one cabinet).

The disclosed system, device, and/or method may include a communication architecture (CA). In some implementations, the CA may be configured with a plurality of PAN protocols such as (802.15.4/BLE) to talk to a remote device. A method that utilizes the CA may include one or more of the following features: beacon for asset tracking; real time and offline mode support; environmental sensor and tamper detection monitoring; content identification and inventory tracking. In some implementations, the smart bin (e.g., using CA) may bypass hospital IT, thereby reducing implementation time (e.g., implementing a drop ship model based on PAN protocol support).

According to various implementations, the disclosed smart bin may be configured to act as a companion device for devices placed inside the enclosure to bridge communications. Connected devices placed inside enclosures, such as refrigerators and metal cabinets, may have their radio signals attenuated and have difficulty communicating to hubs located further away. Accordingly, the smart bin may be used as companion device to enable reliable communication to a hub/gateway. The smart bin when acting as a companion device may play two roles: (1) A slave role communicating to the hub; and (2) A master role communicating to the devices behind the enclosure. As discussed previously with regard to FIG. 12, the foregoing creates a multi-level network hierarchy in the network of devices all communicating back to the hub either directly or through another device.

In some implementations, the disclosed smart bin system and/or device may include a power architecture (PA). In some implementations, the PA may be configured to use disposable batteries or, in some implementations, rechargeable batteries.

In some implementations, the disclosed smart bin system, device, and/or corresponding method may be configured for energy harvesting using a plurality of sources to increase smart bin operation life. In some implementations, the smart bin may be configured with piezo transducers interfaced to buttons or electromagnetic induction from lock actuator or drawer/door open and close action or wireless energy from RF sources to harvest energy. In some implementations, the disclosed smart bin system and/or device may include a power management subsystem that conserves power in battery operated devices based on system factors and user preference. In this regard, a method for conserving power may include placing devices in various low power states to wake up periodically (wake up period) and enable radio communications and check in with a gateway/hub for updates or to perform transactions. Power saving states may adjust device responsiveness vs power savings. The low power states and wake up period may be configured by the gateway/hub for devices based on system usage factors and user preferences.

In some implementations, power states may be adjusted based on user presence, if users are present the devices are placed in more responsive states in anticipation of the system being used. If users are not present the devices may be put in less responsive states, to maximize power savings In some implementations, the smart bin may detect user presence. For example, smart bin may detect users logging into the system, by occupancy sensors such as motion, radar, and proximity sensors. Occupancy sensors may be configured to be powered devices located in the med room area and interface to the gateway/hub.

In some implementations, the disclosed system may receive user input of office schedule into, and power states may be adjusted based on this schedule. In some implementations, the disclosed system may use microphones with key word activation to wake up the device from deep sleep mode. In some implementations, power states may be adjusted by ML algorithms running on the hub/gateway and/or cloud.

In some implementations, the disclosed smart bin system and/or device may include a monitoring subsystem. The monitoring subsystem may include or interface with sensors which monitor health of the device including the environmental sensors, and/or additional sensors monitoring the operation of the device such as currents on motors, voltages, temperatures of critical components, etc.

In some implementations, the monitoring subsystem may be configured to transmit collected data to the hub/gateway/cloud for analytics. In some implementations, the disclosed smart bin system and/or device may include a secure transport subsystem. The secure transport subsystem may be configured to facilitate use of the smart bin for secure transport of item.

In some implementations, the smart bin may be used as a standalone transport or may be placed inside a tote (e.g., the disclosed smart tote). In some implementations, the smart bin may be configured to play a beacon role, advertising its unique ID, so it may be identified and located for asset tracking by hubs or mobile devices. Unique ID and configuration information, including contents of the smart bin, may be stored locally on the device in a non-volatile memory. This information may also be made available to an online database (e.g., for retrieval view an online network).

In some implementations, the secure transport smart bin may be configured to be tracked by hubs which are in areas of interest. As the device moves. hubs located in the area may be able to read the beacon and identify the device. For example, hubs may be placed in areas of interest such as shipping and receiving, staging areas, hallways etc. In some implementations, the beacons may be read by mobile devices. In some implementations, the secure transport smart bin may be queried directly by hubs or mobile devices for additional information such as contents of smart bin, destination, battery level, environmental sensors etc. Alternatively, the mobile device and/or hubs may be network connected and may be configured to retrieve information about the smart bin from a network database using the beacons unique ID.

In some implementations, the secure transport smart bin may be configure to implement wireless signal characteristics, which may be used to locate and guide a user to the smart bin modules. This may be desirable where a specific device needs to be located and a user may be guided to the unit they are looking for.

Figure 39:
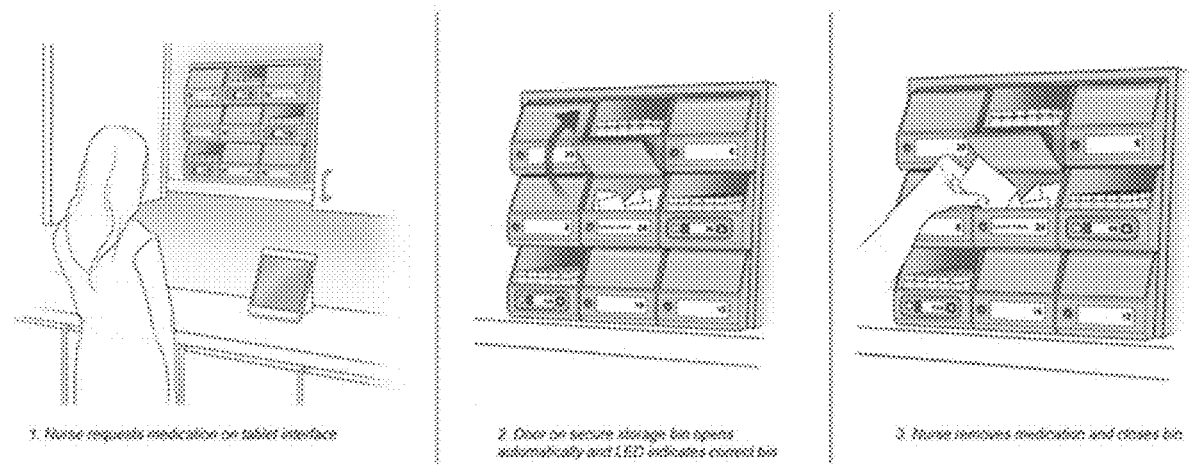
FIG. 39 depicts an example smart bin system for dispensing items, according to various aspects of the subject technology.

FIG. 39 depicts an example smart bin system for dispensing items, according to various aspects of the subject technology. In various implementations, the smart bin system and/or device(s) may be configured as a singular, stackable and secure modular bin, for item storage and retrieval. A smart bin may communicate wirelessly with other devices, and may be configured to record user access.

The smart bin system and/or device(s) may be configured to withstand a refrigerated environment, and may include material and components that may be used at cold temperatures. The smart bin system and/or device(s) may be placed in a refrigerator and may support optional sensors for temperature and humidity. The smart bin system and/or device(s) may be configured with overlapping features and interlocks to prevent diversion. The smart bin system and/or device(s) may be designed to indicate an user's attempt to divert. The smart bin system and/or device(s) may be formed of or include material that may be deformed showing taper evidence. Additionally or in the alternative, the smart bin system and/or device(s) may include a hook configured to break and leave a piece in the latch making it unusable thereby indicating a break-in.

Figure 40A:
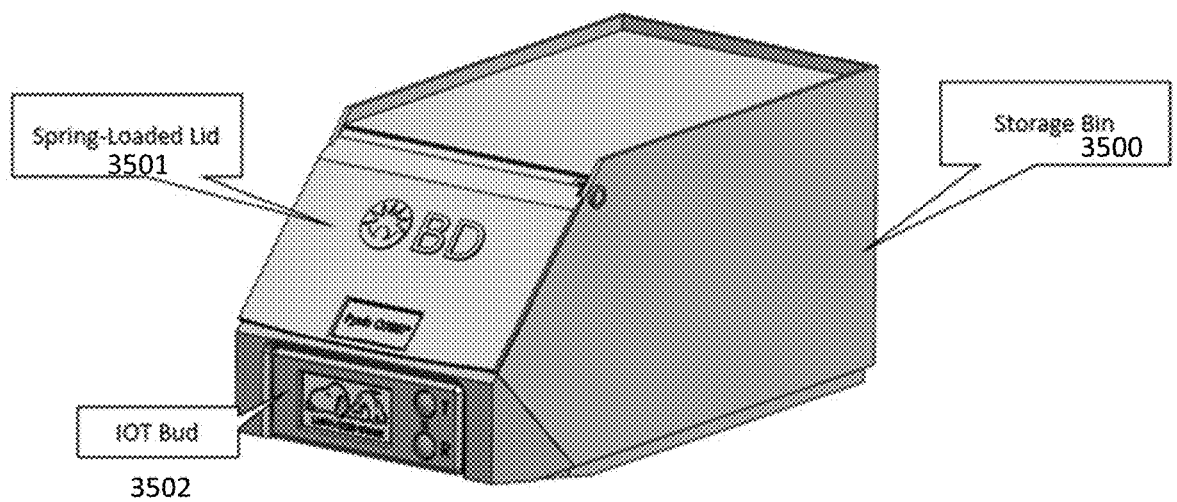
FIGS. 40A, 40B, and 40C depict example stackable smart bins for dispensing items, according to various aspects of the subject technology.
Figure 40B:
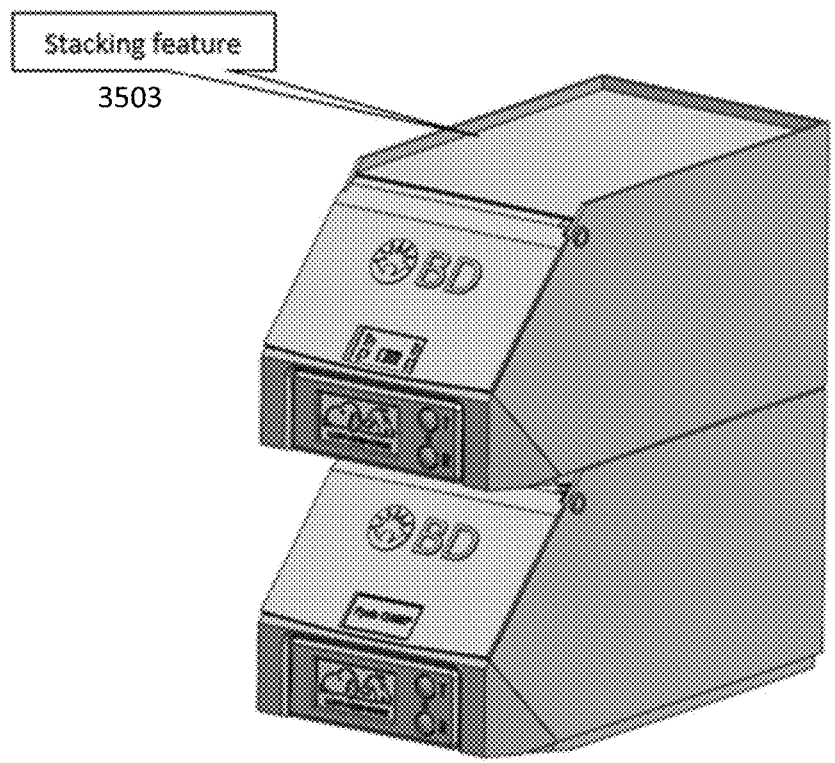
Figure 40C:
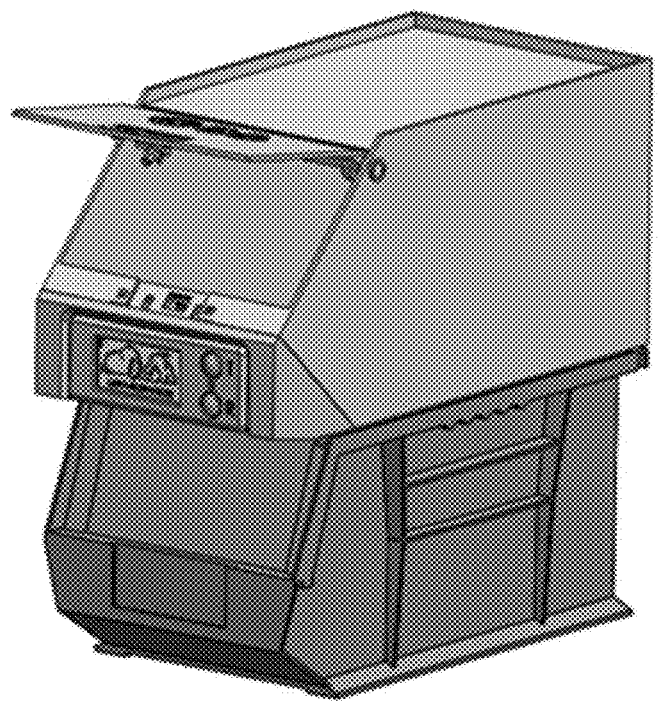

FIGS. 40A, 40B, and 40C depict example stackable smart bins 3500 for dispensing items, according to various aspects of the subject technology. According to some implementations, the smart bin system and/or device(s) may be fully enclosed. The smart bin system and/or device(s) may include the five-sided container storage bin, electro-mechanical latch, PCBA, battery, spring-loaded lid 3501, one or more LEDs, IOT connected bin inventory tracker 3502, features that allow it for stacking, features that allow it to be mounted to securing frame, barcode, load cell for take-by-weight. An IOT connected bin inventory tracker may be configured to communicate wirelessly to the smart bin system and/or device electronics.

As depicted in FIGS. 40B and 40C, The smart bin may be stacked. The size of the smart bin storage container may be configured (e.g., with a stacking feature 3503) to be stacked on top of or to interconnect with current bin suppliers (see FIG. 40C). As depicted in the figures, smart bin may be stacked on top of each other and may be stacked with current storage bins. The smart bin may be designed to indicate the attempt to divert. The smart bin may include material that may be deformed showing taper evidence. The disclosed latch hook may break and leave a piece in the latch making it unusable thereby indicating a break-in.

Figure 41:
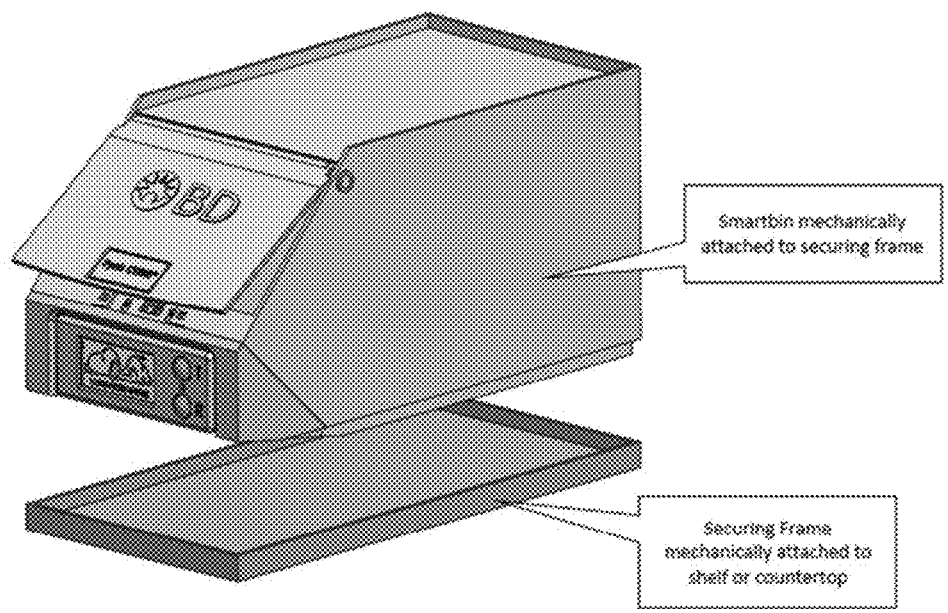
FIG. 41 depicts an example smart bin mechanically attached to an example securing frame, according to various aspects of the subject technology.

FIG. 41 depicts an example smart bin mechanically attached to an example securing frame, according to various aspects of the subject technology. A securing frame may be securely mounted to a counter, cabinet shelf or refrigerator shelf. The securing frame may interface with the smart bin storage bin features. The smart bin may be configured to be locked to the securing frame using a latch or key lock. Locking the smart bin to the securing frame may deter diversion and may indicate tamper evidence.

Figure 42:
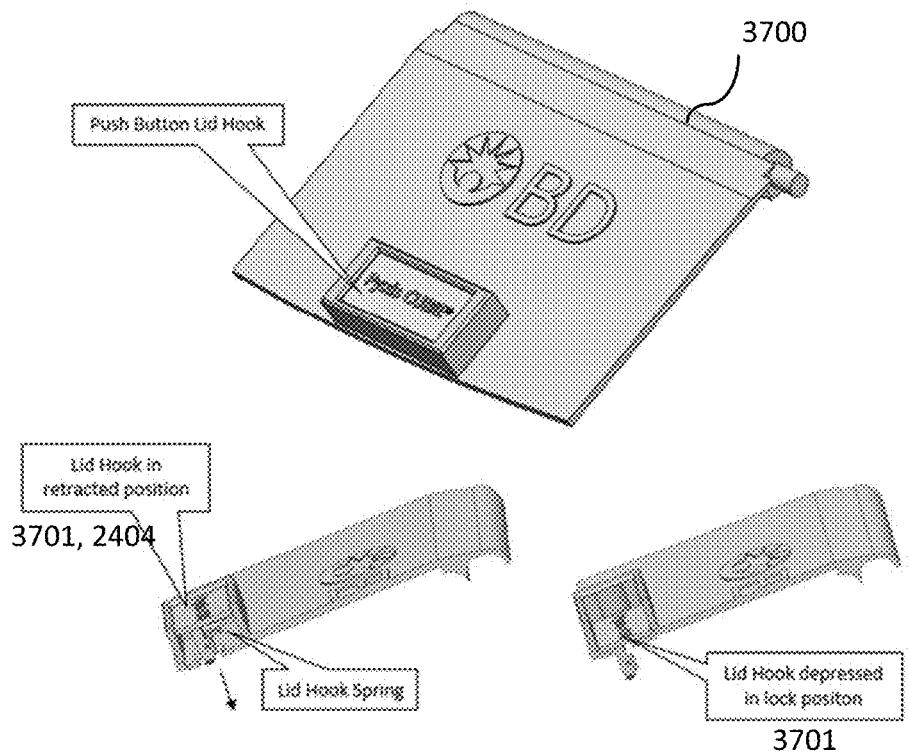
FIG. 42 depicts various examples of a smart bin lid, according to various aspects of the subject technology.

FIG. 42 depicts various examples of a smart bin lid, according to various aspects of the subject technology. In some implementations, the smart bin lid 3700 may mount a hook part 3701, 2404 that interfaces with the latch. The hook part 3701, 2404 may be spring loaded and retract in order to create a clear path for the users hand to content access. The hook part may be used as a "button" do depress in order for it to engage the latch when the lid is closed.

Figure 43A:
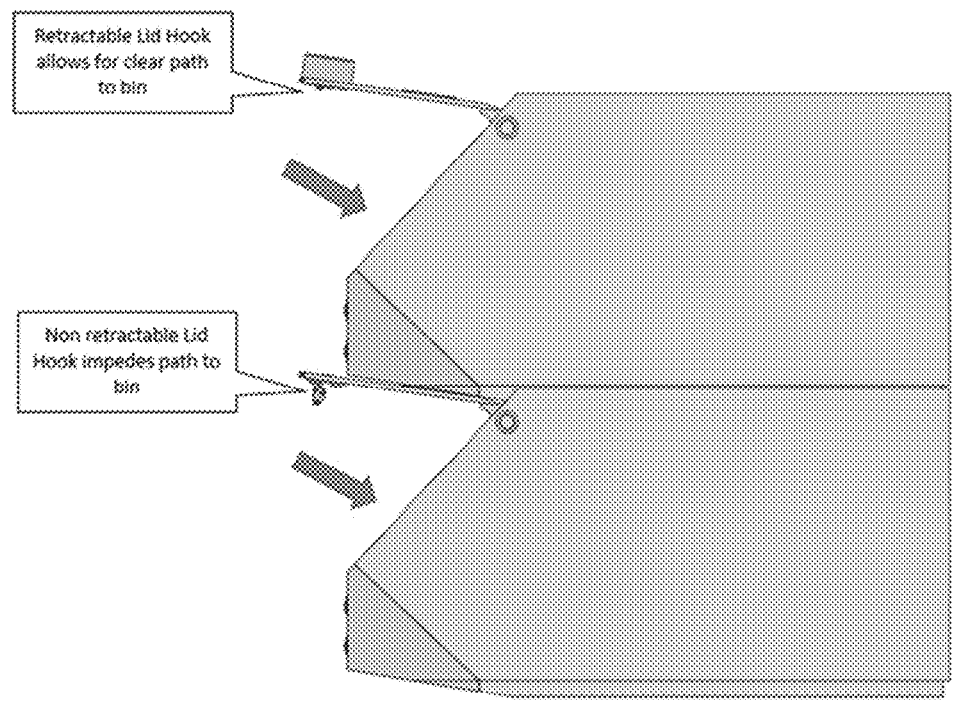
FIGS. 43A and 43B depict cut-away side views of example smart bins and corresponding lids, according to various aspects of the subject technology.
Figure 43B:
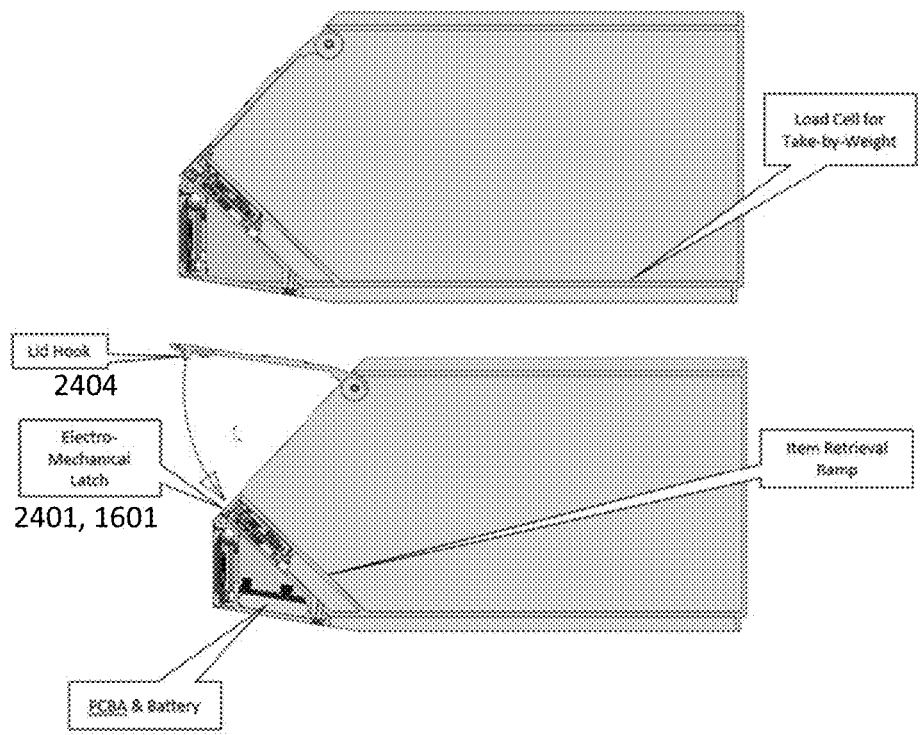

FIGS. 43A and 43B depict cut-away side views of example smart bins and corresponding lids, according to various aspects of the subject technology. FIG. 43A depicts an example difference between a push button retractable lid hook and a non-retractable lid hook. In the example figures, the lid of the smart bin pivots open and closed. Opening the lid provides access to the smart bin's contents. The lid may be spring loaded. In some implementations, the smart bin container may include an electro-mechanical latch. The latch may be battery operated. The battery may be recharged using an electrical wall outlet. The battery may easily be replaced. (See FIG. 43B.) The storage bin may include features on it to mount the latch. The storage bin may incorporate a ramp to help with the containment and removal of items.

FIG. 43B depicts cut-away side views of example smart bins and corresponding lids configured with a lid hook that engages with a electro-mechanical latch, according to various aspects of the subject technology. In addition to the foregoing lidded concept, the smart bin may be further adapted as follows: (1) In some implementations, the smart bin may include a pull-out Drawer that allows the user to easily retrieve and see the contents, and which aids a blind count workflow. (2) In some implementations, the smart bin may not include a lid, but instead include a lockable drawer. In these implementations, the smart bin may include an Outer Housing, Drawer, window, electro-mechanical latch, PCBA, battery, LEDs, spring, IOT connected bin inventory tracker.

Figure 44A:
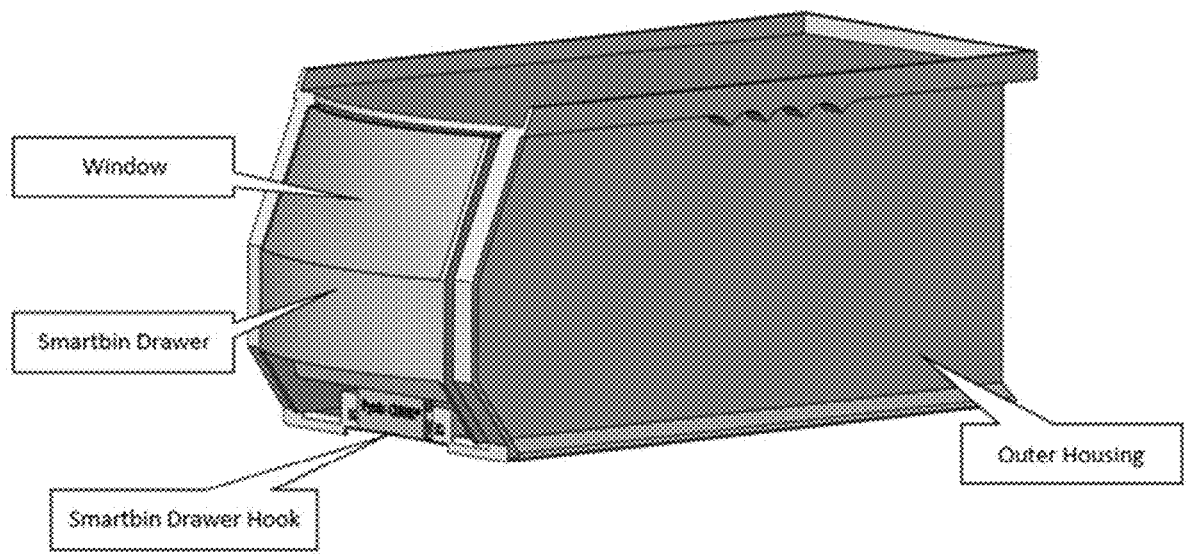
FIGS. 44A and 44B depict example smart bin drawers, according to various aspects of the subject technology.
Figure 44B:
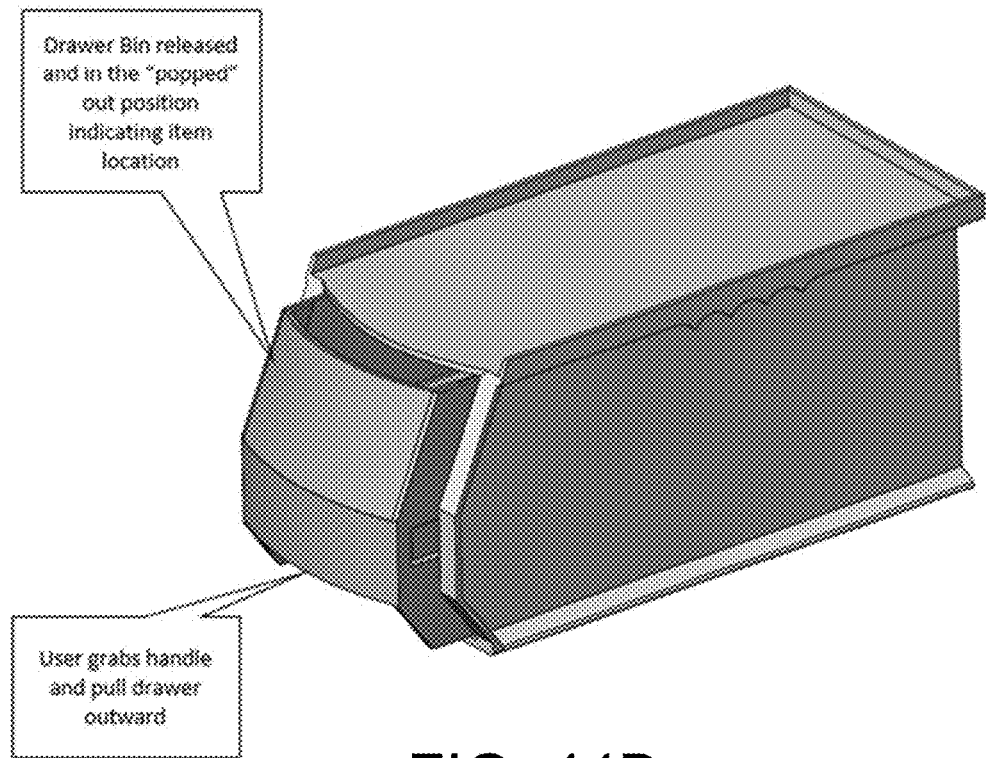

FIGS. 44A and 44B depict example smart bin drawers, according to various aspects of the subject technology. The smart bin may include a drawer base bin that resides in an outer housing. The smart bin may incorporate a handle. The smart bin may be configured to pull out horizontally from the outer housing and eventually hit a stop feature. Once the smart bin hits the stop feature it may be tilted downward. This drawer-based configuration of smart bin may allow for easy retrieval of items and visual accessibility for counting items. The smart bin may be spring loaded and "pop" outward on latch release indicating location of item (See FIG. 44B).

Figure 45A:
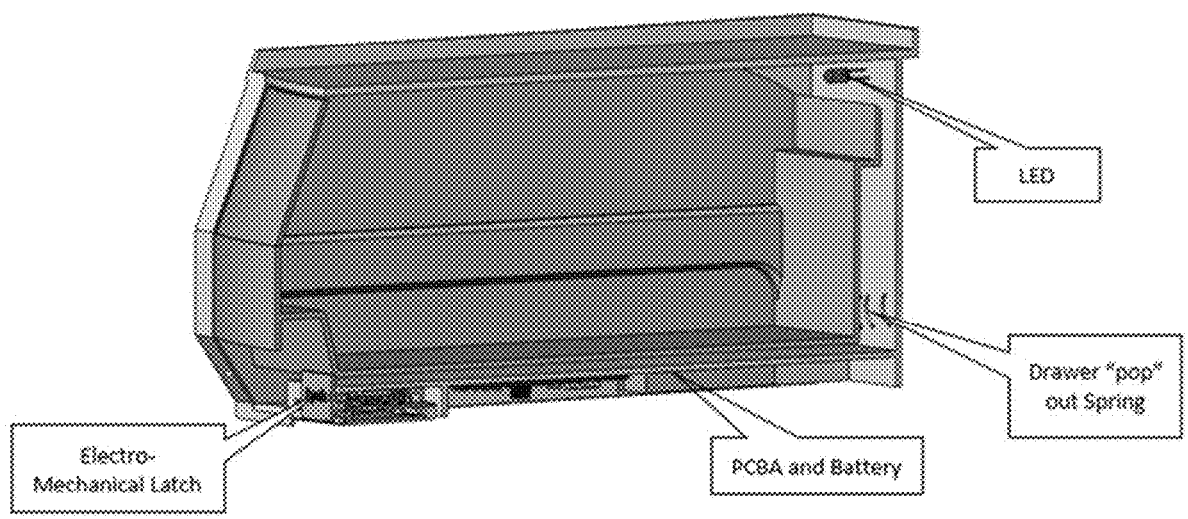
FIGS. 45A and 45B depict cut-away views of the example smart bin drawers, according to various aspects of the subject technology.
Figure 45B:
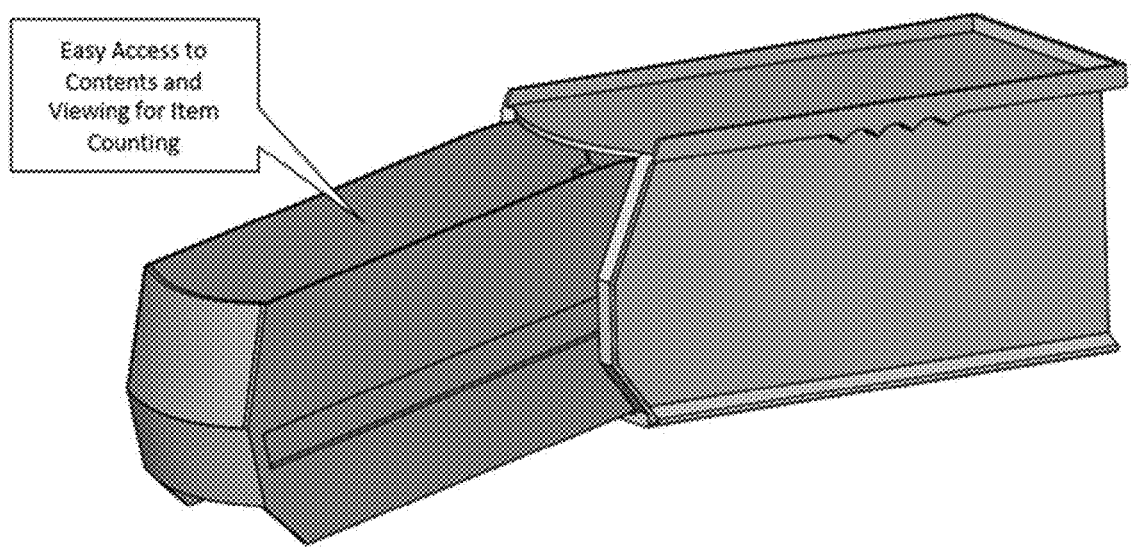

FIGS. 45A and 45B depict cut-away views of the example smart bin drawers, according to various aspects of the subject technology. According to some implementations, the outer housing may include features to mount a latch, PCBA, LEDs, and a battery. Also, the outer housing may include features to pivot storage bin, stops to limit bin rotation. The smart bin in the drawer-configuration may include features to mount a latch hook, mounting features for the window, and spring. The electro-mechanical latch may be powered by low power. The smart bin may further contains sensors that may interface with the drawer to indicate an open or close status. The latch may have on-board memory to digitally store content/location information.

Further Embodiments

With reference to FIG. 9A, the energy source 1180 utilized to power the devices may be static or dynamically configured to provide energy. Six example configurations are:

Config 1 (Distributed): Disposable batteries.
Config 2 (Distributed): Rechargeable batteries/super capacitor.
Config 3 (Centralized): One high capacity battery interfaced to enclosure with docking type or wired physical connector to redistribute power to storage space.
Config 3 (Centralized): External power supply interfaced to enclosure with docking type or wired physical connector to redistribute power to storage space.
Config 4 (Centralized): Power over Ethernet (PoE) interfaced to enclosure with docking type or wired physical connector to redistribute power to storage space.
Config 5 (Centralized): Wireless power transmitter interfaced to enclosure with docking type or wired physical connector to redistribute power to storage space.
Config 6 (Distributed): Wireless power transmitters on the enclosure interfaced to wireless receiver on each smart container.

One or more aspects or features of the subject matter described herein may be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one specifically configured programmable processor, which may be special or general purpose, coupled to receive data and specific instructions from, and to transmit data and instructions to, a storage system, at least one input device, and at least one output device. The programmable system or computing system may include one or more clients and/or servers. A client and server are generally remote from each other and typically interact through a communication network. The relationship of client and server arises by virtue of computer programs running on the respective computers and having a client-server relationship to each other.

These specific computer programs, which can also be referred to as programs, software, software applications, applications, components, or code, include machine instructions for a programmable processor, and may be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "implementation" does not imply that such implementation is essential to the subject technology or that such implementation applies to all configurations of the subject technology. A disclosure relating to an implementation may apply to all implementations, or one or more implementations. An implementation may provide one or more examples. A phrase such as an "implementation" may refer to one or more implementations and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. An access control assembly, comprising: a latching module comprising: a latching member; and a latch actuator configured to extend and retract the latching member; and an interface module coupled to the latching module, the interface module comprising: a module body defining a handle portion and an extension portion extending from the handle portion, wherein the extension portion is narrower than the handle portion and the module body is spaced apart from the latching module; an input device configured to receive a user input; and a controller operatively coupled to the latch actuator and configured to authenticate the user input and control the latching member in response to the authenticated user input.

Clause 2. The access control assembly of Clause 1, wherein the access control assembly is battery powered.

Clause 3. The access control assembly of Clause 2, wherein the module body defines a battery compartment.

Clause 4. The access control assembly of Clause 1, wherein the latching module is operatively coupled to the controller via a connector.

Clause 5. The access control assembly of Clause 4, wherein the module body defines a port to permit access to the connector.

Clause 6. The access control assembly of Clause 1, wherein the input device comprises a near field communication reader or a biometric reader.

Clause 7. The access control assembly of Clause 1, wherein the interface module comprises a status indicator.

Clause 8. The access control assembly of Clause 7, wherein the status indicator comprises an electronic-ink display.

Clause 9. A storage system comprising: a cabinet body defining a cabinet volume; a cabinet door coupled to the cabinet body, wherein the cabinet door is movable to enclose the cabinet volume; and an access control assembly coupled to the cabinet door, the access control assembly comprising: a latching module coupled to an inner surface of the cabinet door, the latching module comprising: a latching member; and a latch actuator configured to extend and retract the latching member relative to the cabinet door; and an interface module coupled to an outer surface of the cabinet door, the interface module comprising: a module body defining a handle portion and an extension portion extending from the handle portion, wherein the extension portion is narrower than the handle portion and the extension portion is adjacent to the outer surface of the cabinet door; an input device configured to receive a user input; and a controller operatively coupled to the latch actuator and configured to authenticate the user input and control the latching member in response to the authenticated user input.

Clause 10. The storage system of Clause 9, wherein latching module is coupled to the interface module through the cabinet door.

Clause 11. The storage system of Clause 9, wherein the latching module comprises a bracket coupled to the inner surface of the cabinet door.

Clause 12. The storage system of Clause 9, wherein the latching member is configured to engage the cabinet body in a closed position.

Clause 13. The storage system of Clause 9, wherein the latching module is operatively coupled to the controller through the cabinet door via a connector.

Clause 14. The storage system of Clause 13, wherein the module body defines a port to permit access to the connector.

Clause 15. The storage system of Clause 9, wherein the input device comprises a near field communication reader or a biometric reader.

Clause 16. The storage system of Clause 9, wherein the interface module comprises a status indicator.

Clause 17. The storage system of Clause 16, wherein the status indicator comprises an electronic-ink display.

Clause 18. The storage system of Clause 9, wherein the interface module comprises a position sensor to determine a position of the cabinet door.

Clause 19. A method comprising: providing a cabinet body with a cabinet door movable relative to the cabinet body; latching the cabinet door to the cabinet body to retain the cabinet door in a closed position via a latching module; unlatching the cabinet door from the cabinet body via the latching module; moving the cabinet door to an open position; and accessing a cabinet volume defined within the cabinet body.

Clause 20. The method of Clause 19, further comprising: authenticating a user via an authentication device; and unlatching the cabinet door from the cabinet body in response to authenticating the user via the authentication device.

Clause 21. A smart lock used to secure cabinets and drawers in non-acute and acute healthcare settings.

Clause 22. The smart lock of Clause 21, comprising a plurality of user interfaces, a server authorized actuator lock, a lock and door sensors, an identity authentication module or an enterprise solution for securing medication and guided loading of medication.

Clause 23. The smart lock of Clause 21, further comprising an E-ink user interface configured to display status of the smart lock system using icons such as battery level, network connectivity, status of the latch and door.

Clause 24. The smart lock of Clause 21, wherein the smart lock is configured to display alerts such as expired medication, medication below par, tamper detection.

Clause 25. The smart lock of Clause 21, wherein the smart lock is configured to display information collected from the environmental sensor, such as temperature of medication, monitor tamper evidence sensor signal, humidity, shock and vibration over time.

Clause 26. The smart lock of Clause 21, wherein the smart lock comprises a display that is user configurable.

Clause 27. The smart lock of Clause 21 further comprising a multicolor LED user interface.

Clause 28. The smart lock of Clause 27, wherein the LED color, flash pattern and intensity can indicate different statuses based on a user accessing the secure storage location and workflow. For example, during medication loading workflow the led lighting can guide the user to the medication at a glance. In another example, if the medications being secured by the smart lock has expired, the LED can flash red. In another example, during a medication audit, the system may guide by lighting the LEDs so the user can identify the medication easily. In another example, if the battery level is lower than threshold, the LEDs can flash in low intensity. In another example, the LED color and flash pattern can be selected to indicate authorized user unlocked the latch.

Clause 29. The smart lock of Clause 28, wherein a handheld device can scan the LED color, intensity, and flash pattern and identify its status during manufacturing or in field.

Clause 30. The smart lock of Clause 29, wherein an inspection equipment, a mobile application, or an optical reading device can read the multicolor visual indicator and obtain the failure modes and conditions on the smart lock.

Clause 31. The smart lock of Clause 21, wherein the smart lock automatically determines a plurality of user authorization methods and the user then selects one of the determined authorization methods to unlock the smart lock.

Clause 32. The smart lock of Clause 21, wherein the smart lock securely transmits the user identity to a server and receives a message or other authorization from the server to unlock the smart tote.

Clause 33. The smart lock of Clause 21, wherein the smart lock utilizes a contactless smart card. In some implementations, the smart lock utilizes a barcode, biometric identification, ECG-based wearable device, or a mobile phone.

Clause 34. The smart lock of Clause 21, wherein the smart lock utilizes remote authentication. For example, users can enter credentials at tablet or PC, or use a standalone authentication module, to gain access to the smart lock. If the user loses their badge or smart phone, a super user can provide remote authentication.

Clause 35. The smart lock of Clause 21, wherein the smart lock monitors NIST traceable environmental sensor & tamper detection data in real time.

Clause 36. The smart lock of Clause 21, wherein an audible sound indicates user actions such as presenting a badge to the smart lock or when an actuator command is been executed.

Clause 37. The smart lock of Clause 21, wherein the smart lock comprises a piezo beeper that uses different tones to indicate different actions.

Clause 38. The smart lock of Clause 21, wherein the smart lock can use a plurality of PAN protocols such as (802.15.4/BLE) to talk to the remote device.

Clause 39. The smart lock of Clause 21, wherein the smart lock includes a beacon for asset tracking, environmental sensor and tamper detection monitoring, real time, and offline mode support, or tote content identification and inventory tracking.

Clause 40. The smart lock of Clause 21, wherein the smart lock can bypass hospital IT thereby reducing implementation time.

Clause 41. The smart lock of Clause 21, wherein the smart lock acts as a companion device for devices placed inside the enclosure to bridge communications. Connected devices placed inside enclosures, such as refrigerators and metal cabinets, may have their radio signals attenuated and have difficulty communicating to hubs located further away. In these cases, another device such as the smart lock may be used as companion device to enable reliable communication to the hub/gateway.

Clause 42. The smart lock of Clause 21, wherein the smart lock can utilize a slave role communicating to the hub or a master role communicating to the devices behind the enclosure.

Clause 43. The smart lock of Clause 21, wherein the smart lock can create a multi-level network hierarchy in the network of devices all communicating back to the hub, either directly or through another device.

Clause 44. The smart lock of Clause 21, wherein the smart lock uses disposable batteries or rechargeable batteries.

Clause 45. The smart lock of Clause 21, wherein the smart lock has sensors to read the status of both the latch and door/drawer at all times. This capability enables workflow execution and may also be used to detect tamper detection.

Clause 46. A method for conserving power in battery operated devices based on system factors and user preference, comprising: placing a device in a lower power state, wherein the device can wake up periodically (wake up period), enable radio communications. check in with a gateway/hub for updates or perform transactions, wherein power saving states can adjust device responsiveness and the wake up period is configured by the gateway/hub devices based on system usage factors and user preferences.

Clause 47. The method in Clause 46, further comprising adjusting power states based on user presence. For example, if users are present, the devices may be placed in more responsive states in anticipation of the system being used. If users are not present, the devices may be put in less responsive states. This may help to maximize, improve, or achieve power savings.

Clause 48. The method in Clause 46, further comprising detecting presence in different ways, including by users logging into the system and by occupancy sensors, such as motion, radar, and proximity sensors. Occupancy sensors may be powered devices located in the medical room area and are configured to interface with the gateway/hub.

Clause 49. The method in Clause 46, wherein users are able to input office schedules into the system and power states may be adjusted based on this schedule.

Clause 50. The method in Clause 46, wherein to wake up the device from deep sleep mode, microphones may detect key word activation, user action (for example, by pushing a button), or system usage factors (such as user presence).

Clause 51. The method in Clause 46, wherein power states can be adjusted by machine learning ("ML") algorithms running on the hub/gateway and/or cloud.

Clause 52. A method for energy harvesting using a plurality of sources to increase smart lock operation life.

Clause 53. The method in Clause 53, further comprising using (i) piezo transducers interfaced to buttons, (ii) electromagnetic induction from a lock actuator or drawer/door open and close action, or (iii) wireless energy from RF sources to harvest energy.

Clause 54. A smart latch attachable to a refrigerator, the smart latch comprising: an actuator configured to open and close a latch to secure a door of the refrigerator; a communication interface; a display; and a processor configured to: retrieve, via the communication interface, inventory and temperature status for one or more smart containers within the refrigerator; output, via the display, the inventory and temperature status; receive a user credential for accessing the refrigerator; validate the user credential for accessing the refrigerator; trigger the actuator to open the latch, thereby allowing the door to be opened; and trigger the actuator to close the latch after detecting that the door is closed, thereby securing the door.

Clause 55. The smart latch of Clause 1, wherein the latch is configured to close into a latch plate attached to the door.

Clause 56. The smart latch of Clause 1, wherein the smart latch is attachable to the refrigerator via a mounting plate that bolts to a side of the refrigerator that is opposite to another side of the refrigerator that is proximate to a hinge of the door.

Clause 57. The smart latch of Clause 1, wherein the processor is further configured to: record, within a non-volatile data store, periodic sensor data.

Clause 58. The smart latch of Clause 4, wherein the one or sensors include at least one of a temperature sensor, a shock sensor, a vibration sensor, a tamper sensor, and a location sensor.

Clause 59. The smart latch of Clause 1, wherein the processor is further configured to output a warning to the display when the temperature status exceeds a predefined safe range.

Clause 60. The smart latch of Clause 1, wherein the display includes at least one of an e-ink display, a liquid crystal display (LCD), and a light emitting diode (LED).

Clause 61. The smart latch of Clause 1, wherein the processor is further configured to synchronize the inventory and temperature status with a remote server via the communication interface.

Clause 62. The smart latch of Clause 8, wherein the synchronizing utilizes mobile mesh networking to use other smart latches and smart devices as nodes.

Clause 63. The smart latch of Clause 1, further comprising an identity authentication module including at least one of a smartcard reader and a biometric sensor, and wherein the processor is configured to receive and validate the user credential using the identity authentication module.

Clause 64. The smart latch of Clause 1, wherein the communication interface is configured to function as a wireless repeater for the one or more smart containers within the refrigerator.

Clause 65. The smart latch of Clause 1, wherein the processor is further configured to: receive a request to locate a refrigerated item; determine, in a local cache, a remote smart latch attached to a closest remote refrigerator containing the refrigerated item; verify, with the remote smart latch via the communication interface, that the closest remote refrigerator still contains the refrigerated item; and cause a position of the remote smart latch to be displayed.

Clause 66. The smart latch of Clause 12, wherein the processor is further configured to: cause a remote device to display a map for guiding a user to the remote smart latch; and direct one or more smart devices between the smart latch and the remote smart latch to illuminate a path to the remote smart latch.

Clause 67. The smart latch of Clause 1, wherein the processor is configured to validate the user credentials for accessing the refrigerator based on the temperature status.

Clause 68. A method for providing secure access control and temperature monitoring for a refrigerator, the method comprising: providing a smart latch for attaching to the refrigerator; retrieving, via a communication interface, inventory and temperature status for one or more smart containers within the refrigerator; outputting, via a display, the inventory and temperature status; receiving a user credential for accessing the refrigerator; validating the user credential for accessing the refrigerator; triggering an actuator to open a latch, thereby allowing a door of the refrigerator to be opened; and triggering the actuator to close the latch after detecting that the door is closed, thereby securing the door.

Clause 69. The method of Clause 15, wherein providing the smart latch comprises attaching the smart latch to the refrigerator via a mounting plate that bolts to a side of the refrigerator that is opposite to another side of the refrigerator that is proximate to a hinge of the door.

Clause 70. The method of Clause 15, wherein triggering the actuator to close the latch comprises closing the latch through a latch opening into a latch plate attached to the door.

Clause 71. The method of Clause 15, further comprising outputting a warning to the display when the temperature status exceeds a predefined safe range.

Clause 72. The method of Clause 15, further comprising synchronizing the inventory and temperature status with a remote server via the communication interface.

Clause 73. A non-transitory storage medium comprising instructions that, when read by one or more processors, cause a method comprising: retrieving, via a communication interface, inventory and temperature status for one or more smart containers within a refrigerator; outputting, via a display, the inventory and temperature status; receiving a user credential for accessing the refrigerator; validating the user credential for accessing the refrigerator; triggering an actuator to open a latch, thereby allowing a door of the refrigerator to be opened; and triggering the actuator to close the latch after detecting that the door is closed, thereby securing the door.

Clause 74. A smart latch attachable to an enclosure, the smart latch comprising: an actuator configured to open and close a latch to secure a door of the enclosure; a communication interface; a display; and a processor configured to: receive a user credential for accessing the enclosure; validate the user credential for accessing the enclosure; trigger the actuator to open the latch, thereby allowing the door to be opened; and trigger the actuator to close the latch after detecting that the door is closed, thereby securing the door.

Clause 75. The smart latch of Clause 74, wherein the enclosure comprises a refrigerator.

Clause 76. The smart latch of clause 75, wherein the smart latch is attachable to the refrigerator via a mounting plate that bolts to a side of the refrigerator that is opposite to another side of the refrigerator that is proximate to a hinge of the door.

Clause 77. The smart latch of Clause 75, wherein the processor is further configured to: retrieve, via the communication interface, inventory and temperature status for one or more smart containers within the refrigerator; and output, via the display, the inventory and temperature status.

Clause 78. The smart latch of clause 75, wherein the processor is further configured to output a warning to the display when the temperature status exceeds a predefined safe range.

Clause 79. The smart latch of clause 75, wherein the processor is further configured to synchronize the inventory and temperature status with a remote server via the communication interface.

Clause 80. The smart latch of clause 75, wherein the processor is further configured to: receive a request to locate a refrigerated item; determine, in a local cache, a remote smart latch attached to a closest remote refrigerator containing the refrigerated item; verify, with the remote smart latch via the communication interface, that the closest remote refrigerator still contains the refrigerated item; and cause a position of the remote smart latch to be displayed.

Clause 81. The smart latch of clause 74, wherein the latch is configured to close into a latch plate attached to the door.

Clause 82. The smart latch of clause 74, wherein the processor is further configured to: record, within a non-volatile data store, periodic sensor data.

Clause 83. The smart latch of clause 82, wherein the one or sensors include at least one of a temperature sensor, a shock sensor, a vibration sensor, a tamper sensor, and a location sensor.

Clause 84. An access control assembly configured to be connected to an enclosure body, having an enclosure volume and an enclosure door that is movable to enclose the enclosure volume, the access control assembly comprising: a latching module configured to couple to an inner surface of the enclosure door, the latching module comprising: a latching member; and a latch actuator configured to extend and retract the latching member relative to the enclosure door; and an interface module configured to couple to an outer surface of the enclosure door, the interface module comprising: an input device configured to receive a user input; and a controller operatively coupled to the latch actuator and configured to authenticate the user input and control the latching member in response to the authenticated user input.

Clause 85. The access control assembly of Clause 84, wherein the interface module further comprises: a module body defining a handle portion and an extension portion extending from the handle portion, wherein the extension portion is narrower than the handle portion and the extension portion is adjacent to the outer surface of the enclosure door.

Clause 86. The access control assembly of Clause 84, wherein the access control assembly is configured to be connected to a cabinet.

Clause 87. The access control assembly of Clause 84, wherein the access control assembly is configured to be connected to a refrigerator.

Clause 88. The access control assembly of Clause 84, wherein latching module is configured to couple to the interface module through the enclosure door.

Clause 89. The access control assembly of Clause 84, wherein the latching module comprises a bracket that is configured to couple to the inner surface of the enclosure door.

Clause 90. The access control assembly of Clause 84, wherein the controller is further configured to: retrieve, via the communication interface, inventory and temperature status for one or more smart containers within the enclosure; and output, via the display, the inventory and temperature status.

Clause 91. A method comprising: latching a movable enclosure door to an enclosure body to retain the enclosure door in a closed position via a latching module; authenticating a user via an authentication device; unlatching the enclosure door from the enclosure body via the latching module to permit the enclosure door to move to an open position in response to authenticating the user via the authentication device; and accessing an enclosure volume defined within the enclosure body.

Clause 92. The method of Clause 91, wherein the authentication device authenticates the user via a near field communication reader or a biometric reader.

Clause 93. The method of Clause 91, further comprising: retrieving, via a communication interface, inventory and temperature status for one or more smart containers within the enclosure; and outputting, via a display, the inventory and temperature status.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer," "server," "processor," and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit this disclosure.

The term website, as used herein, may include any aspect of a website, including one or more web pages, one or more servers used to host or store web related content, etc. Accordingly, the term website may be used interchangeably with the terms web page and server. The predicate words "configured to," "operable to," and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

Features described may include machine learning. Machine learning may include models, equations, artificial neural networks, recurrent neural networks, convolutional neural networks, decision trees, or other machine readable artificial intelligence structure. Examples of machine learning and modeling features which may be included in the embodiments discussed above are described in "A survey of machine learning for big data processing" by Qiu et al. in EURASIP Journal on Advances in Signal Processing (2016) which is hereby incorporated by reference in its entirety.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A smart latch attachable to an enclosure of a refrigerator, the smart latch comprising:
an actuator configured to open and close a latch to secure a door of the enclosure;
a communication interface;
a non-transitory machine-readable memory,
a display; and
a processor configured to:
receive a user credential for accessing the enclosure;
validate the user credential for accessing the enclosure;
trigger the actuator to open the latch, thereby allowing the door to be opened;
trigger the actuator to close the latch after detecting that the door is closed, thereby securing the door;
receive a request for a refrigerated item;
determine, from a local inventory in a local cache within the non-transitory machine-readable memory of the smart latch, whether the refrigerated item is in the refrigerator;
identify, from the local inventory in the local cache, responsive to determining that the refrigerated item is not in the refrigerator attached to the smart latch, that the requested refrigerated item is contained in a remote refrigerator attached to a different smart latch, the remote refrigerator and different smart latch being geographically separated from the refrigerator attached to the smart latch and the smart latch;

verify, with the smart latch via the communication interface, that the remote refrigerator still contains the refrigerated item; and cause an indication of a location of the remote refrigerator and different smart latch to be displayed on the display.

2. The smart latch of claim 1, wherein the smart latch is attachable to the refrigerator via a mounting plate that bolts to a side of the refrigerator that is opposite to another side of the refrigerator that is proximate to a hinge of the door.

3. The smart latch of claim 1, wherein the processor is further configured to synchronize a status of the local inventory and a temperature with a remote server via the communication interface.

4. The smart latch of claim 3, wherein the processor is further configured to:

receive, via the communication interface, condition tracking information including inventory and temperature status associated with the refrigerated item stored within the remote refrigerator; and output, via the display, the inventory and temperature status associated with the refrigerated item stored within the remote refrigerator.

5. The smart latch of claim 4, wherein the processor is further configured to output a warning to the display when the temperature status exceeds a predefined safe range.

6. The smart latch of claim 1, wherein the latch is configured to close into a latch plate attached to the door.

7. The smart latch of claim 1, wherein the processor is further configured to: record, within a non-volatile data store, periodic sensor data.

8. The smart latch of claim 7, wherein the smart latch is operably connected to one or more sensors associated with the enclosure, and wherein the one or sensors include at least one of a temperature sensor, a shock sensor, a vibration sensor, a tamper sensor, and a location sensor.

9. The smart latch of claim 1, wherein the processor is further configured to:

open the latch responsive to receiving the user credential satisfying a predetermined privilege level;

determine a temperature status within the enclosure;

determine that the temperature status within the enclosure does not satisfy a threshold range;

increase, responsive to determining that the temperature status within the enclosure does not satisfy the threshold range, the predetermined privilege level from a default privilege level to a higher privilege level;

determine that the user credential satisfies the higher privilege level; and responsive to determining that the user credential satisfies the higher privilege level, trigger the actuator to open the latch, thereby allowing the door to be opened.

* * * * *